US006951724B2

(12) United States Patent
Gatti

(10) Patent No.: US 6,951,724 B2
(45) Date of Patent: Oct. 4, 2005

(54) METHODS FOR DETECTION OF ATAXIA TELANGIECTASIA MUTATIONS

(75) Inventor: Richard A. Gatti, Sherman Oaks, CA (US)

(73) Assignee: The Regents of the University of California, Oakland, CA (US)

(*) Notice: Subject to any disclaimer, the term of this patent is extended or adjusted under 35 U.S.C. 154(b) by 483 days.

(21) Appl. No.: 10/175,225

(22) Filed: Jun. 17, 2002

(65) Prior Publication Data

US 2003/0082582 A1 May 1, 2003

Related U.S. Application Data

(62) Division of application No. 09/360,416, filed on Jul. 23, 1999, now Pat. No. 6,458,536.

(51) Int. Cl.[7] .............................. C12Q 1/68; C12P 19/34; C07H 21/04
(52) U.S. Cl. ........................ 435/6; 435/91.1; 435/91.2; 536/23.5; 536/24.31; 536/24.33
(58) Field of Search .......................... 435/6, 91.1, 91.2; 536/23.5, 24.31, 24.33

(56) References Cited

U.S. PATENT DOCUMENTS

| | | | | |
|---|---|---|---|---|
| 4,683,195 A | | 7/1987 | Mullis | |
| 4,683,202 A | | 7/1987 | Mullis | |
| 5,728,807 A | * | 3/1998 | Shiloh et al. | 530/350 |
| 5,756,288 A | * | 5/1998 | Shiloh | 435/6 |
| 5,770,372 A | * | 6/1998 | Concannon | 435/6 |
| 5,777,093 A | * | 7/1998 | Shiloh et al. | 536/23.5 |
| 5,843,654 A | * | 12/1998 | Heisler et al. | 435/6 |
| 5,858,661 A | * | 1/1999 | Shiloh | 435/6 |
| 5,925,517 A | * | 7/1999 | Tyagi et al. | 435/6 |
| 5,955,279 A | * | 9/1999 | Gatti et al. | 435/6 |
| 6,200,749 B1 | * | 3/2001 | Shiloh | 435/6 |
| 6,265,158 B1 | * | 7/2001 | Shiloh | 435/6 |
| 6,617,104 B2 | * | 9/2003 | Swift | 435/6 |

FOREIGN PATENT DOCUMENTS

WO    WO 97/47772    12/1997

OTHER PUBLICATIONS

Exhibit 4 is a publication, J. Sambrook et al., "Molecular Cloning: A Laboratory Manual" (2d ed., Cold Spring Harbor Laboratory Press, Cold Spring Harbor, New York, 1989), vol. 1, pp. 5.3–5.9.
Exhibit 5 is a publication, R.A. Gatti, "Ataxia–Telectangiasia" in *Genetic Basis of Human Cancer* (Vogelstein & Kinzler, eds., McGraw–Hill, New York, 1998).
Exhibit 6 is a publication, E. Lange et al., "Location of an Ataxia–Telangiectasia to a ~ 500kb Interval on Chromosome 11q23.1:Linkage Analysis of 176 Families in an International Consortium," *Am. J. Hum. Genet.* 57:112–119 (1995).

Exhibit 7 is a publication, N. Uhrhammer et al., "Sublocalization of an Ataxia–Telangiectasia Gene Distal to D11 S384 by Ancestral Haplotyping in Costa Rican Families," *Am. J. Hum. Genet.* 57:103–111 (1995).
Exhibit 8 is a publication, K. Savitsky et al., "A Single Taxia–Telangiectasia Gene with a Product Similar to a Pi–3 Kinase," *Science* 268:1749–1753 (1995).
Exhibit 9 is a publication, G. Chen & E.Y.–H.P. Lee, "The Product of the ATM Gene is a 370–kDa Nuclear Phosphoprotein," *J. Biol. Chem.* 271:33693–33697 (1996).
Exhibit 10 is a publication, P. Concannon & R.A. Gatti, "Diversity of *ATM* Gene Mutations in Patients with Ataxia–Telangiectasia," *Hum. Mutat.* 10:100–107 (1997).
Exhibit 11 is a publication, P.J. Byrd et al., "Mutations Revealed by Sequencing the 5' Half of the Gene for Ataxia–Telangiectasia," *Hum. Mol. Genet.* 5:145–149 (1996).
Exhibit 12 is a publication, J. Wright et al., "A High Frequency of Distinct *ATM* Mutations in Ataxia Telangiectasia," *Am. J. Hum.Genet.* 59:839–846 (1996).
Exhibit 13 is a publication, T. Sasaki et al., "*ATM* Mutations in Patients with Ataxia–Telangiectasia Screened by a Hierarchical Strategy," *Hum. Mutat.* 12:186–195 (1998).
Exhibit 14 is a publication, M. Telatar et al., "Ataxia–Telangiectasia: Mutations in *ATM* cDNA Detected by Protein–Truncation Screening," *Am. J. Hum. Genet.* 59:40–44 (1996).
Exhibit 15 is a publication, K. Savitsky et al., "The Complete Sequence of the Coding Region of the ATM Gene Reveals Similarity to Cell Cycle Regulators in Different Species," *Hum. Mol. Genet.* 4:2025–2032 (1995).
Exhibit 16 is a publication, A.R. Lehmann & A.M. Carr, "The Ataxia–Telangiectasia Gene: A Link Between Checkpoint Controls, Neurodegeneration, and Cancer," *Trends Genet.* 11:375–377 (1995).
Exhibit 17 is a publication, V.A. Zakian, "*ATM*–Related Genes: What Do They Tell Us About Functions of the Human Gene," *Cell* 82:685–687 (1995).
Exhibit 18 is a publication, M.F. Lavin et al., "Relationship of the Ataxia–Telangiectasia Protein ATM to Phosphoinositide 3–Kinase," *Trends Biol. Sci.* 20:382–383 (1995).

(Continued)

*Primary Examiner*—Kenneth R. Horlick
(74) *Attorney, Agent, or Firm*—Knobbe Martens Olson and Bear

(57) ABSTRACT

The present invention is directed to a method of screening large, complex, polyexonic eukaryotic genes such as the ATM gene for mutations and polymorphisms by an improved version of single strand conformation polymorphism (SSCP) electrophoresis that allows electrophoresis of two or three amplified segments in a single lane. The present invention also is directed to new mutations and polymorphisms in the ATM gene that are useful in performing more accurate screening of human DNA samples for mutations and in distinguishing mutations from polymorphisms, thereby improving the efficiency of automated screening methods.

33 Claims, 2 Drawing Sheets

OTHER PUBLICATIONS

Exhibit 19 is a publication, C.T. Keith & S.L. Schreiber, PIK–Related Kinases: DNA Repair, Recombination, and Cell Cycle Checkpoints, *Science* 270:50–51 (1995).

Exhibit 20 is a publication, M. Platzer et al., "Ataxia–Telangiectasia Locus: Sequence Analysis of 184 kb of Human Genomic DNA Containing the Entire *ATM* Gene," *Genome Res.* 7: 592–605 (1997).

Exhibit 21 is a publication, M. Orita et al., "Detection of Polymorphisms of Human DNA by Gel Electrophoresis as Single–Strand Conformation Polymorphisms," *Proc. Natl. Acad. Sci. USA* 86: 2766–2770 (1989).

Exhibit 22 is a publication, S. Tyagi et al., "Multicolor Molecular Beacons for Allele Discrimination," *Nature Biotechnol.* 16: 49–53 (1998).

Exhibit 23 is a publication, J. Keen et al., "Rapid Detection of Single Base Mismatches as Heteroduplexes on Hydrolink Gels," *Trends Genet.* 7:5 (1991).

Exhibit 24 is a publication, J.C. Hacia et al., "Strategies for Mutational Analysis of the Large Multiexon *ATM* Gene using High–Density Oligonucleotide Arrays," *Genome Res.* 8: 1245–1258 (1998).

Exhibit 25 is a publication, M. Telatar et al., "Ataxia–Telangiectasia: Identification and Detection of Founder–Effect Mutations in the *ATM* gene in Ethnic Populations," *Am. J. Hum. Genet.* 62:86–87 (1998).

Exhibit 26 is a publication, J. Daussel et al., "Centre d'Etude du Polymorphisme Humaine (CEPII): Collaborative Genetic Mapping of the Human Genome," *Genomics* 6:575–577 (1990).

Exhibit 27 is a publication, M. Grompe, "The Rapid Detection of Known Mutations in Nucleic Acids," *Nature Genet.* 5:111–117 (1993).

Exhibit 28 is a publication, L. Vorechovsky et al., "ATM Mutations in Cancer Families," *Cancer Res.* 56: 4130–4133 (1996).

Exhibit 29 is a publication, T. Dork et al., "A Frequent Polymorphism of the Gene Mutated in Ataxia–Telangiectasia," *Mol. Cell. Probes* 11:71–73 (1997).

Exhibit 30 is a publication, C. McConville et al., "Mutations Associated with Variant Phenotypes in Ataxia–Telangiectasia," *Am. J. Hum. Genet.* 59:329–330 (1996).

Exhibit 31 is a publication, M. Chillon et al., "Mutations in the Cystic Fibrosis Gene in Patients with Congenital Absence of the Vas Deferens," *N. Engl. J. Med.* 332:1475–1480 (1995).

Exhibit 32 is a publication, X. Estivill, "Complexity in a Monogenic Disease," *Nature Genet.* 12:350 (1996). Exhibit 33 is a publication, S. Pedemonte et al., "Novel Germline APC Variants in Patients with Multiple Adenomas," *Genes Chromosomes Cancer* 22:257–267 (1998).

Exhibit 34 is a publication, N. Makridakis et al., "A Prevalent Missense Substitution that Modulates Activity of Prostatic Steroid 5–Reductase," *Cancer Res.* 57:1020–1022 (1997).

Exhibit 35 is a publication, R. Nowak, "Discovery of AT Gene Sparks Research Bonanza," *Science* 268: 1700–1701 (1995).

Exhibit 36 is a publication, M. Telatar et al., "A Model for ATM Heterozygote Identification in a Large Population: Four Founder–Effect ATM Mutations Identify Most of Costa Rican Patients with Ataxia Telangiectasia," *Mol. Genet . Metabol.* 64: 36–43 (1998).

Exhibit 37 is a publication, M.F. Lavin et al., "Eighth International Workshop on Ataxia–Telangiectasia (ATW8)," *Cancer Res.* 59: 3845–3849 (Aug. 1, 1999). Exhibit 37 is not prior art, as it was published after the filing date of above–identified application. It is being provided for convenience only.

Exhibit 38 is a publication, K.M. Cerosaletti et al., "Fine Localization of the Nijmegen Breakage Syndrome Gene to 8q21: Evidence for a Common Founder Haplotype," *Am. J. Hum. Genet.* 63: 125–134 (1998).

Exhibit 39 is a publication, M. Telatar et al., "Atasia–Telangiectasia: Identification and Detection of Founder–Effect Mutations in the ATM Gene in Ethnic Populations," *Am. J. Hum. Genet.* 62:86–97 (1998).

* cited by examiner

METHODS FOR DETECTION OF ATAXIA TELANGIECTASIA MUTATIONS

RELATED APPLICATIONS

This is a divisional of U.S. patent application Ser. No. 09/360,416, filed on Jul. 23, 1999 now U.S. Pat. No. 6,458,536.

GOVERNMENT RIGHTS

This invention was made with Government support under Grant No. DEFG0387ER60548, awarded by the Department of Energy, and Grant No. NS35311, awarded by the National Institutes of Health. The Government has certain rights in this invention.

BACKGROUND OF THE INVENTION

This invention is directed to methods for detecting polymorphisms in complex eukaryotic genes, particularly the gene for ataxia telangiectasia, and to polymorphisms detected by those methods.

Many autosomal recessive genetic disorders are caused by mutations in complex single genes that cause the genes to malfunction, producing a defective product or no product at all. Many of these genes include multiple exons, promoters, and other significant regions.

Ataxia-telangiectasia (A-T) (MIM208900) is an autosomal recessive disorder characterized by progressive cerebellar degeneration, immunodeficiency, growth retardation, premature aging, chromosomal instability, acute sensitivity to ionizing radiation, and cancer predisposition (R. A. Gatti, "Ataxia-Telangiectasia" in *Genetic Basis of Human Cancer* (Vogelstein Kinzler, eds. McGraw-Hill, New York, 1998)).

The gene responsible for A-T, ATM, was initially localized to chromosome 11q23.1 (E. Lange et al., "Location of an Ataxia-Telangiectasia to a ~500 kb Interval on Chromosome 11q23.1:Linkage Analysis of 176 Families in an International Consortium," *Am. J. Hum. Genet.* 57:112–119 (1995); N. Uhrhammer et al., "Sublocalization of an Ataxia-Telangiectasia Gene Distal to D11 S384 by Ancestral Haplotyping in Costa Rican Families," *Am. J. Hum. Genet.* 57:103–111 (1995)) and, on this basis, was positionally cloned by Savitsky et al. (K. Savitsky et al., "A Single Ataxia-Telangiectasia Gene with a Product Similar to a PI-3 Kinase," *Science* 268:1749–1753 (1995)). It spans about 150 kb of genomic DNA, encodes a major transcript of 13 kb, and a 370 kDa protein (G. Chen & E. Y. H. P. Lee, "The Product of the ATM Gene is a 370-kDa Nuclear Phosphoprotein," *J. Biol. Chem.* 271:33693–33697 (1996)). Subsequently, a wide spectrum of ATM mutations has been detected in A-T patients, spread throughout the gene and without evidence of a mutational hot spot (P. Concannon & R. A. Gatti, "Diversity of ATM Gene Mutations in Patients with Ataxia-Telangiectasia," *Hum. Mutat.* 10:100–107 (1997)).

Procedures used for mutation screening in the ATM gene have included restriction-endonuclease fingerprinting (REF) (K. Savitsky et al. supra (1995); P. J. Byrd et al., "Mutations Revealed by Sequencing the 5' Half of the Gene for Ataxia-Telangiectasia," *Hum. Mol. Genet.* 5:145–149 (1996)), the single-strand conformation polymorphism (SSCP Technique) J. Wright et al., "A High Frequency of Distinct ATM Mutations in Ataxia in Telangiectasia," *Am. J. Hum. Genet.* 59:839–846 (1996); T. Sasaki et al., "ATM Mutations in Patients with Ataxia-Telangiectasia Screened by a Hierarchical Strategy," *Hum. Mutat.* 12:186–195 (1998)), and the protein truncation test (PTT); (M. Telatar et al., "Ataxia-Telangiectasia: Mutations in ATM cDNA Detected by Protein-Truncation Screening," *Am. J. Hum. Genet.* 59:40–44 (1996)).

The ATM gene shows homology with protein kinases in yeast (TEL-1), drosophila (Mei-41) and human (DNA-PK) and is most closely related to DNA-PK and TEL-1(Savitsky et al., (1995), supra; K. Savitsky et al., *Hum. Mol. Genet.* 4:2025–2032 (1995); Lehmann et al., *Trends Genet.* 11:375–377 (1995); Zakin, *Cell* 82:685–687 (1995); Lavin et al., *Trends Biol. Sci.* 20:382–383 (1995); Keith et al., *Science* 270:50–51 (1995)).

The nucleotide sequence encoding the ATM protein is SEQ ID NO: 1. This corresponds to GenBank Accession No. U33841. The open reading frame is 9168 nucleotides. There is a 3' untranslated region (UTR) and a 5' UTR. SEQ ID NO: 2 is the amino acid sequence of the deduced ATM protein. It has 3056 amino acids. The ATM gene product contains a phosphatidylinositol-3 kinase (PI-3) signature sequence at codons 2855–2875. Mutation analyses in the initial report by Savitsky et al. (K. Savitsky et al. (1995), supra) use restriction endonuclease fingerprinting to identify mutations in the reverse-transcribed 5.9 kb carboxy-terminal end, which included the PI-3 signature sequence, of the 10 kb transcript that was available at that time (K. Savitsky et al., *Hum. Mol. Genet.* 4:2025–2032 (1995)). Both in-frame and frameshift mutations were found. Because the methodology used for screening for mutations biases the types of mutations found, there is a need to use different screening methods to identify further mutations in the ATM gene. The complete 150 kb genomic sequence was subsequently published (M. Platzer et al., "Ataxia-Telangiectasia Locus: Sequence Analysis of 184 kb of Human Genomic DNA Containing the entire ATM Gene," *Genome Res.* 7: 592–605 91988) and assigned Accession Number V82828.

The ATM gene is an example of a complex polyexonic eukaryotic gene that codes for a large protein product, in which defects appear as autosomal recessive mutations. There exists a large number of clinically important genes of this category, and improved methods of detecting polymorphisms in such genes are needed. In particular, there is a need for methods that can use either DNA or RNA as starting materials so that they are not dependent on existence of RNA molecules. Previous techniques include restriction endonuclease fingerprinting (REF), the single-stranded conformation polymorphism (SSCP) technique and the protein truncation test (PTT). There is also a need for a method that can detect mutations occurring in non-coding regions such as control elements, which would be missed by the protein truncation test. Therefore, there is a need for improved methods of detection of mutations and polymorphisms in such complex polyexonic eukaryotic structural genes.

Because of the severity of the disease associated with mutations in the ATM gene, patients or families frequently request confirmation of a suspected diagnosis of A-T. If the mutation is already known in a family, it is much easier to test other family members to see whether they carry that mutation. Since carriers of ATM mutations (i.e., heterozygotes with one normal gene) may also be at an increased risk of cancer, particularly breast cancer, testing for such mutations has attracted much commercial interest. Automated chips and readers are being developed by many companies; however, these readers have an error rate of about 1/1000, making it difficult to distinguish real mutations from errors or normal variations (i.e., polymorphisms). Approximately 23,000 nucleotides must be screened to identify most ATM mutations. A normal polymorphism appears every 500 nucleotides. Thus, in a region of 23,000 nucleotides being searched, there should be one (or possibly two) mutations amidst 23+46+2=71 errors and polymorphisms. The interpretation of such information is best approached by "look-up" tables that list all known polymorphisms and mutations (sometimes referred to as SNPs or single nucleotide polymorphisms. Therefore, there is a need for improved methods of detecting polymorphisms in the ATM gene and in other large, complex, polyexonic genes in order to improve such automated screening.

SUMMARY

One aspect of the present invention is method of detecting a mutation or a polymorphism in the human ataxia telangiectasia gene comprising the steps of:

(1) amplifying a plurality of nonoverlapping nucleic acid segments from the human ataxia telangiectasia gene;

(2) subjecting the amplified nonoverlapping nucleic acid segments to single-stranded conformation polymorphism electrophoresis in a number of lanes such that two or three amplified nucleic acid segments are electrophoresed per lane, the electrophoresis of the segments electrophoresed in the same lane being initiated at different times, such that the signals from each amplified nucleic acid segment are distinct in each lane, the time interval between the initiation of electrophoresis for each segment being chosen to ensure that signals resulting from the electrophoresis are distinct for each segment electrophoresed in the same lane; and (3) comparing the signals from the resulting single-stranded conformation polymorphism electrophoresis for each segment in each of the lanes to detect the mutation or polymorphism.

The plurality of nonoverlapping nucleic acid segments that are amplified can be RNA and the segments can be amplified by the reverse transcriptase-polymerase chain reaction mechanism. Alternatively, the plurality of nonoverlapping nucleic acid segments that amplified can be DNA and the segments can be amplified by the polymerase chain reaction mechanism.

The method preferably further comprises the step of cleaving amplified products larger than about 350 bases with a restriction endonuclease that cleaves the amplified products into fragments that are less than about 350 bases.

Typically, the electrophoresis occurs in polyacrylamide gels with glycerol as a gel matrix from about 150 to about 250 volts for about 14 to 16 hours. Preferably, the electrophoresis is performed in a plurality of gels so that the step of comparing the signals resulting from the electrophoresis of the amplified nucleic acid segments can detect mutations or polymorphisms in a plurality of segments of the gene. This procedure is entitled mega-SSCP.

A set of 70 primers can be used, as shown in Table 1.

The method can also be applied to the detection of mutations or polymorphisms in other genes. These genes include the APC gene, the CFTR gene, the BRCA1 gene, the BRCA2 gene, the HBB gene, the APOE gene, the PRNP gene, the SCA1 gene, the APP gene, the HPRT gene, the PAX3 gene, the RET gene, the PMP22 gene, the SCN4A gene, and the GNAS1 gene.

Another aspect of the present invention is an isolated and purified nucleic acid fragment comprising nucleic acid having complementarity or identity to a mutation in the ataxia-telangiectasia mutated (ATM) gene, the mutation being selected from the group consisting of:

(1) 10744A>G;
(2) 11482G>A;
(3) IVS3-558A>T;
(4) 146C>G;
(5) 381delA;
(6) IVS8-3delGT
(7) 1028delAAAA
(8) 1120C>T;
(9) 1930ins16
(10) IVS16+2T>C;
(11) 2572T>C;
(12) IVS21+1G>A;
(13) 3085delA;
(14) 3381delTGAC;
(15) 3602delTT;
(16) 4052delT;
(17) 4396C>T;
(18) 5188C>T;
(19) 5290delC;
(20) 5546delT;
(21) 5791G>CCT;
(22) 6047A>G;
(23) IVS44-1G>T;
(24) 6672delGC/6677delTACG;
(25) 6736del11/6749del7;
(26) 7159insAGCC;
(27) 7671delGTTT;
(28) 7705del14
(29) 7865C>T;
(30) 7979delTGT;
(31) 8177C>T;
(32) 8545C>T;
(33) 8565T>A;
(34) IVS64+1G>T; and
(35) 9010del28.

Yet another aspect of the present invention is an isolated and purified nucleic acid fragment comprising nucleic acid having complementarity or identity to a polymorphism or SNP in the ataxia-telangiectasia mutated (ATM) gene, the polymorphism being selected from the group consisting of:

(1) 10807A>G;
(2) IVS3-122T>C;
(3) IVS6+70delT;
(4) IVS16-34C>A;
(5) IVS22-77T>C;
(6) IVS24-9delT;
(7) IVS25-13delA;
(8) 5557G>A;
(9) IVS48-69insATT; and
(10) IVS62-55T>C.

These polymorphisms are relatively common polymorphisms.

Yet another aspect of the present invention is an isolated and purified nucleic acid fragment comprising nucleic acid having complementarity or identity to a polymorphism in the ataxia-telangiectasia mutated (ATM) gene, the polymorphism being selected from the group consisting of:
(1) 10677G>C;
(2) 10742G>T;
(3) 10819G>T;
(4) 10948A>G;
(5) IVS3-300G>A;
(6) IVS8-24del5;
(7) IVS13-137T>C;
(8) IVS14-55T>G;
(9) 1986T>C;
(10) IVS20+27delT;
(11) IVS23-76T>C;
(12) IVS25-35T>A;
(13) IVS27-65T>C;
(14) IVS30-54T>C;
(15) 4362A>C;
(16) IVS38-8T>C;
(17) 5793T>C;
(18) IVS47-11G>T;
(19) IVS49-16T>A;
(20) IVS53+34insA;
(21) IVS60-50 delTTAGTT;
(22) IVS62+8A>C;
(23) IVS62-65G>A; and
(24) 9200C>G.

These are relatively rare polymorphisms.

Another aspect of the present invention is a method for testing a DNA sample of a human for the presence or absence of a mutation or polymorphism in the ATM gene comprising the steps of:
(1) providing a sample of DNA from a human; and
(2) testing the sample for the presence of a mutation or a polymorphism in the ATM gene, the mutation or the polymorphism being one of the mutations or polymorphisms described above.

Yet another aspect of the present invention is an isolated and purified protein, polypeptide, or peptide encoded by a polynucleotide that comprises one of the fragments described above.

Still another aspect of the present invention is an antibody that specifically binds the isolated and purified protein, polypeptide, or peptide.

Another aspect of the present invention is a transgenic mammal all of whose germ cells and somatic cells contain the fragment described above introduced into the mammal or an ancestor of the mammal at an embryonic stage. Typically, the transgenic mammal is a mouse.

BRIEF DESCRIPTION OF THE DRAWINGS

These and other features, aspects, and advantages of the present invention will become better understood with reference to the following description, appended claims, and accompanying drawings where:

DESCRIPTION

Definitions

Figure 1:
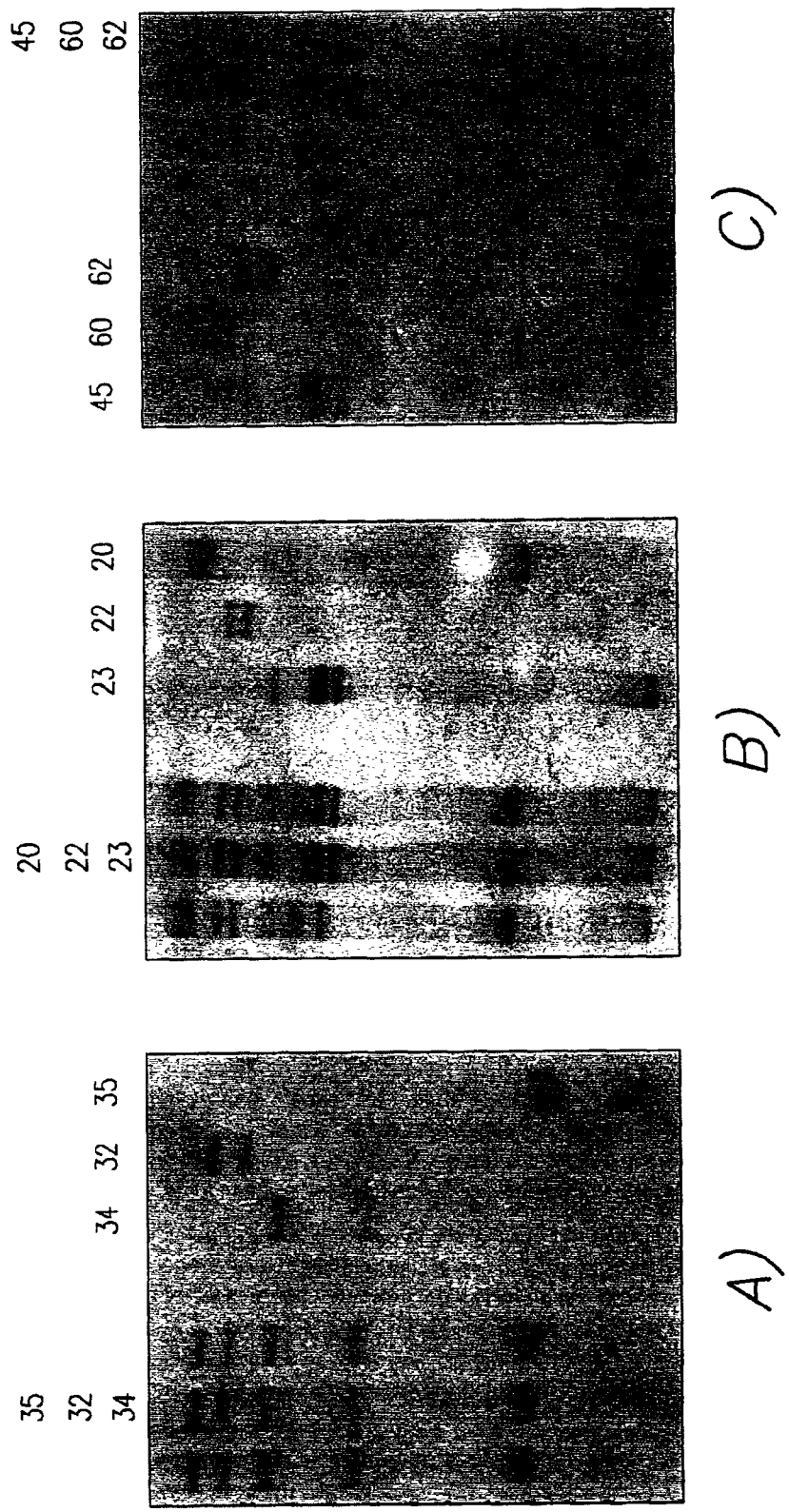
FIG. 1 is an electropherogram showing the results of sequential loading of three sets of ATM PCR fragments, demonstrating no overlap of SSCP patterns; from left to right: A), exons 34, 32, and 35; B), exons 23, 22, and 20; C), exons 45, 60, and 62; by way of example, the loading times for the three sets of PCR products shown in A) were t=0, exon 34; t=45 min, exon 32; t=75 min, exon 35.

As used herein, the terms defined below have the following meanings unless otherwise indicated:

"Nucleic Acid Sequence": the term "nucleic acid sequence" includes both DNA and RNA unless otherwise specified, and, unless otherwise specified, includes both double-stranded and single-stranded nucleic acids. Also included are hybrids such as DNA-RNA hybrids. In particular, a reference to DNA includes RNA that has either the equivalent base sequence except for the substitution of uracil in RNA for thymine in DNA, or has a complementary base sequence except for the substitution of uracil for thymine, complementarity being determined according to the Watson-Crick base pairing rules. Reference to nucleic acid sequences can also include modified bases as long as the modifications do not significantly interfere either with binding of a ligand such as a protein by the nucleic acid or with Watson-Crick base pairing. Reference to nucleic acid sequences also can include nucleic acid sequences that are conjugated or linked covalently or noncovalently to other chemical moieties such as proteins, fluorescers, or other labels as long as the other chemical moieties do not significantly interfere either with binding of a ligand by the nucleic acid or with Watson-Crick base pairing as appropriate for the particular nucleic acid sequence. Reference to nucleic acid sequences also includes the complementary nucleic acid sequence according to the Watson-Crick base pairing rules unless otherwise specified.

"Antibody": as used herein the term "antibody" includes both intact antibody molecules of the appropriate specificity, and antibody fragments (including Fab, F(ab'), Fv, and F(ab')$_2$), as well as chemically modified intact antibody molecules and antibody fragments, including hybrid antibodies assembled by in vitro-reassociation of subunits. Also included are single-chain antibody molecules generally denoted by the term sFv and humanized antibodies in which some or all of the originally non-human constant regions are replaced with constant regions originally derived from human antibody sequences. Both polyclonal and monoclonal antibodies are included unless otherwise specified. Additionally included are modified antibodies or antibodies conjugated to labels or other molecules that do not block or alter the binding capacity of the antibody.

Description

One aspect of the present invention is a method for the detection of mutations and polymorphisms in complex, multiexonic eukaryotic genes, such as the ATM gene. Another aspect of the present invention is directed to new mutations and polymorphisms detected in the ATM gene.

I. Methods for Detection of Mutations and Polymorphisms

An improved method for detection of polymorphisms and mutations in large polyexonic eukaryotic genes that encode a large protein molecule, defects in which lead to the existence of autosomal recessive mutations, employs an improvement in the single-stranded conformation polymorphism (SSCP) technique, known as mega-SSCP. This technique employs the use of a gel electrophoresis technique that allows the running of multiple samples in the same gel electrophoresis lane in the single-strand conformation polymorphism technique. Therefore, this allows the screening of a large number of nucleic acid segments.

Although this technique is of general application, it is described specifically with respect to detection of mutations or polymorphisms in the ataxia-telangiectasia (ATM) gene.

As applied to the ATM gene, the method of detecting the mutation or polymorphism comprises the steps of:

(1) amplifying a plurality of nonoverlapping nucleic acid segments from the human ataxia-telangiectasia gene;

(2) subjecting the amplified nonoverlapping nucleic acid segments to single-stranded conformation polymorphism electrophoresis in a number of lanes such that two or three amplified nucleic acid segments are electrophoresed per lane, the electrophoresis of the segments electrophoresed in the same lane being initiated at different times, such that the signals from each amplified nucleic acid segment are distinct in each lane, the time interval between the initiation of electrophoresis for each segment being chosen to ensure that signals resulting from the electrophoresis are distinct from each segment electrophoresed in the same lane; and (3) comparing the signals from the resulting single-stranded polymorphism electrophoresis for each segment in each of the lanes to detect the mutation or polymorphism.

The mutation or polymorphism is detected by observing a difference in the position of the bands. The gel pattern used enables the person performing the assay to reference the pattern back to the matrix of samples electrophoresed to give positive identification of the sample where a difference in mobility signals the existence of a single-stranded conformation polymorphism.

The single-stranded conformation polymorphism technique detects changes in the conformation of single-stranded nucleic acids electrophoresed under nondenaturing conditions. In such conditions, each nucleic acid segment forms a distinct structure determined by the ability of bases to pair with distant bases in the same strand. Mobility is also influenced by the size of the molecule.

Thus, single-stranded conformation polymorphism can detect relatively small differences in structure which are reflected in the mobility of the nucleic acid segments being electrophoresed.

The nucleic acid segments that are amplified can be amplified by standard techniques. The choice of techniques depends on the materials available. If the starting material involved is DNA, the segments are typically amplified by the polymerase chain reaction mechanism (PCR) as described in U.S. Pat. No. 4,683,195 to Mullis and U.S. Pat. No. 4,684,202 to Mullis, incorporated herein by this reference.

This is the method of choice when genomic DNA is available. Conditions for polymerase chain reaction amplification are generally known in the art and need not be described further here. They are described, for example, in M. I. Innis et al., eds., "PCR Protocols: A Guide to Methods and Applications" (Academic Press, San Diego, 1990), incorporated herein by this reference.

Other amplification techniques such as the ligase amplification reaction (LAR) can alternatively be used.

If the starting material available is RNA, typically messenger RNA, the preferred technique is reverse transcriptase-polymerase chain reaction amplification. Basically, this method involves transcribing DNA from RNA using a retroviral reverse transcriptase, and then using the DNA transcribed for amplification according to the polymerase-chain reaction mechanism.

Conditions for electrophoresis can be chosen by one of ordinary skill in the art according to the size of the nucleic acid segments to be electrophoresed. Preferred conditions are described in M. Orita et al., "Detection of Polymorphisms of Human DNA by Gel Electrophoresis as Single-Strand Conformation Polymorphisms," Proc. Natl. Acad. Sci. USA 86: 2766–2770 (1989). Preferably, electrophoresis is performed in a polyacrylamide gel of about 3% to about 7% polyacrylamide, more preferably of about 4% to about 6% polyacrylamide, most preferably of about 5% polyacrylamide. Preferably, the gel is prepared in glycerol. Most preferably, the glycerol concentration is about 10%. Preferably, the gels are run at about 4° C. using a system that maintains a constant temperature and recirculates the buffer. A preferred buffer is 90 mM Tris-borate, pH 8.3, 4 mM EDTA. Preferred running conditions are from about 150 to 250 volts for about 14–16 hours, depending on the size of the analyzed fragments. The polyacrylamide can be replaced with a proprietary gel matrix called "Mutation Detection Enhancement" from FMC Bioproducts.

The nucleic acid segments that have been amplified and electrophoresed can be detected by standard techniques that are well-known to those skilled in the art. A preferred technique is silver staining. A preferred method of silver staining involves rinsing the gel with 10% ethanol for 10 minutes, with 1% nitric acid for three minutes, performing two quick rinses with distilled water for 30 seconds, silver nitrate for 20 minutes, two very quick rinses with distilled water, 2.96% sodium carbonate/0.054% formaldehyde (37%) for developing, and 10% acetic acid for 10 minutes. Other staining techniques can alternatively be used.

If the amplified fragments are larger than about 350 base pairs, they are typically cleaved with a restriction endonuclease that cleaves the amplified products into fragments that are less than about 350 bases. The restriction endonuclease can be chosen depending on the sequence to be cleaved and the frequency of cleavage required. Suitable restriction endonucleases for use in cleaving amplified fragments are known in the art and are described, for example, in J. Sambrook et al., "Molecular Cloning: A Laboratory Manual" (2d ed., Cold Spring Harbor Laboratory Press, Cold Spring Harbor, N.Y., 1989), vol. 1, pp. 5.3–5.9, incorporated herein by this reference. Such restriction endonucleases recognize sequences of four or more bases appearing in the amplified fragments and cleave at a defined point. Generally, the defined point is within the recognized sequence, but, in some cases, the defined point can be outside of the recognized sequence. Many enzymes recognize palindromic sequences of from 4 to 8 bases. The cleavage points and the lengths of the resulting products can be predicted from the sequence of the nucleic acid and from the known specificity of the enzyme to be used for cleavage.

Typically, the electrophoresis is performed in a plurality of gels so that the step of comparing the signals resulting from the electrophoresis of the amplified nucleic acid segments can detect mutations or polymorphisms in a plurality of segments of the gene.

Typically, for detection of mutations or polymorphisms in the ATM gene on two persons, three gels are used and a total of 70 segments are amplified and electrophoresed using the single-stranded conformation polymorphism technique.

For the ATM gene the primers that are preferred to be used are as shown in Table 1, below:

TABLE 1

| Fragment | Forward | Reverse |
|---|---|---|
| Promoter 1 | 5'-TCCGCGCTTACCCAATA-3' (SEQ ID NO: 3) | 5'-ATGGCCAGCGACTTAGC-3' (SEQ ID NO: 4) |
| Promoter 2 | 5'-AAGAGGGTGGGTGAGAG-3' (SEQ ID NO: 5) | 5'-CACTCGGAAGGTCAAAG-3' (SEQ ID NO: 6) |
| Exon 1a | 5'-CGACGGGCCGAATGTTTGG-3' (SEQ ID NO: 7) | 5'-AGGAGAGGGAGGAGTCAAGG-3' (SEQ ID NO: 8) |
| Exon 1b | 5'-CCTCTCCTCACTCCATCT-3' (SEQ ID NO: 9) | 5'-CTTCCGTTATGACTGTTTCG-3' (SEQ ID NO: 10) |
| Exon 2 | 5'-CGAAACAGTCATAACGGAAG-3' (SEQ ID NO: 11) | 5'-GATAAAAGGAAAAACAATACTA-3' (SEQ ID NO: 12) |
| Exon 3 | 5'-GTTTATCTAAAATGATTCTCTC-3' (SEQ ID NO: 13) | 5'-GATGCAAACAATATTTACTACT-3' (SEQ ID NO: 14) |
| Intron 3a | 5'-CTCTGATAACCTCCTACTT-3' (SEQ ID NO: 15) | 5'-GAATAGAAAACAGCCAGGTA-3' (SEQ ID NO: 16) |
| Intron 3b | 5'-AATGTTAAATCCTTGAGTGCT-3' (SEQ ID NO: 17) | 5'-CACAAAAATGTTTGCCTTGCT-3' (SEQ ID NO: 18) |
| Exon 4 | 5'-TTAATCCTGCTACTACTGC-3' (SEQ ID NO: 19) | 5'-TGAAAATAAAAAGGAAATAATGG-3' (SEQ ID NO: 20) |
| Exon 5 | 5'-CAGAACGAAAGGTAGTAAATT-3' (SEQ ID NO: 21) | 5'-ATATATAGGAAGCAAAGATAAATG-3' (SEQ ID NO: 22) |
| Exon 6 | 5'-GTAATCTAAGCAAGGTGGT-3' (SEQ ID NO: 23) | 5'-GTACTTACACTCAACTTTTATCTT-3' (SEQ ID NO: 24) |
| Exon 7 | 5'-GCCATTCCAAGTGTCTTA-3' (SEQ ID NO: 25) | 5'-TCACAAACAACAACCTTCA-3' (SEQ ID NO: 26) |
| Exon 8 | 5'-AAATCCTTTTTCTGTATGGG-3' (SEQ ID NO: 27) | 5'-TACTGAGTCTAAAACATGGTCT-3' (SEQ ID NO: 28) |
| Exon 9 | 5'-AGTGTGAAGTAATGCTGTGAT-3' (SEQ ID NO: 29) | 5'-TCAACCAGAGAAATCCAGAG-3' (SEQ ID NO: 30) |
| Exon 10 | 5'-CCAGGTGTCTTCTAACG-3' (SEQ ID NO: 31) | 5'-TTATAGGCTTTTTGTGAGAAC-3' (SEQ ID NO: 32) |
| Exon 11 | 5'-GGTTGTGGTGATACGAG-3' (SEQ ID NO: 33) | 5'-CTGGTTGAGATGAAAGGAT-3' (SEQ ID NO: 34) |
| Exon 12 | 5'-GTACTATGGAAATGATGGTG-3' (SEQ ID NO: 35) | 5'-CAGGGATATGTGAGTGTG-3' (SEQ ID NO: 36) |
| Exon 13 | 5'-GGCACTGTCCTGATAGAT-3' (SEQ ID NO: 37) | 5'-GCATCAAATAAGTGGAGA-3' (SEQ ID NO: 38) |
| Exon 14 | 5'-CAATGGTTGTCCTCCTTAA-3' (SEQ ID NO: 39) | 5'-AGATGCAGCTACTACCC-3' (SEQ ID NO: 40) |
| Exon 15 | 5'-GTCCGAAGAAGAGAAGC-3' (SEQ ID NO: 41) | 5'-CTATTTCTCCTTCCTAACAG-3' (SEQ ID NO: 42) |
| Exon 16 | 5'-GTTCTTACAAAAGATAGAGT-3' (SEQ ID NO: 43) | 5'-GTCTTCCAAACAAATGTAAT-3' (SEQ ID NO: 44) |
| Exon 17 | 5'-GTACACTGTAAAAAGCAATAC-3' (SEQ ID NO: 45) | 5'-GAGGTCAAGGCTACAATG-3' (SEQ ID NO: 46) |
| Exon 18 | 5'-ACATTCCATTCAAGATAGAGA-3' (SEQ ID NO: 47) | 5'-GCTATATGTTGTGAGATGC-3' (SEQ ID NO: 48) |
| Exon 19 | 5'-AAATTTTGACTACAGCATGCT-3' (SEQ ID NO: 49) | 5'-CCTCTTATACTGCCAAATC-3' (SEQ ID NO: 50) |
| Exon 20 | 5'-ACTATAATTTTGCTTTTCATATACT-3' (SEQ ID NO: 51) | 5'-CATTTAGTCAGCAACATCAG-3' (SEQ ID NO: 52) |
| Exon 21 | 5'-TTAAAGTAAATGATTTGTGGAT-3' (SEQ ID NO: 53) | 5'-CTTAACAGAACACATCAGT-3' (SEQ ID NO: 54) |

TABLE 1-continued

| Fragment | Forward | Reverse |
|---|---|---|
| Exon 22 | 5'-CTGAAACCACTATCGTAAGA-3'<br>(SEQ ID NO: 55) | 5'-TTGCATTCGTATCCACAGA-3'<br>(SEQ ID NO: 56) |
| Exon 23 | 5'-AAAGACATATTGGAAGTAACTTA-3'<br>(SEQ ID NO: 57) | 5'-AGCCTACGGGAAAAGAACT-3'<br>(SEQ ID NO: 58) |
| Exon 24 | 5'-AGTAAGATCTCCATTGAAAATTT-3'<br>(SEQ ID NO: 59) | 5'-CATTCTACTGCCATCTGC-3'<br>(SEQ ID NO: 60) |
| Exon 25 | 5'-GTGATTTATTTTGTTCTGGAATA-3'<br>(SEQ ID NO: 61) | 5'-CATACAGTTGTTTTAGAGCAG-3'<br>(SEQ ID NO: 62) |
| Exon 26 | 5'-TGGAGTTCAGTTTGGGATTT-3'<br>(SEQ ID NO: 63) | 5'-GTGCCACTCAGAAAATCTA-3'<br>(SEQ ID NO: 64) |
| Exon 27 | 5'-AAGAAAAGTTGAATGAATGTTGTT-3'<br>(SEQ ID NO: 65) | 5'-TGTGTATGGGTATGGTATG-3'<br>(SEQ ID NO: 66) |
| Exon 28 | 5'-GATACTTTAATGCTGATGGTA-3'<br>(SEQ ID NO: 67) | 5'-CGAATAAATCGAATAAATAGCC-3'<br>(SEQ ID NO: 68) |
| Exon 29 | 5'-GTCATCGAATACTTTTGGAAA-3'<br>(SEQ ID NO: 69) | 5'-CTCAATTCAAAGGTGGCTAT-3'<br>(SEQ ID NO: 70) |
| Exon 30 | 5'-CATTTTGGAAGTTCACTGG-3'<br>(SEQ ID NO: 71) | 5'-CCTCTTTAAGATGTATTTACAA-3'<br>(SEQ ID NO: 72) |
| Exon 31 | 5'-ATATCAAACCCAAATCTAAATTCT-3'<br>(SEQ ID NO: 73) | 5'-AAAAAACAGGAAGAACAGGAT-3'<br>(SEQ ID NO: 74) |
| Exon 32 | 5'-AGATGCTGAACAAAAGGACT-3'<br>(SEQ ID NO: 75) | 5'-AACACTCAAATCCTTCTAACA-3'<br>(SEQ ID NO: 76) |
| Exon 33 | 5'-GTTTTGTTGGCTTACTTT-3'<br>(SEQ ID NO: 77) | 5'-GAGCATTACAGATTTTTG-3'<br>(SEQ ID NO: 78) |
| Exon 34 | 5'-GTCTATAAATGGCACTTAACT-3'<br>(SEQ ID NO: 79) | 5'-TGACAATGAAACCAAGAGC-3'<br>(SEQ ID NO: 80) |
| Exon 35 | 5'-CAATTATAAACAAAAGTGTTGTCT-3'<br>(SEQ ID NO: 81) | 5'-ACTACAGGCAACAGAAAACA-3'<br>(SEQ ID NO: 82) |
| Exon 36 | 5'-TGAAGTACAGAAAAACAGCAT-3'<br>(SEQ ID NO: 83) | 5'-GTGTGAAGTATCATTCTCCAT-3'<br>(SEQ ID NO: 84) |
| Exon 37 | 5'-GGTGTACTTGATAGGCATTT-3'<br>(SEQ ID NO: 85) | 5'-TGTTTTAGATATGCTGGG-3'<br>(SEQ ID NO: 86) |
| Exon 38 | 5'-TACAATGATTTCCACTTCTCT-3'<br>(SEQ ID NO: 87) | 5'-TATTATGTGAAGATGATGTGC-3'<br>(SEQ ID NO: 88) |
| Exon 39 | 5'-TCATTTTTACTCAAACTATTG-3'<br>(SEQ ID NO: 89) | 5'-CCATCTTAAATCCATCTTTCT-3'<br>(SEQ ID NO: 90) |
| Exon 40 | 5'-TTATAGCATAGTGGGAGACA-3'<br>(SEQ ID NO: 91) | 5'-TTTGCAACACCTTCACCTAA-3'<br>(SEQ ID NO: 92) |
| Exon 41 | 5'-TAAGCAGTCACTACCATTGTA-3'<br>(SEQ ID NO: 93) | 5'-TATACCCTTATTGAGACAATGC-3'<br>(SEQ ID NO: 94) |
| Exon 42 | 5'-GTATTCAGGAGCTTC-3'<br>(SEQ ID NO: 95) | 5'-ATGGCATCTGTACAGTGTCT-3'<br>(SEQ ID NO: 96) |
| Exon 43 | 5'-TTGTTGTTTCCATGTTTTCAGG-3'<br>(SEQ ID NO: 97) | 5'-TGCTTCGTGTTCATATGTTCG-3'<br>(SEQ ID NO: 98) |
| Exon 44 | 5'-GTGGTGGAGGGAAGATGTTA-3'<br>(SEQ ID NO: 99) | 5'-CTGAAATAACCTCAGCACTACA-3'<br>(SEQ ID NO: 100) |
| Exon 45 | 5'-TGTATCTTTGCTGTTTTTTTC-3'<br>(SEQ ID NO: 101) | 5'-CAGTTGTTGTTTAGAATGAG-3'<br>(SEQ ID NO: 102) |
| Exon 46 | 5'-CATGTATATCTTAGGGTTCTG-3'<br>(SEQ ID NO: 103) | 5'-CTTCATCAATGCAAATCCTTACA-3'<br>(SEQ ID NO: 104) |

TABLE 1-continued

| Fragment | Forward | Reverse |
|---|---|---|
| Exon 47 | 5'-CAAAGCCTATGATGAGAAC-3' (SEQ ID NO: 105) | 5'-CCCACTTCAGCCTTCTAAA-3' (SEQ ID NO: 106) |
| Exon 48 | 5'-TTTTTCATTTCTCTTGCTTACAT-3' (SEQ ID NO: 107) | 5'-GACATTTCTTTTTCCCTCAG-3' (SEQ ID NO: 108) |
| Exon 49 | 5'-GGTAGTTGCTGCTTTCATT-3' (SEQ ID NO: 109) | 5'-AAATTACTAATTTCAAGGCTCTA-3' (SEQ ID NO: 110) |
| Exon 50 | 5'-ACATTTTTAACCTGCTTTTTTCC-3' (SEQ ID NO: 111) | 5'-CCATACTTTTCTTTGCTTTGGAA-3' (SEQ ID NO: 112) |
| Exon 51 | 5'-CCTTAATTTGAGTGATTCTTTAG-3' (SEQ ID NO: 113) | 5'-ATGCAAAAACACTCACTCAG-3' (SEQ ID NO: 114) |
| Exon 52 | 5'-AGTTCATGGCTTTTGTGTTTT-3' (SEQ ID NO: 115) | 5'-GTATACACGATTCCTGACAT-3' (SEQ ID NO: 116) |
| Exon 53 | 5'-TAGTTAGTGAAGTTTTGTTAAC-3' (SEQ ID NO: 117) | 5'-TTTGTATTTCCATTTCTTAG-3' (SEQ ID NO: 118) |
| Exon 54 | 5'-AAGCAAAATGAAAAATATGG-3' (SEQ ID NO: 119) | 5'-GGAAAGACTGAATATCACAC-3' (SEQ ID NO: 120) |
| Exon 55 | 5'-GAAGTTTAAATGTTGGGTAG-3' (SEQ ID NO: 121) | 5'-AGCAGATTTACTTATTAGGC-3' (SEQ ID NO: 122) |
| Exon 56 | 5'-GTGGTATCTGCTGACTATTC-3' (SEQ ID NO: 123) | 5'-ACCAATTTTGACCTACATAA-3' (SEQ ID NO: 124) |
| Exon 57 | 5'-GTTCTTAACCACTATCACATCGTC-3' (SEQ ID NO: 125) | 5'-CATTTCTACTCTACAAATCTTCCTCAT-3' (SEQ ID NO: 126) |
| Exon 58 | 5'-TTGGTTTGAGTGCCCTTTGC-3' (SEQ ID NO: 127) | 5'-TTCACCCAACCAAATGGCAT-3' (SEQ ID NO: 128) |
| Exon 59 | 5'-TCAAATGCTCTTTAATGG-3' (SEQ ID NO: 129) | 5'-CAGCTGTCAGCTTTAATAAGCC-3' (SEQ ID NO: 130) |
| Exon 60 | 5'-TCCTGTTCATCTTTATTGCCCC-3' (SEQ ID NO: 131) | 5'-GCCAAACAACAAAGTGCTCAA-3' (SEQ ID NO: 132) |
| Exon 61 | 5'-GTGATTTCAGATTGTTTGT-3' (SEQ ID NO: 133) | 5'-ATGATGACCAAATATTTACT-3' (SEQ ID NO: 134) |
| Exon 62 | 5'-TGTGGTTTCTTGCCTTTGT-3' (SEQ ID NO: 135) | 5'-CCAGCCCATGTAATTTTGA-3' (SEQ ID NO: 136) |
| Exon 63 | 5'-CTCTGCCAAGTATTATGCTATTT-3' (SEQ ID NO: 137) | 5'-GACTTCCTGACGAGATACACA-3' (SEQ ID NO: 138) |
| Exon 64 | 5'-TGTTTCTAAGTATGTGATT-3' (SEQ ID NO: 139) | 5'-CACTAAGGACAAAAACACAAAGGT-3' (SEQ ID NO: 140) |
| Exon 65 | 5'-TTAAACTGTTCACCTCACT-3' (SEQ ID NO: 141) | 5'-GGCAGGTTAAAAATAAAGG-3' (SEQ ID NO: 142) |

The primers that amplify the exons also provide amplification of the adjoining intervening sequences (introns).

Other segments can be amplified with other primers.

In mega-SSCP, two or three amplified segments are electrophoresed in the same lane. The segments to be electrophoresed in the same lane are chosen empirically so that their mobilities are sufficiently different so that the signals can be distinguished. These mobilities can be determined by electrophoresing each of the amplified segments individually to determine their mobilities in SSCP.

The methods that are described above with particular reference to the ATM gene, a mutation in which causes the autosomal recessive disorder ataxia-telangiectasia, can be extended to other genes, both human and non-human. In general, such techniques can be applied to detection of a polymorphism in a polyexonic eukaryotic gene of at least 4 kilobase pairs in length. The exact pattern of electrophoresis and the intervals between the start times for each sample are chosen from the sequence of the gene. The segments to be amplified, and in which mutations or polymorphisms can therefore be detected, can include exons, introns, and promoter regions. This technique is of use in detecting genes in which a mutation results in the presence of an autosomal recessive condition, although it is not limited to such genes, and can be used to detect autosomal dominant mutations as well.

An example of the sequential loading of the amplified segments is shown in FIG. 1. In FIG. 1, in A), amplification products of exons 34, 32, and 35 are loaded; in B), amplification products of exons 23, 22, and 20 are loaded; and in C), amplification products of exons 45, 60, and 62 are loaded. By way of example, the loading times for the three sets of PCR products shown in FIG. 1A were: t=0, exon 34; t=45 min, exon 32; t=75 min, exon 35.

Therefore, generally, the interval over which the segments are loaded ranges from 0 to 75 minutes.

The genes for which such methods are useful include, but are not limited to, the CFTR gene, the APC gene, the BRCA1 gene, the BRCA2 gene, the HBB gene, the APOE gene, the PRNP gene, the SCA1 gene, the APP gene, the HPRT gene, the PAX3 gene, the RET gene, the PMP22 gene, the SCN4A gene, and the GNAS1 gene.

The CFTR gene is a gene in which a defect causes the autosomal recessive disorder cystic fibrosis. The APC gene is a gene in which mutations can cause the autosomal dominant condition familial adenomatous polyposis, in which colonic polyps develop which are likely to become malignant. The BRCA1 and BRCA2 genes are genes in which mutations predispose women to breast cancer. The HBB gene is a gene in which a defect causes the autosomal recessive disorder β-thalassemia. The APOE gene is a gene in which a defect can cause a number of disorders of lipid metabolism, leading, for example, to hypercholesterolemia and atherosclerosis. The PRNP gene is a gene in which a mutation causes Gerstmann-Sträussler-Scheinker syndrome. The HPRT gene is a gene in which mutations can cause gout and/or Lesch-Nyhan syndrome, depending on the severity of the loss of function. The PAX3 gene is a gene in which a loss-of-function mutation causes type 1 Waardenberg syndrome. The RET gene is a gene in which a loss-of-function mutation causes Hirschsprung disease. The PMP22 gene is a gene in which a loss-of-function mutation causes Charcot-Marie-Tooth neuropathy type 1A. The SCN4A gene is a gene in which mutations may cause several diseases, including paramyotonia congenita and hyperkalemic periodic paralysis. The GNAS1 gene is a gene in which mutations also may cause several conditions, including Albright hereditary osteodystrophy and McCune-Albright syndrome. This list is illustrative and is not limiting.

These genes are examples of the genes in which mutations or polymorphisms can be detected by the method of the present invention.

II. Isolated Nucleic Acid Fragments Encoding Mutations or Polymorphisms in the ATM Gene Another aspect of the present invention is an isolated and purified fragment comprising nucleic acid having complementarity or identity to a mutation or to a polymorphism in the ATM gene. The mutation is one of those that is identified by the method described above in Section (I) and is one of those shown in Table 2. The polymorphism is one of those that is also identified by the method described above in Section (I) and is one of those shown in Table 3 (relatively common polymorphisms) or Table 4 (rare polymorphisms). The polymorphisms in Table 3 are relatively common polymorphisms that occur at a frequency of from 14% to 45%. The polymorphisms in Table 4 are relatively rare polymorphisms that occur at a frequency of from 0.5% to 6%.

A fragment according to the present invention that is particularly useful is a fragment that has complementarity to the mutation or to the polymorphism in the ATM gene, is hairpin shaped, is covalently linked to a fluorophore and to a quencher, and has a structure such that the fluorophore is internally quenched by the quencher when the fragment is not base-paired and such that the internal quenching is relieved when the fragment is base-paired, thereby restoring fluorescence of the fluorophore. Such fragments are useful as molecular beacons in detecting the mutations or polymorphisms (S. Tyagi et al., "Multicolor Molecular Beacons for Allele Discrimination," *Nature Biotechnol.* 16: 49–53 (1998)). A particularly suitable quencher is DABCYL (4-[4'-dimethylaminophenylazo]benzoic acid). A large number of suitable fluorophores are known in the art, such as coumarin, EDANS, fluorescein, Lucifer yellow, BODIPY, tetramethylrhodamine, and Texas red. Further details on the methods are described in S. Tyagi et al. (1998), supra, incorporated herein by this reference.

Another fragment according to the present invention that is particularly useful is a fragment that is DNA, that has complementarity to the mutation or to the polymorphism in the ATM gene and that has covalently linked to either its 5'-end or to its 3'-end a segment of about 40 bases, the segment of about 40 bases comprising a repeating unit of dCdG or dGdC. This fragment is useful as a primer that generates a GC clamp on amplification by a procedure such as PCR. The resulting amplification product or amplicon has a sequence of dGdC in one strand and a sequence of dCdG in the other strand, thus generating a region of exceptional stability to thermal denaturation by tethering one end. This increases the overall melting range of the DNA molecule. This is particularly useful for denaturing high performance liquid chromatography.

III. Methods of Testing DNA

Another aspect of the present invention is a method of testing a DNA sample for the presence of a mutation or polymorphism in the ATM gene. The mutation or polymorphism is one of those that is identified by the method described above in Section (I) and is one of those shown in Table 2, Table 3 or Table 4.

In general, the method comprises:

(1) providing a sample of DNA from a human; and
(2) testing the sample for the presence or absence of the mutation or polymorphism in the ATM gene.

Preferably, the step of testing the sample for the presence or absence of the mutation comprises PCR amplifying one of the exons, introns, or control regions listed in Table I with the corresponding primers and subjecting the PCR products to heteroduplex analysis to detect the presence or absence of the mutation. Methods for performing heteroduplex analysis are well known in the art and are described, for example, in J. Keen et al., *Trends Genet.* 7:5 (1991). Heteroduplex analysis is typically combined with SSCP.

Typically, the DNA sample comprises genomic DNA. It is also possible to test nongenomic DNA such as cDNA prepared by reverse transcription of RNA such as mRNA, but such DNA lacks exons and thus it is not possible to detect mutations in exons in such DNA samples.

In particular, the following mutations in the ATM gene are subject to detection with the following combinations of primers:

(1) The mutation 10744A>G, with a primer set selected from the group consisting of either TCCGCGCTTAC-CCAATA (SEQ ID NO: 3) and ATGGCCAGCGACTTAGC (SEQ ID NO: 4) or AAGAGGGTGGGTGAGAG (SEQ ID NO: 5) and CACTCGGAAGGTCAAAG (SEQ ID NO: 6).

(2) The mutation 11482G>A, with the primer set CCTCTCCTCACTCCATCT (SEQ ID NO: 9) and CTTC-CGTTATGACTGTTTCG (SEQ ID NO: 10).

(3) The mutation IVS3-558A>T, with a primer set selected from the group consisting of either CTCT-GATAACCTCCTACTT (SEQ ID NO: 15) and GAATA-GAAAACAGCCAGGTA (SEQ ID NO: 16) or AATGT-TAAATCCTTGAGTGCT (SEQ ID NO: 17) and CACAAAAATGTTTGCCTTGCT (SEQ ID NO: 18).

(4) The mutation 146C>G, with the primer set CAGAAC-GAAAGGTAGTAAATT (SEQ ID NO: 21) and ATATAT-AGGAAGCAAAGATAAATG (SEQ ID NO: 22).

(5) The mutation 381delA, with the primer set GCCAT-TCCAAGTGTCTTA (SEQ ID NO: 25) and TCACAAA-CAACAACCTT (SEQ ID NO: 26).

(6) The mutation IVS8-3delGT, with the primer set AAATCCTTTTTCTGTATGGG (SEQ ID NO: 27) and TACTGAGTCTAAAACATGGTCT (SEQ ID NO: 28).

(7) The mutation 1028delAAAA, with the primer set CCAGGTGTCTTCTAACG (SEQ ID NO: 31) and TTAT-AGGCTTTTTGTGAGAAC (SEQ ID NO: 32).

(8) The mutation 1120C>T, with the primer set GGT-TGTGGTGATACGAG (SEQ ID NO: 33) and CTGGT-TGAGATGAAAGGAT (SEQ ID NO: 34).

(9) The mutation 1930ins16, with the primer set GTC-CGAAGAAGAGAAGC (SEQ ID NO: 41) and CTATTTCTCCTTCCTAACAG (SEQ ID NO: 42).

(10) The mutation IVS16+2T>C, with the primer set GTTCTTACAAAAGATAGAGT (SEQ ID NO: 43) and GTCTTCCAAACAAATGTAAT (SEQ ID NO: 44).

(11) The mutation 2572T>C, with the primer set AAATTTTGACTACAGCATGCT (SEQ ID NO: 49) and CCTCTTATACTGCCAAATC (SEQ ID NO: 50).

(12) The mutation IVS21+1G>A, with the primer set TTAAAGTAAATGATTTGTGGAT (SEQ ID NO: 53) and CTTAACAGAACACATCAGT (SEQ ID NO: 54).

(13) The mutation 3085delA, with the primer set AAA-GACATATTGGAAGTAACTTA (SEQ ID NO: 57) and AGCCTACGGGAAAAGAACT (SEQ ID NO: 58).

(14) The mutation 3381delTCAG, with the primer set GTGATTTATTTTGTTCTGGAATA (SEQ ID NO: 61) and CATACAGTTGTTTTAGAGCAG (SEQ ID NO: 62).

(15) The mutation 3602delTT, with the primer set AAGAAAAGTTGAATGAATGTTGTT (SEQ ID NO: 65) and TGTGTATGGGTATGGTATG (SEQ ID NO: 66).

(16) The mutation 4052delT, with the primer set GTCATCGAATACTTTTGGAAA (SEQ ID NO: 69) and CTCAATTCAAAGGTGGCTAT (SEQ ID NO: 70).

(17) The mutation 4396C>T, with the primer set ATAT-CAAACCCAAATCTAAATTCT (SEQ ID NO: 73) and AAAAAACAGGAAGAACAGGAT (SEQ ID NO: 74).

(18) The mutation 5188C>T, with the primer set GGTG-TACTTGATAGGCATTT (SEQ ID NO: 85) and TGTTT-TAGATATGCTGGG (SEQ ID NO: 86).

(19) The mutation 5290delC, with the primer set GGT-GTACTTGATAGGCATTT (SEQ ID NO: 85) and TGTTT-TAGATATGCTGGG (SEQ ID NO: 86).

(20) The mutation 5549delT, with the primer set TCATTTTTACTCAAACTATTG (SEQ ID NO: 89) and CCATCTTAAATCCATCTTTCT (SEQ ID NO: 90).

(21) The mutation 5791G>CCT, with the primer set TAAGCAGTCACTACCATTGTA (SEQ ID NO: 93) and TATACCCTTATTGAGACAATGC (SEQ ID NO: 94).

(22) The mutation 6047A>G, with the primer set TTGT-TGTTTCCATGTTTTCAGG (SEQ ID NO: 97) and TGCT-TCGTGTTCATATGTTCG (SEQ ID NO: 98).

(23) The mutation IVS44-1G>T, with the primer set GTGGTGGAGGGAAGATGTTA (SEQ ID NO: 99) and CTGAAATAACCTCAGCACTACA (SEQ ID NO: 100).

(24) The mutation 6672delGG/6677delTACG, with the primer set TTTTTCATTTCTCTTGCTTACAT (SEQ ID NO: 107) and GACATTTCTTTTTCCCTCAG (SEQ ID NO: 108).

(25) The mutation 6736del 11/6749del7, with the primer set TTTTTCATTTCTCTTGCTTACAT (SEQ ID NO: 107) and GACATTTCTTTTTCCCTCAG (SEQ ID NO: 108).

(26) The mutation 7159insAGCC, with the primer set CCTTAATTTGAGTGATTCTTTAG (SEQ ID NO: 113) and ATGCAAAAACACTCACTCAG (SEQ ID NO: 114).

(27) The mutation 7671delGTTT, with the primer set AAGCAAAATGAAAAATATGG (SEQ ID NO: 119) and GGAAAGACTGAATATCACAC (SEQ ID NO: 120).

(28) The mutation 7705del14, with the primer set AAG-CAAAATGAAAAATATGG (SEQ ID NO: 119) and GGAAAGACTGAATATCACAC (SEQ ID NO: 120).

(29) The mutation 7865C>T, with the primer set GAAGTTTAAATGTTGGGTAG (SEQ ID NO: 121) and AGCAGATTTACTTATTAGGC (SEQ ID NO: 122).

(30) The mutation 7989delTGT, with the primer set GTGGTATCTGCTGACTATTC (SEQ ID NO: 123) and ACCAATTTTGACCTACATAA (SEQ ID NO: 124).

(31) The mutation 8177C>T, with the primer set TTG-GTTTGAGTGCCCTTTGC (SEQ ID NO: 127) and TTCACCCAACCAAATGGCAT (SEQ ID NO: 128).

(32) The mutation 8545C>T, with the primer set TCCT-GTTCATCTTTATTGCCCC (SEQ ID NO: 131) and GCCAAACAACAAAGTGCTCAA (SEQ ID NO: 132).

(33) The mutation 8565T>A, with the primer set TCCT-GTTCATCTTTATTGCCCC (SEQ ID NO: 131) and GCCAAACAACAAAGTGCTCAA (SEQ ID NO: 132).

(34) The mutation IVS64+1G>T, with the primer set TGTTTCTAAGTATGTGATT (SEQ ID NO: 139) and CACTAAGGACAAAAACACAAAGGT (SEQ ID NO: 140).

(35) The mutation 9010del28, with the primer set TTAAACTGTTCACCTCACT (SEQ ID NO: 141) and GGCAGGTTAAAAATAAAGG (SEQ ID NO: 142).

Other mutations and polymorphisms can be detected using appropriate primer sets that cover the region of the mutation or polymorphism for its amplification.

The mutations and polymorphisms in the ATM gene that are an aspect of the present invention are particularly useful for interpretation in conjunction with automated high-density oligonucleotide probes mounted on solid supports, sometimes referred to as "DNA chips," as described in J. C. Hacia et al., "Strategies for Mutational Analysis of the Large Multiexon ATM Gene using High-Density Oligonucleotide Arrays," *Genome Res.* 8: 1245–1258 (1998).

IV. Isolated Protein, Polypeptide, or Peptide Products

Another aspect of the present invention is an isolated and purified protein, polypeptide, or peptide encoded by a polynucleotide that comprises one of the fragments listed above in Table 2, Table 3, or Table 4.

Such proteins, polypeptides, or peptides can be produced by incorporating the polynucleotide in a suitable vector operably linked to and under the control of one or more control sequences such as promoters, operators, and enhancers, introducing the vector into a suitable compatible host in which the protein, polypeptide, or peptide could be expressed, expressing the protein, polypeptide, or peptide, and isolating the protein, polypeptide, or peptide.

Such proteins, polypeptides, or peptides can also be produced by determining the sequence of the encoded protein, polypeptide, or peptide by the standard triplet genetic code and then directly synthesizing the protein, polypeptide, or peptide, such as by standard solid-phase synthesis methods.

V. Antibodies

Another aspect of the present invention is antibodies that specifically bind the proteins, polypeptides, or peptides of Section (IV). These antibodies can be prepared by standard methods. The proteins and the larger polypeptides and peptides can be used directly as immunogens, while, for the shorter peptides, it is generally preferred to couple them to a protein carrier such as keyhole limpet hemocyanin for immunization.

The antibodies can be polyclonal or monoclonal. Monoclonal antibodies can be prepared by standard methods once antibody-producing animals have been immunized with the proteins or polypeptides, or with the peptides coupled to appropriate protein carriers.

VI. Transgenic Animals

Another aspect of the present invention is transgenic animals. In transgenic animals according to the present invention, all of the germ cells and the somatic cells of the animal contain one of the fragments of Section (II) introduced into the animal, or into an ancestor of the animal, at an embryonic stage. Preferably, the transgenic animal is a mouse, although other animals, such as rats, pigs, and sheep, can also be used.

Transgenic animals according to the present invention are useful in determining the effects of the mutations in the fragments on the development of the organisms in which they are incorporated.

The invention is illustrated by the following Examples. These Examples are for illustrative purposes only and are not intended to limit the invention.

EXAMPLES

Example 1

Detection of Mutations and Polymorphisms in the ATM Gene by Mega-SSCP

Patients and Methods

Patients

Ninety-two unrelated A-T patients from different populations (American, Turkish, Polish, Costa Rican, Canadian, and Spanish) were screened. In most of the cases DNA was the only biological material available from these patients. In a few samples, previous screening by PTT (M. Telatar et al., "Ataxia-Telangiectasia: Mutations in ATM cDNA Detected by Protein-Truncation Screening," *Am J Hum Genet.* 59:40–44 (1996)) had failed to identify both mutations. In some experiments, DNA from 40 unrelated individuals (80 independent chromosomes) was used to screen for and determine the allelic frequency of specific polymorphisms.

Optimized Single-strand Conformation Polymorphism (SSCP) Technique

An SSCP technique described previously by Orita et al. (M. Orita et al. "Detection of Polymorphisms of Human DNA by Gel Electrophoresis as Single-Strand Conformation Polymorphisms," *Proc. Natl. Acad. Sci. USA* 86:2766–2770 (1989)) was optimized. Genomic DNA from 92 A-T patients and a normal individual was PCR-amplified for 70 different regions, including the 66 ATM exons (with additional 50–100 hp of flanking intronic sequence), the promoter region upstream of the first exon (P. J. Byrd et al., "Mutations Revealed by Sequencing the 5' Half of the Gene for Ataxiatelangiectasia," *Hum. Mol. Genet.* 5:145–149 (1996)), and a putative promoter region within intron 3 (M. Platzer et al., "Ataxia-Telangiectasia Locus: Sequence Analysis of 184 kb of Human Genomic DNA Containing the Entire ATM Gene," *Genome Res.* 7:592–605 (1997)). If amplified products were larger than 350 hp they were digested with a suitable restriction enzyme before being analyzed by SSCP.

All regions were analyzed by SSCP using MDE (Mutation Detection Enhancement; FMC Bioproducts) with glycerol as the gel matrix. Gels were run at 4° C. using the D-CODE Universal Mutation Detection System (BIO RAD), which maintains a constant temperature and recirculates the buffer. The running conditions varied between 150–250 V for 14–16 h, depending on the size of the analyzed fragments. Silver staining was used to visualize the SSCP patterns (10% ethanol for 10 min, 1% $HNO_3$ for 3 min, two quick rinses with distilled water for 30 sec, $AgNO_3$ for 20 min, two very quick rinses with distilled water, 2.96% $Na_2CO_3$/0.054% formaldehyde 37% for developing, and 10% acetic acid for 10 min).

Due to the large number of DNA samples and PCR fragments, screening was expedited by sequentially loading 3 different sets of PCR products into the same gel. In order to do so, loading times were pretested and carefully established to keep SSCP patterns from overlapping (FIG. 1). The elapsed times between loading various PCR products ranged from 15 to 120 min. As controls, previously known mutations were used that had been detected by the protein truncation test (Telatar et al. (1996), supra) to optimize the efficiency of SSCP for each PCR fragment.

DNA Sequencing

Once an abnormal pattern could be detected by SSCP, the specific fragment was PCR amplified, purified using a PCR purification column (Qiagen), and sequenced using the Thermo Sequenase Cy5.5 dye terminator sequencing kit (Amersham) and the OpenGene DNA Automated Sequencing System (Visible Genetics).

Primers

Primer sets used for each of the 70 PCR segments analyzed are listed in Table 1, above.

Results

A TM Mutations

Before initiating SSCP screening of the new samples, the optimal conditions for detecting known mutations that had been previously defined in the amplified PCR fragments were determined (Telatar et al. (1996), supra; M. Telatar et al., "Ataxia-Telangiectasia: Identification and Detection of Founder-Effect Mutations in the ATM gene in Ethnic Populations," *Am. J. Hum. Genet.* 62:86–97 (1998) ("Telatar et al. (1998a)"). Abnormal SSCP patterns were observed for all known mutations. A total of 118 of 177 expected mutations were observed as present in the screening (85 non-consanguineous patients with two unknown mutations and 7 non-consanguineous patients with one unknown mutation). Therefore, the efficiency of mutation detection by optimized SSCP was ~70%. Among the detected mutations, 35 have not been previously observed (Table 2).

TABLE 2

New mutations in the ATM gene detected by the SSCP technique.

| Mutation | Localization | Codon change | codon number | Conseque |
|---|---|---|---|---|
| 10744A>G* | Promoter | — | — | ↓express? |
| 11482G>A* | Exon 1b | — | — | ↓express? |
| IVS3-558A>T | IVS 3 promoter | — | — | Disrupts +1 ISS |
| 146C>G | Exon 5 | S>C | 49 | Missense |
| 381de1A | Exon 7 | T>X | 127 | FS, Term |
| IVS8-3delGT | Intron 8 | — | — | Exon 9 skipped? |
| 1028delAAAA | Exon 10 | E>X | 343 | FS, Term |
| 1120C>T | Exon 11 | Q>X | 374 | Term |
| 1930ins16 | Exon 15 | S>X | 644 | FS, Term |
| IVS16 + 2T>C | Intron 16 | — | — | Ex. 16 skipped? |
| 2572T>C | Exon 19 | F>L | 858 | Missense |
| IVS21 + IG>A | Intron 21 | — | — | Ex. 21 skipped? |
| 3085delA | Exon 23 | T>X | 1029 | FS, Term |
| 3381delTCAG | Exon 25 | Q>X | 1127 | FS, Term |

TABLE 2-continued

New mutations in the ATM gene detected by the SSCP technique.

| Mutation | Localization | Codon change | codon number | Conseque |
|---|---|---|---|---|
| 3602delTT | Exon 27 | F>X | 1200 | FS, Term |
| 4052delT | Exon 29 | L>X | 1351 | FS, Term |
| 4396C>T | Exon 31 | R>X | 1466 | Term |
| 5188C>T | Exon 37 | R>X | 1730 | Term |
| 5290delC | Exon 37 | L>X | 1730 | FS, Term |
| 5546delT | Exon 39 | I>X | 1849 | FS, Term |
| 5791G>CCT | Exon 41 | D>X | 1931 | FS, Term |
| 6047A>G | Exon 43 | D>G | 2016 | Missense |
| IVS44-1G>T | Intron 44 | — | — | Ex. 45 skipped? |
| 6672delGG/ 6677delTACG | Exon 48 | M-A-L- R>I-S | 2224 | In-frame deletion |
| 6736del11/ 6749del7 | Exon 48 | C-I-K- D-I-L- T>H | 2246 | In-frame deletion |
| 7159insAGCC | Exon 51 | F>X | 2387 | FS, Term |
| 7671delGTTT | Exon 54 | L>X | 2257? | FS, Term |
| 7705del4 | Exon 54 | D>X | 2569? | FS, Term |
| 7865C>T | Exon 55 | A>V | 2621 | New spl donor |
| 7989delTGT | Exon 56 | — | 2663 | Val deleted |
| 8177C>T | Exon 58 | A>V | 2726 | Missense |
| 8545C>T | Exon 60 | R>X | 2849 | Term |
| 8565T>A | Exon 60 | S>R | 2855 | Missense |
| IVS64 + 1G>T | Intron 64 | — | — | Ex. 64 skipped? |
| 9010del28 | Exon 65 | K>X | 3004 | FS, Term |

*genomic DNA numbering (U82828); FS, frameshift; Term, termination; ISS, initiation start site; spl splicing; Ita, Italian; Pol, Polish; N Am, North American Most of the new mutations corresponded to protein truncating mutations, as previously reported (Telatar et al., (1996), supra; P. Concannon & R. A. Gatti, "Diversity of ATM Gene Mutations in Patients with Ataxia-Telangiectasia," *Hum. Mutat.* 10:100–107 (1997); Telatar et al.(1998a), supra). These had not been detected before because RNA was not available for PTT testing. Mutations causing splicing defects were also found (IVS8-3delGT, IVS16+2T>C, IVS21+G>A, IVS44-1G>T, 7865C>T, IVS64+1G>T), along with missense mutations, some of the latter affecting amino acids that are conserved in both mouse and pufferfish genomes (146C>T, 6047A>G, 8177C>T, 8565T>A); one of them was not conserved (2572T>C). It is interesting to note two in-frame deletions found in two unrelated A-T patients, both homozygous, in exon 48. These complex deletions affected amino acids that are again conserved in the mouse and pufferfish genomes. Since the untranslated and promoter regions of the ATM gene were included in the SSCP screening, the experiments also were able to detect DNA changes in those areas. In the promoter region, detected 10744A>G and 11482G>A were detected in two unrelated compound heterozygotes (i.e., A-T patients); each of these DNA changes could affect the normal expression of the gene. Experiments are in progress to test this possibility. A mutation was also detected at IVS3-558A>T, which disrupts the initiation start site (+1) for the putative promoter in intron 3 reported by Platzer et al. (1997), supra.

Mega-SSCP

Figure 2:
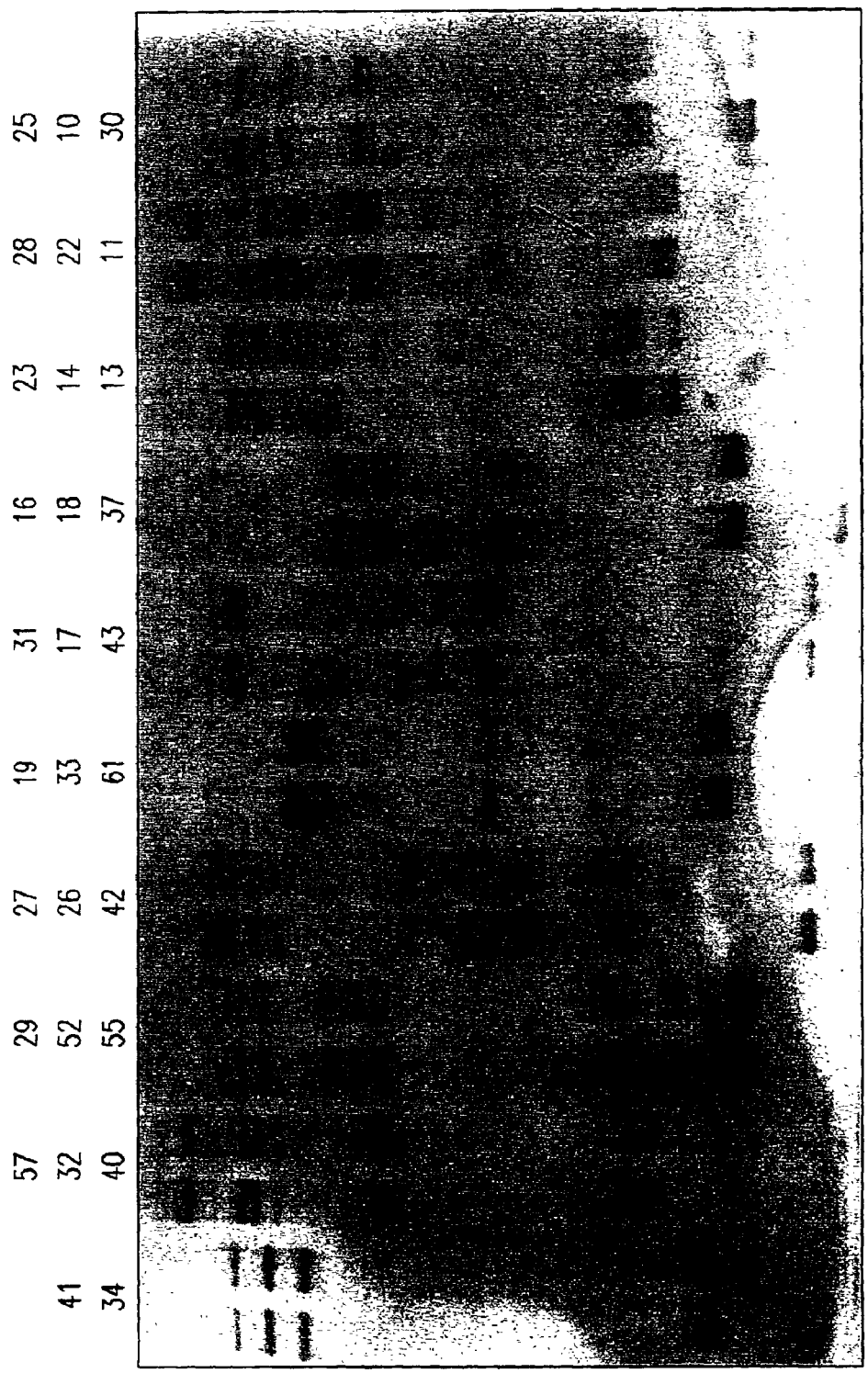
FIG. 2 is an electropherogram showing the results of mega-SSCP, one of three gels used to screen 70 PCR fragments from two patients by SSCP is shown; the arrow indicates an abnormal pattern, which is selected to be sequenced.

An assay was subsequently developed that would analyze the entire ATM gene for a small number of samples using only three SSCP gels and the primers specified in Table 1, above. Mega-SSCP also included sequential loading of sets of 2 or 3 PCR products, 29 sets of which appear in FIG. 2.

ATM Polymorphisms and Rare Variants

The screening of the ATM gene detected 34 intragenic polymorphisms or rare variants, all being new. Ten of these were common polymorphisms, with frequencies for the minor allele between 14–45% (Table 3). The experiments also detected and characterized 24 variants that were not common; the minor allele was found in less than 6% of individuals studied (Table 4). Since these tended to be found in other unrelated A-T patients, rather than in the 40 normal unrelated controls, it is problematic as to whether to refer to these as "uncommon polymorphisms" or "rare variants". There is also a strong possibility that some of these changes may have functional effects on the ATM gene or protein. Some minor alleles were observed in <1% of individuals tested, and these were considered as "rare variants". The allelic frequencies of common polymorphisms were characterized using 80 independent normal chromosomes (CEPH families) (J. Dausset et al., "Centre d'Etude du Polymorphisme Humaine (CEPH): Collaborative Genetic Mapping of the Human Genome," *Genomics* 6:575–577 (1990)). The allelic frequencies of uncommon polymorphisms and rare variants were calculated by including the 40 normal controls and 100 previously tested A-T patients (35 Turkish, 25 American, 20 Polish, 5 Costa Rican, 5 Spanish and 10 miscellaneous)—in all, 280 unrelated chromosomes. Any patients who shared a minor allele of less than 6% frequency were also haplotyped; those with shared haplotypes were considered as related with founder effect mutations and were included only once in calculating the frequency of the minor allele. Because control populations should theoretically be ethnically matched, but were not available in most cases, the allelic frequencies of the reported uncommon polymorphisms and rare variants should be considered only as estimates.

TABLE 3

Common polymorphisms in the ATM gene.

| | Allelic frequency (N = 80) |
|---|---|
| 10807A>G* | 72:28 |
| IVS3-122T>C | 55:45 |
| IVS6 + 70delT | 71:29 |
| IVS16-34C>A | 75:25 |
| IVS22-77T>C | 72:28 |
| IVS24-9delT | 86:14 |
| IVS25-13delA | 63:37 |
| 5557G>A | 75:25 |
| IVS48-69insATT | 61:39 |
| IVS62-55T>C | 69:31 |

*genomic DNA numbering (GenBank entry U82828)

TABLE 4

Uncommon polymorphisms (>1%) and rare variants (<1%) in the ATM gene.

| | Estimated allelic frequency (%) (N = 280) |
|---|---|
| 10677G>C* | 1 |
| 10742G>T* | 0.5 |
| 10819G>T* | 0.5 |
| 10948A>G* | 1 |
| IVS3-300G>A | 4 |
| IVS8-24del5 | 1 |
| IVS13-137T>C | 1 |
| IVS14-55T>G | 5 |
| 1986T>C | 0.5 |
| IVS20 + 27delT | 1 |
| IVS23-76T>C | 0 |
| IVS25-35T>A | 3 |
| IVS27-65T>C | 2 |

TABLE 4-continued

Uncommon polymorphisms (>1%) and rare variants (<1%) in the ATM gene.

| | Estimated allelic frequency (%) (N = 280) |
|---|---|
| IVS30-54T>C | 0.5 |
| 4362A>C | 0.5 |
| IVS38-8T>C | 6 |
| 5793T>C | 1 |
| IVS47-11G>T | 0.5 |
| IVS49-16T>A | 0.5 |
| IVS53 + 34insA | 1 |
| IVS60-50delTTAGTT | 0.5 |
| IVS62 + 8A>C | 2 |
| IVS62-65G>A | 0.5 |
| 9200C>G | 1.5 |

*genomic DNA numbering (GenBank entry U82828)

Discussion

Since PTT only detects mutations resulting in premature termination of the ATM protein (Telatar et al. (1996), supra) and requires RNA, a need still exists for using sequence-based methodologies, such as SSCP, in searching for ATM mutations using DNA as starting template. However, most of these technologies are very cumbersome due to the size of the ATM gene. Approaches like the mega-SSCP that are described herein provide a workable solution for the present.

As previously reported, 70% of mutations in 48 patients were detected by PTT when RNA was used as template for studying only the coding region. In the present study, RNA was not available from most patients; DNA was the only material available. In addition, this study constitutes the first screening of the ATM gene in A-T homozygotes that includes the coding region, flanking intronic areas, and promoter regions. This approach permitted the detection of missense and expression regulation mutations, which would not have been detected by PTT screening. Most strikingly, however, many more DNA changes were found in intronic sequences.

In A-T patients, mutations have been detected throughout the ATM gene, without evidence of a mutational hot spot. Furthermore, when a database generated from the work reported herein is added to all other reported mutations (Concannon and Gatti (1997), supra; http://www.vmmc.org/vmrc/atm.htm), there is no ATM exon without a mutation.

Although the SSCP conditions were carefully optimized to detect all previously known mutations in a PCR fragment, we achieved a detection efficiency of only 70% in these experiments. SSCP has been widely used to screen for mutations. Grompe (M. Grompe, "The Rapid Detection of Known Mutations in Nucleic Acids," *Nature Genet.* 5:111–117(1993)) claimed an efficiency of 100%. The data reported herein do not support this claim, at least when screening for a large variety of unknown mutations in a large gene like ATM.

Many abnormal SSCP patterns, when sequenced, were not mutations at all but corresponded to: (1) common polymorphisms (i.e., with a minor allele of >14%) that had been previously observed (unpublished), 2) uncommon polymorphisms (i.e., with a minor allele of <6%), or 3) rare variants (i.e., with a minor allele of <1%). So far, there have been only two reports about polymorphisms in the ATM gene (I. Vorechovsky et al., "ATM Mutations in Cancer Families," *Cancer Res.* 56: 4130–4133 (1996); T. Dork et al., "A Frequent Polymorphism of the Gene Mutated in Ataxia-Telangiectasia," *Mol. Cell. Probes* 11:71–73 (1997)). A total of 34 new ATM polymorphisms or rare variants were identified. Most of them (29) were found outside the coding regions, in either intronic sequences or untranslated regions (UTR). Ten of them had minor allele frequencies of >14%, and were identified as "common". The remaining 24 had minor allele frequencies of <6%. These can be grouped as either uncommon polymorphisms or rare variants; they are very uncommon in normal populations (Vorechovsky et al. (1996), supra). However, it is problematic whether some of these changes are new "polymorphisms" that have not yet had time to become fixed into the general population or, alternatively, are changes that represent functional mutations of regulatory sequences. Most were located in flanking intronic sequences, away of the exon/intron boundaries. In some cases, these changes in the ATM sequence could have phenotypic effects, as has already been suggested for the IVS40+1126A>G mutation (C. McConville et al., "Mutations Associated with Variant Phenotypes in Ataxia-Telangiectasia," *Am. J. Hum. Genet.* 59:320–330 (1996)).

In the few situations where RNA was available to test the consequences of a particular DNA change, no abnormalities were noted. However, it is still possible that these changes could have a phenotypic effect by reducing the normal level of RNA expression. That these changes have only been detected in A-T populations, and not in normal control samples, is disturbing. Such variants/polymorphisms have been previously described for other monogenic diseases; in cystic fibrosis (M. Chillon et al., "Mutations in the Cystic Fibrosis Gene in Patients with Congenital Absence of the Vas Deferens," *N. Engl. J. Med.* 332:1475–1480 (1995); X. Estivill, "Complexity in a Monogenic Disease," *Nature Genet.* 12:350 (1996)) and in adenomatous polyposis coli (S. Pedemonte et al., "Novel Germline APC Variants in Patients with Multiple Adenomas," *Genes Chromosomes Cancer* 22:257–267 (1998)) such sequence changes are associated with an altered phenotype that depends upon the ratio of expression of the normal/abnormal message. These mutations would have been initially classified as"silent DNA variants". Makridakis et al. (N. Makridakis et al., "A Prevalent Missense Substitution that Modulates Activity of Prostatic Steroid 5-Reductase," *Cancer Res.* 57:1020–1022 (1997)) have similarly observed modulated enzymatic activity with missense substitutions in the prostatic steroid 5-reductase gene. This also could be the situation for some of the rare variants that have been detected that are unique to the A-T population. Studies are underway to test this hypothesis.

Identifying new mutations is contributing valuable information for genetic counseling, prenatal testing, carrier detection, and for designing rapid assays for specific founder effect mutations. As a result of previous studies, six rapid DNA assays can now be used to detect >99% of all Costa Rican ATM mutations (Telatar et al. (1998b), supra). These mutations should also provide indirect information about functional domains of the ATM molecule, and help to clarify the role of the ATM gene in cancer predisposition. Characterization of new polymorphisms within the ATM gene should be useful as a marker system in the genetic diagnosis of A-T family members, in construction of haplotypes, and in loss of heterozygosity (LOH) studies. Knowing these mutations should also prove useful in designing chip arrays for automated mutation detection.

Advantages of the Present Invention

The present invention provides a novel method for screening large, polyexonic genes for mutations and polymorphisms, known as mega-SSCP. The mega-SSCP method provides a method for screening genes for multiple polymorphisms and mutations at once by using a small number of electrophoreses. This method is of particular use for detection of mutations and polymorphisms in the ATM gene, but can be used for many other genes as well. The method is particularly useful for large, polyexonic, eukaryotic genes, particularly those where mutations or polymorphisms can occur at many points within the gene and not merely at one or a few hot spots.

The present invention also provides novel mutations and polymorphisms in the ATM gene that are useful in screening DNA. In particular, the novel polymorphisms are important because it is necessary to screen out such polymorphisms in screening for mutations that cause a loss of function of the ATM gene and thus increase the signal-to-noise ratio for screening of DNA for such mutations.

Although the present invention has been described in considerable detail, with reference to certain preferred versions thereof, other versions and embodiments are possible. Therefore, the scope of the invention is determined by the following claims.

I claim:

1. An isolated and purified nucleic acid fragment comprising nucleic acid having complementarity or identity to a mutation in the ataxia-telangiectasia mutated (ATM) gene, the mutation being selected from the group consisting of:
   (a) 10744A>G;
   (b) 11482G>A;
   (c) IVS3-558A>T;
   (d) 381delA;
   (e) IVS8-3delGT;
   (f) 1028delAAAA;
   (g) 1120C>T;
   (h) 1930ins16;
   (i) IVS16+2T>C;
   (j) IVS21+1G>A;
   (k) 3085delA;
   (l) 3381delTGAC;
   (m) 3602delTT;
   (n) 4052delT;
   (o) 4396C>T;
   (p) 5188C>T;
   (q) 5546delT;
   (r) 5791G>CCT;
   (s) 6047A>G;
   (t) IVS44-1G>T;
   (u) 6672delGC/6677delTACG;
   (v) 6736del11/6749del7;
   (w) 7159insAGCC;
   (x) 7671delGTTT;
   (y) 7705del14;
   (z) 7979delTGT;
   (aa) 8177C>T;
   (ab) 8545C>T;
   (ac) 8565T>A;
   (ad) IVS64+1G>T; and
   (ae) 9010del28.

2. The fragment of claim 1 wherein the fragment has complementarity to the mutation in the ATM gene, is hairpin shaped, is covalently linked to a fluorophore and to a quencher, and has a structure such that the fluorophore is internally quenched by the quencher when the fragment is not base-paired and such that the internal quenching is relieved when the fragment is base-paired, thereby restoring fluorescence of the fluorophore.

3. The fragment of claim 1 wherein the fragment is DNA, has complementarity to the mutation in the ATM gene, and wherein the fragment further includes, covalently linked to either its 5'-end or to its 3'-end, a segment of about 40 bases, the segment of about 40 bases comprising a repeating unit of dCdG or dGdC.

4. A method for testing a DNA sample of a human for the presence or absence of a mutation in the ATM gene comprising the steps of:
 (a) providing a sample of DNA from a human; and
 (b) testing the sample for the presence of a mutation in the ATM gene, the mutation being selected from the group consisting of:
  (i) 10744A>G;
  (ii) 11482G>A;
  (iii) IVS3-558A>T;
  (iv) 381delA;
  (v) IVS8-3delGT;
  (vi) 1028delAAAA;
  (vii) 1120C>T;
  (viii) 1930ins16;
  (ix) IVS16+2T>C;
  (x) IVS21+1G>A;
  (xi) 3085delA;
  (xii) 3381delTGAC;
  (xiii) 3602delTT;
  (xiv) 4052delT;
  (xv) 4396C>T;
  (xvi) 5188C>T;
  (xvii) 5546delT;
  (xviii) 5791G>CCT;
  (xix) 6047A>G;
  (xx) IVS44-1G>T;
  (xxi) 6672delGC/6677delTACG;
  (xxii) 6736del11/6749del7;
  (xxiii) 7159insAGCC;
  (xxiv) 7671delGTTT;
  (xxv) 7705del14;
  (xxvi) 7979 delTGT;
  (xxvii) 8177C>T;
  (xxviii) 8545C>T;
  (xxix) 8565T>A;
  (xxx) IVS64+1G>T; and
  (xxxi) 9010del28.

5. An isolated and purified nucleic acid fragment comprising nucleic acid having complementarity or identity to a polymorphism in the ataxia-telangiectasia mutated (ATM) gene, the polymorphism being selected from the group consisting of:
 (a) 10807A>G;
 (b) IVS3-122T>C;
 (c) IVS6+70delT;
 (d) IVS16-34C>A;
 (e) IVS22-77T>C;
 (f) IVS24-9delT;
 (g) IVS25-13delA;
 (h) IVS48-69insATT; and
 (i) IVS62-55T>C.

6. The fragment of claim 5 wherein the fragment has complementarity to the polymorphism in the ATM gene, is hairpin shaped, is covalently linked to a fluorophore and to a quencher, and has a structure such that the fluorophore is internally quenched by the quencher when the fragment is not base-paired and such that the internal quenching is relieved when the fragment is base-paired, thereby restoring fluorescence of the fluorophore.

7. The fragment of claim 5 wherein the fragment is DNA, has complementarity to the polymorphism in the ATM gene, and wherein the fragment further includes, covalently linked to either its 5'-end or to its 3'-end, a segment of about 40 bases, the segment of about 40 bases comprising a repeating unit of dCdG or dGdC.

8. A method for testing a DNA sample of a human for the presence or absence of a polymorphism in the ATM gene comprising the steps of:
 (a) providing a sample of DNA from a human; and
 (b) testing the sample for the presence of a polymorphism in the ATM gene, the polymorphism being selected from the group consisting of:
  (i) 10807A>G;
  (ii) IVS3-122T>C;
  (iii) IVS6+70delT;
  (iv) IVS16-34C>A;
  (v) IVS22-77T>C;
  (vi) IVS24-9delT;
  (vii) IVS25-13delA;
  (viii) IVS48-69insATT; and
  (xix) IVS62-55T>C.

9. An isolated and purified nucleic acid fragment comprising nucleic acid having complementarity or identity to a polymorphism in the ataxia-telangiectasia mutated (ATM) gene, the polymorphism being selected from the group consisting of:
 (a) 10677G>C;
 (b) 10742G>T;
 (c) 10819G>T;
 (d) 10948A>G;
 (e) IVS3-300G>A;
 (f) IVS8>24del5;
 (g) IVS13-137T>C;
 (h) IVS14-55T>G;
 (i) IVS20+27delT;
 (j) IVS23-76T>C;
 (k) IVS25-35T>A;
 (l) IVS27-65T>C;
 (m) IVS30-54T>C;
 (n) 4362A>C;
 (o) IVS38-8T>C;
 (p) 5793T>C;
 (q) IVS47-11G>T;
 (r) IVS49-16T>A;
 (s) IVS53+34insA;
 (t) IVS60-50delTTAGTT;
 (u) IVS62+8A>C;
 (v) IVS62-65G>A; and
 (w) 9200C>G.

10. The fragment of claim 9 wherein the fragment has complementarity to the polymorphism in the ATM gene, is hairpin shaped, is covalently linked to a fluorophore and to a quencher, and has a structure such that the fluorophore is internally quenched by the quencher when the fragment is not base-paired and such that the internal quenching is relieved when the fragment is base-paired, thereby restoring fluorescence of the fluorophore.

11. The fragment of claim 9 wherein the fragment is DNA, has complementarity to the polymorphism in the ATM gene, and wherein the fragment further includes, covalently linked to either its 5'-end or to its 3'-end, a segment of about 40 bases, the segment of about 40 bases comprising a repeating unit of dCdG or dGdC.

12. A method for testing a DNA sample of a human for the presence or absence of a polymorphism in the ATM gene comprising the steps of:
(a) providing a sample of DNA from a human; and
(b) testing the sample for the presence of a polymorphism in the ATM gene, the polymorphism being selected from the group consisting of:
(i) 1067G>C;
(ii) 10742G>T;
(iii) 10819G>T;
(iv) 10948A>G;
(v) IVS3-300G>A;
(vi) IVS8>24del5;
(vii) IVS13-137T>C;
(viii) IVS14-55T>G;
(ix) IVS20+27delT;
(x) IVS23-76T>C;
(xi) IVS25-35T>A;
(xii) IVS27-65T>C;
(xiii) IVS30-54T>C;
(xiv) 4362A>C;
(xv) IVS38-8T>C;
(xvi) 5793T>C;
(xvii) IVS47-11G>T;
(xviii) IVS49-16T>A;
(xix) IVS53+34insA;
(xx) IVS60-50delTTAGTT;
(xxi) IVS62+8A>C;
(xxii) IVS62-65G>A; and
(xxiii) 9200C>G.

13. The isolated and purified nucleic acid fragment of claim 1, wherein the mutation is selected from the group consisting of 10744A>G, 11482G>A, and IVS3-558A>T.

14. The isolated and purified nucleic acid fragment of claim 1, wherein the mutation is selected from the group consisting of 381delA, IVS8-3delGT, and 1028delAAAA.

15. The isolated and purified nucleic acid fragment of claim 1, wherein the mutation is selected from the group consisting of 1120C>T, 1930ins16, and IVS16+2T>C.

16. The isolated and purified nucleic acid fragment of claim 1, wherein, the mutation is selected from the group consisting of IVS21+1G>A, 3085delA, and 3381delTGAC.

17. The isolated and purified nucleic acid fragment of claim 1, wherein the mutation is selected from the group consisting of 3602delTT, 4052delT, and 4396C>T.

18. The isolated and purified nucleic acid fragment of claim 1, wherein the mutation is selected from the group consisting of 5188C>T, 5546delT, and 5791G>CCT.

19. The isolated and purified nucleic acid fragment of claim 1, wherein the mutation is selected from the group consisting of 6047A>G, IVS44-1G>T, and 6672delGC/6677delTACG.

20. The isolated and purified nucleic acid fragment of claim 1, wherein the mutation is selected from the group consisting of 6736del11/6749del7, 7159insAGCC, and 7671delGTTT.

21. The isolated and purified nucleic acid fragment of claim 1, wherein the mutation is selected from the group consisting of 7705del14, 7979delTGT, and 8177C>T.

22. The isolated and purified nucleic acid fragment of claim 1, wherein the mutation is selected from the group consisting of 8545C>T, 8565T>A, IVS64+1G>T, and 9010del28.

23. The isolated and purified nucleic acid fragment of claim 5, wherein the polymorphism is selected from the group consisting of 10807A>G, IVS3-122T>C, and IVS6+70delT.

24. The isolated and purified nucleic acid fragment of claim 5, wherein the polymorphism is selected from the group consisting of IVS16-34C>A, IVS22-77T>C, and IVS24-9delT.

25. The isolated and purified nucleic acid fragment of claim 5, wherein the polymorphism is selected from the group consisting of IVS25-13delA, IVS48-69insATT, and IVS62-55T>C.

26. The isolated and purified nucleic acid fragment of claim 9, wherein the polymorphism is selected from the group consisting of 10677G>C, 10742G>T, and 10819G>T.

27. The isolated and purified nucleic acid fragment of claim 9, wherein the polymorphism is selected from the group consisting of 10948A>G, IVS3-300G>A, and IVS8>24del5.

28. The isolated and purified nucleic acid fragment of claim 9, wherein the polymorphism is selected from the group consisting of IVS13-137T>C, IVS14-55T>G, and IVS20+27delT.

29. The isolated and purified nucleic acid fragment of claim 9, wherein the polymorphism is selected from the group consisting of IVS23-76T>C, IVS25-35T>A, and IVS27-65T>C.

30. The isolated and purified nucleic acid fragment of claim 9, wherein the polymorphism is selected from the group consisting of IVS30-54T>C, 4362A>C, and IVS38-8T>C.

31. The isolated and purified nucleic acid fragment of claim 9, wherein the polymorphism is selected from the group consisting of 5793T>C, IVS47-11G>T, and IVS49-16T>A.

32. The isolated and purified nucleic acid fragment of claim 9, wherein the polymorphism is selected from the group consisting of IVS53+34insA, IVS60-50delTTAGTT, and IVS62+8A>C.

33. The isolated and purified nucleic acid fragment of claim 9, wherein the polymorphism is selected from the group consisting of IVS62-65G>A, and 9200C>G.

* * * * *

SEQUENCE LISTING

<160> NUMBER OF SEQ ID NOS: 143

<210> SEQ ID NO 1
<211> LENGTH: 9385
<212> TYPE: DNA
<213> ORGANISM: Human
<220> FEATURE:
<221> NAME/KEY: CDS
<222> LOCATION: (190)...(9357)

<400> SEQUENCE: 1

```
gcgagaggag tcgggatctg cgctgcagcc accgccgcgg ttgatactac tttgaccttc      60
cgagtgcagt gaggcataca tcacaatttg gaattatgca ttggtttatc aatttacttg     120
tttattgtca ccctgctgcc cagatatgac ttcatgagga cagtgatgtg tgttctgaaa     180 ttgtgaacc atg agt cta gta ctt aat gat ctg ctt atc tgc tgc cgt caa     231
         Met Ser Leu Val Leu Asn Asp Leu Leu Ile Cys Cys Arg Gln
             1               5                  10 cta gaa cat gat aga gct aca gaa cga aag aaa gaa gtt gag aaa ttt      279
Leu Glu His Asp Arg Ala Thr Glu Arg Lys Lys Glu Val Glu Lys Phe
15                  20                  25                  30 aag cgc ctg att cga gat cct gaa aca att aaa cat cta gat cgg cat      327
Lys Arg Leu Ile Arg Asp Pro Glu Thr Ile Lys His Leu Asp Arg His
                35                  40                  45 tca gat tcc aaa caa gga aaa tat ttg aat tgg gat gct gtt ttt aga      375
Ser Asp Ser Lys Gln Gly Lys Tyr Leu Asn Trp Asp Ala Val Phe Arg
            50                  55                  60 ttt tta cag aaa tat att cag aaa gaa aca gaa tgt ctg aga ata gca      423
Phe Leu Gln Lys Tyr Ile Gln Lys Glu Thr Glu Cys Leu Arg Ile Ala
        65                  70                  75 aaa cca aat gta tca gcc tca aca caa gcc tcc agg cag aaa aag atg      471
Lys Pro Asn Val Ser Ala Ser Thr Gln Ala Ser Arg Gln Lys Lys Met
    80                  85                  90 cag gaa atc agt agt ttg gtc aaa tac ttc atc aaa tgt gca aac aga      519
Gln Glu Ile Ser Ser Leu Val Lys Tyr Phe Ile Lys Cys Ala Asn Arg
9 5                 100                 105                 110 aga gca cct agg cta aaa tgt caa gaa ctc tta aat tat atc atg gat      567
Arg Ala Pro Arg Leu Lys Cys Gln Glu Leu Leu Asn Tyr Ile Met Asp
                115                 120                 125 aca gtg aaa gat tca tct aat ggt gct att tac gga gct gat tgt agc      615
Thr Val Lys Asp Ser Ser Asn Gly Ala Ile Tyr Gly Ala Asp Cys Ser
            130                 135                 140 aac ata cta ctc aaa gac att ctt tct gtg aga aaa tac tgg tgt gaa      663
Asn Ile Leu Leu Lys Asp Ile Leu Ser Val Arg Lys Tyr Trp Cys Glu
        145                 150                 155 ata tct cag caa cag tgg tta gaa ttg ttc tct gtg tac ttc agg ctc      711
Ile Ser Gln Gln Gln Trp Leu Glu Leu Phe Ser Val Tyr Phe Arg Leu
    160                 165                 170
```

-continued

| | | |
|---|---|---|
| tat ctg aaa cct tca caa gat gtt cat aga gtt tta gtg gct aga ata<br>Tyr Leu Lys Pro Ser Gln Asp Val His Arg Val Leu Val Ala Arg Ile<br>175                     180                   185                 190 | 759 |
| att cat gct gtt acc aaa gga tgc tgt tct cag act gac gga tta aat<br>Ile His Ala Val Thr Lys Gly Cys Cys Ser Gln Thr Asp Gly Leu Asn<br>                             195                   200                   205 | 807 |
| tcc aaa ttt ttg gac ttt ttt tcc aag gct att cag tgt gcg aga caa<br>Ser Lys Phe Leu Asp Phe Phe Ser Lys Ala Ile Gln Cys Ala Arg Gln<br>          210                   215                   220 | 855 |
| gaa aag agc tct tca ggt cta aat cat atc tta gca gct ctt act atc<br>Glu Lys Ser Ser Ser Gly Leu Asn His Ile Leu Ala Ala Leu Thr Ile<br>                225                   230                   235 | 903 |
| ttc ctc aag act ttg gct gtc aac ttt cga att cga gtg tgt gaa tta<br>Phe Leu Lys Thr Leu Ala Val Asn Phe Arg Ile Arg Val Cys Glu Leu<br>240                     245                   250 | 951 |
| gga gat gaa att ctt ccc act ttg ctt tat att tgg act caa cat agg<br>Gly Asp Glu Ile Leu Pro Thr Leu Leu Tyr Ile Trp Thr Gln His Arg<br>255                     260                   265                 270 | 999 |
| ctt aat gat tct tta aaa gaa gtc att att gaa tta ttt caa ctg caa<br>Leu Asn Asp Ser Leu Lys Glu Val Ile Ile Glu Leu Phe Gln Leu Gln<br>                         275                   280                   285 | 1047 |
| att tat atc cat cat ccc aaa gga gcc aaa acc caa gaa aaa ggt gct<br>Ile Tyr Ile His His Pro Lys Gly Ala Lys Thr Gln Glu Lys Gly Ala<br>                    290                   295                   300 | 1095 |
| tat gaa tca aca aaa tgg aga agt att tta tac aac tta tat gat ctg<br>Tyr Glu Ser Thr Lys Trp Arg Ser Ile Leu Tyr Asn Leu Tyr Asp Leu<br>               305                   310                   315 | 1143 |
| cta gtg aat gag ata agt cat ata gga agt aga gga aag tat tct tca<br>Leu Val Asn Glu Ile Ser His Ile Gly Ser Arg Gly Lys Tyr Ser Ser<br>320                     325                   330 | 1191 |
| gga ttt cgt aat att gcc gtc aaa gaa aat ttg att gaa ttg atg gca<br>Gly Phe Arg Asn Ile Ala Val Lys Glu Asn Leu Ile Glu Leu Met Ala<br>335                     340                   345                 350 | 1239 |
| gat atc tgt cac cag gtt ttt aat gaa gat acc aga tcc ttg gag att<br>Asp Ile Cys His Gln Val Phe Asn Glu Asp Thr Arg Ser Leu Glu Ile<br>                         355                   360                   365 | 1287 |
| tct caa tct tac act act aca caa aga gaa tct agt gat tac agt gtc<br>Ser Gln Ser Tyr Thr Thr Thr Gln Arg Glu Ser Ser Asp Tyr Ser Val<br>                    370                   375                   380 | 1335 |
| cct tgc aaa agg aag aaa ata gaa cta ggc tgg gaa gta ata aaa gat<br>Pro Cys Lys Arg Lys Lys Ile Glu Leu Gly Trp Glu Val Ile Lys Asp<br>               385                   390                   395 | 1383 |
| cac ctt cag aag tca cag aat gat ttt gat ctt gtg cct tgg cta cag<br>His Leu Gln Lys Ser Gln Asn Asp Phe Asp Leu Val Pro Trp Leu Gln<br>400                     405                   410 | 1431 |
| att gca acc caa tta ata tca aag tat cct gca agt tta cct aac tgt<br>Ile Ala Thr Gln Leu Ile Ser Lys Tyr Pro Ala Ser Leu Pro Asn Cys<br>415                     420                   425                 430 | 1479 |
| gag ctg tct cca tta ctg atg ata cta tct cag ctt cta ccc caa cag<br>Glu Leu Ser Pro Leu Leu Met Ile Leu Ser Gln Leu Leu Pro Gln Gln<br>                         435                   440                   445 | 1527 |
| cga cat ggg gaa cgt aca cca tat gtg tta cga tgc ctt acg gaa gtt<br>Arg His Gly Glu Arg Thr Pro Tyr Val Leu Arg Cys Leu Thr Glu Val<br>                  450                   455                   460 | 1575 |
| gca ttg tgt caa gac aag agg tca aac cta gaa agc tca caa aag tca<br>Ala Leu Cys Gln Asp Lys Arg Ser Asn Leu Glu Ser Ser Gln Lys Ser<br>               465                   470                   475 | 1623 |
| gat tta tta aaa ctc tgg aat aaa att tgg tgt att acc ttt cgt ggt<br>Asp Leu Leu Lys Leu Trp Asn Lys Ile Trp Cys Ile Thr Phe Arg Gly<br>480                     485                   490 | 1671 |

-continued

| | | |
|---|---|---|
| ata agt tct gag caa ata caa gct gaa aac ttt ggc tta ctt gga gcc<br>Ile Ser Ser Glu Gln Ile Gln Ala Glu Asn Phe Gly Leu Leu Gly Ala<br>495                 500                     505                 510 | | 1719 |
| ata att cag ggt agt tta gtt gag gtt gac aga gaa ttc tgg aag tta<br>Ile Ile Gln Gly Ser Leu Val Glu Val Asp Arg Glu Phe Trp Lys Leu<br>              515                    520                   525 | | 1767 |
| ttt act ggg tca gcc tgc aga cct tca tgt cct gca gta tgc tgt ttg<br>Phe Thr Gly Ser Ala Cys Arg Pro Ser Cys Pro Ala Val Cys Cys Leu<br>              530                    535                 540 | | 1815 |
| act ttg gca ctg acc acc agt ata gtt cca gga gcg gta aaa atg gga<br>Thr Leu Ala Leu Thr Thr Ser Ile Val Pro Gly Ala Val Lys Met Gly<br>            545                    550                 555 | | 1863 |
| ata gag caa aat atg tgt gaa gta aat aga agc ttt tct tta aag gaa<br>Ile Glu Gln Asn Met Cys Glu Val Asn Arg Ser Phe Ser Leu Lys Glu<br>560                 565                    570 | | 1911 |
| tca ata atg aaa tgg ctc tta ttc tat cag tta gag ggt gac tta gaa<br>Ser Ile Met Lys Trp Leu Leu Phe Tyr Gln Leu Glu Gly Asp Leu Glu<br>575                 580                    585                 590 | | 1959 |
| aat agc aca gaa gtg cct cca att ctt cac agt aat ttt cct cat ctt<br>Asn Ser Thr Glu Val Pro Pro Ile Leu His Ser Asn Phe Pro His Leu<br>              595                    600                 605 | | 2007 |
| gta ctg gag aaa att ctt gtg agt ctc act atg aaa aac tgt aaa gct<br>Val Leu Glu Lys Ile Leu Val Ser Leu Thr Met Lys Asn Cys Lys Ala<br>            610                    615                   620 | | 2055 |
| gca atg aat ttt ttc caa agc gtg cca gaa tgt gaa cac cac caa aaa<br>Ala Met Asn Phe Phe Gln Ser Val Pro Glu Cys Glu His His Gln Lys<br>              625                    630                 635 | | 2103 |
| gat aaa gaa gaa ctt tca ttc tca gaa gta gaa gaa cta ttt ctt cag<br>Asp Lys Glu Glu Leu Ser Phe Ser Glu Val Glu Glu Leu Phe Leu Gln<br>640                 645                    650 | | 2151 |
| aca act ttt gac aag atg gac ttt tta acc att gtg aga gaa tgt ggt<br>Thr Thr Phe Asp Lys Met Asp Phe Leu Thr Ile Val Arg Glu Cys Gly<br>655                 660                    665                 670 | | 2199 |
| ata gaa aag cac cag tcc agt att ggc ttc tct gtc cac cag aat ctc<br>Ile Glu Lys His Gln Ser Ser Ile Gly Phe Ser Val His Gln Asn Leu<br>              675                    680                 685 | | 2247 |
| aag gaa tca ctg gat cgc tgt ctt ctg gga tta tca gaa cag ctt ctg<br>Lys Glu Ser Leu Asp Arg Cys Leu Leu Gly Leu Ser Glu Gln Leu Leu<br>            690                    695                 700 | | 2295 |
| aat aat tac tca tct gag att aca aat tca gaa act ctt gtc cgg tgt<br>Asn Asn Tyr Ser Ser Glu Ile Thr Asn Ser Glu Thr Leu Val Arg Cys<br>705                 710                    715 | | 2343 |
| tca cgt ctt ttg gtg ggt gtc ctt ggc tgc tac tgt tac atg ggt gta<br>Ser Arg Leu Leu Val Gly Val Leu Gly Cys Tyr Cys Tyr Met Gly Val<br>720                 725                    730 | | 2391 |
| ata gct gaa gag gaa gca tat aag tca gaa tta ttc cag aaa gcc aac<br>Ile Ala Glu Glu Glu Ala Tyr Lys Ser Glu Leu Phe Gln Lys Ala Asn<br>735                 740                    745                 750 | | 2439 |
| tct cta atg caa tgt gca gga gaa agt atc act ctg ttt aaa aat aag<br>Ser Leu Met Gln Cys Ala Gly Glu Ser Ile Thr Leu Phe Lys Asn Lys<br>              755                    760                 765 | | 2487 |
| aca aat gag gaa ttc aga att ggt tcc ttg aga aat atg atg cag cta<br>Thr Asn Glu Glu Phe Arg Ile Gly Ser Leu Arg Asn Met Met Gln Leu<br>            770                    775                 780 | | 2535 |
| tgt aca cgt tgc ttg agc aac tgt acc aag aag agt cca aat aag att<br>Cys Thr Arg Cys Leu Ser Asn Cys Thr Lys Lys Ser Pro Asn Lys Ile<br>785                 790                    795 | | 2583 |
| gca tct ggc ttt ttc ctg cga ttg tta aca tca aag cta atg aat gac<br>Ala Ser Gly Phe Phe Leu Arg Leu Leu Thr Ser Lys Leu Met Asn Asp | | 2631 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 800 |     |     |     |     | 805 |     |     |     |     |     | 810 |     |     |      |
| att | gca | gat | att | tgt | aaa | agt | tta | gca | tcc | ttc | atc | aaa | aag | cca | ttt | 2679 |
| Ile | Ala | Asp | Ile | Cys | Lys | Ser | Leu | Ala | Ser | Phe | Ile | Lys | Lys | Pro | Phe |      |
| 815 |     |     |     | 820 |     |     |     |     | 825 |     |     |     |     | 830 |     |      |
| gac | cgt | gga | gaa | gta | gaa | tca | atg | gaa | gat | gat | act | aat | gga | aat | cta | 2727 |
| Asp | Arg | Gly | Glu | Val | Glu | Ser | Met | Glu | Asp | Asp | Thr | Asn | Gly | Asn | Leu |      |
|     |     |     |     | 835 |     |     |     |     | 840 |     |     |     |     | 845 |     |      |
| atg | gag | gtg | gag | gat | cag | tca | tcc | atg | aat | cta | ttt | aac | gat | tac | cct | 2775 |
| Met | Glu | Val | Glu | Asp | Gln | Ser | Ser | Met | Asn | Leu | Phe | Asn | Asp | Tyr | Pro |      |
|     |     |     | 850 |     |     |     |     | 855 |     |     |     |     | 860 |     |     |      |
| gat | agt | agt | gtt | agt | gat | gca | aac | gaa | cct | gga | gag | agc | caa | agt | acc | 2823 |
| Asp | Ser | Ser | Val | Ser | Asp | Ala | Asn | Glu | Pro | Gly | Glu | Ser | Gln | Ser | Thr |      |
|     |     | 865 |     |     |     |     | 870 |     |     |     |     | 875 |     |     |     |      |
| ata | ggt | gcc | att | aat | cct | tta | gct | gaa | gaa | tat | ctg | tca | aag | caa | gat | 2871 |
| Ile | Gly | Ala | Ile | Asn | Pro | Leu | Ala | Glu | Glu | Tyr | Leu | Ser | Lys | Gln | Asp |      |
|     | 880 |     |     |     |     | 885 |     |     |     |     | 890 |     |     |     |     |      |
| cta | ctt | ttc | tta | gac | atg | ctc | aag | ttc | ttg | tgt | ttg | tgt | gta | act | act | 2919 |
| Leu | Leu | Phe | Leu | Asp | Met | Leu | Lys | Phe | Leu | Cys | Leu | Cys | Val | Thr | Thr |      |
| 895 |     |     |     |     | 900 |     |     |     |     | 905 |     |     |     |     | 910 |      |
| gct | cag | acc | aat | act | gtg | tcc | ttt | agg | gca | gct | gat | att | cgg | agg | aaa | 2967 |
| Ala | Gln | Thr | Asn | Thr | Val | Ser | Phe | Arg | Ala | Ala | Asp | Ile | Arg | Arg | Lys |      |
|     |     |     |     | 915 |     |     |     |     | 920 |     |     |     |     | 925 |     |      |
| ttg | tta | atg | tta | att | gat | tct | agc | acg | cta | gaa | cct | acc | aaa | tcc | ctc | 3015 |
| Leu | Leu | Met | Leu | Ile | Asp | Ser | Ser | Thr | Leu | Glu | Pro | Thr | Lys | Ser | Leu |      |
|     |     |     | 930 |     |     |     |     | 935 |     |     |     |     | 940 |     |     |      |
| cac | ctg | cat | atg | tat | cta | atg | ctt | tta | aag | gag | ctt | cct | gga | gaa | gag | 3063 |
| His | Leu | His | Met | Tyr | Leu | Met | Leu | Leu | Lys | Glu | Leu | Pro | Gly | Glu | Glu |      |
|     |     | 945 |     |     |     |     | 950 |     |     |     |     | 955 |     |     |     |      |
| tac | ccc | ttg | cca | atg | gaa | gat | gtt | ctt | gaa | ctt | ctg | aaa | cca | cta | tcc | 3111 |
| Tyr | Pro | Leu | Pro | Met | Glu | Asp | Val | Leu | Glu | Leu | Leu | Lys | Pro | Leu | Ser |      |
|     | 960 |     |     |     |     | 965 |     |     |     |     | 970 |     |     |     |     |      |
| aat | gtg | tgt | tct | ttg | tat | cgt | cgt | gac | caa | gat | gtt | tgt | aaa | act | att | 3159 |
| Asn | Val | Cys | Ser | Leu | Tyr | Arg | Arg | Asp | Gln | Asp | Val | Cys | Lys | Thr | Ile |      |
| 975 |     |     |     |     | 980 |     |     |     |     | 985 |     |     |     |     | 990 |      |
| tta | aac | cat | gtc | ctt | cat | gta | gtg | aaa | aac | cta | ggt | caa | agc | aat | atg | 3207 |
| Leu | Asn | His | Val | Leu | His | Val | Val | Lys | Asn | Leu | Gly | Gln | Ser | Asn | Met |      |
|     |     |     |     | 995 |     |     |     |     | 1000|     |     |     |     | 1005|     |      |
| gac | tct | gag | aac | aca | agg | gat | gct | caa | gga | cag | ttt | ctt | aca | gta | att | 3255 |
| Asp | Ser | Glu | Asn | Thr | Arg | Asp | Ala | Gln | Gly | Gln | Phe | Leu | Thr | Val | Ile |      |
|     |     |     | 1010|     |     |     |     | 1015|     |     |     |     | 1020|     |     |      |
| gga | gca | ttt | tgg | cat | cta | aca | aag | gag | agg | aaa | tat | ata | ttc | tct | gta | 3303 |
| Gly | Ala | Phe | Trp | His | Leu | Thr | Lys | Glu | Arg | Lys | Tyr | Ile | Phe | Ser | Val |      |
|     |     |     | 1025|     |     |     |     | 1030|     |     |     |     | 1035|     |     |      |
| aga | atg | gcc | cta | gta | aat | tgc | ctt | aaa | act | ttg | ctt | gag | gct | gat | cct | 3351 |
| Arg | Met | Ala | Leu | Val | Asn | Cys | Leu | Lys | Thr | Leu | Leu | Glu | Ala | Asp | Pro |      |
|     | 1040|     |     |     |     | 1045|     |     |     |     | 1050|     |     |     |     |      |
| tat | tca | aaa | tgg | gcc | att | ctt | aat | gta | atg | gga | aaa | gac | ttt | cct | gta | 3399 |
| Tyr | Ser | Lys | Trp | Ala | Ile | Leu | Asn | Val | Met | Gly | Lys | Asp | Phe | Pro | Val |      |
| 1055|     |     |     | 1060|     |     |     |     | 1065|     |     |     |     | 1070|     |      |
| aat | gaa | gta | ttt | aca | caa | ttt | ctt | gct | gac | aat | cat | cac | caa | gtt | cgc | 3447 |
| Asn | Glu | Val | Phe | Thr | Gln | Phe | Leu | Ala | Asp | Asn | His | His | Gln | Val | Arg |      |
|     |     |     | 1075|     |     |     |     | 1080|     |     |     |     | 1085|     |     |      |
| atg | ttg | gct | gca | gag | tca | atc | aat | aga | ttg | ttc | cag | gac | acg | aag | gga | 3495 |
| Met | Leu | Ala | Ala | Glu | Ser | Ile | Asn | Arg | Leu | Phe | Gln | Asp | Thr | Lys | Gly |      |
|     |     |     | 1090|     |     |     |     | 1095|     |     |     |     | 1100|     |     |      |
| gat | tct | tcc | agg | tta | ctg | aaa | gca | ctt | cct | ttg | aag | ctt | cag | caa | aca | 3543 |
| Asp | Ser | Ser | Arg | Leu | Leu | Lys | Ala | Leu | Pro | Leu | Lys | Leu | Gln | Gln | Thr |      |
|     |     |     | 1105|     |     |     |     | 1110|     |     |     |     | 1115|     |     |      |
| gct | ttt | gaa | aat | gca | tac | ttg | aaa | gct | cag | gaa | gga | atg | aga | gaa | atg | 3591 |

```
                Ala Phe Glu Asn Ala Tyr Leu Lys Ala Gln Glu Gly Met Arg Glu Met
                    1120                1125                1130 tcc cat agt gct gag aac cct gaa act ttg gat gaa att tat aat aga       3639
Ser His Ser Ala Glu Asn Pro Glu Thr Leu Asp Glu Ile Tyr Asn Arg
1135            1140                1145                1150 aaa tct gtt tta ctg acg ttg ata gct gtg gtt tta tcc tgt agc cct       3687
Lys Ser Val Leu Leu Thr Leu Ile Ala Val Val Leu Ser Cys Ser Pro
                1155                1160                1165 atc tgc gaa aaa cag gct ttg ttt gcc ctg tgt aaa tct gtg aaa gag       3735
Ile Cys Glu Lys Gln Ala Leu Phe Ala Leu Cys Lys Ser Val Lys Glu
            1170                1175                1180 aat gga tta gaa cct cac ctt gtg aaa aag gtt tta gag aaa gtt tct       3783
Asn Gly Leu Glu Pro His Leu Val Lys Lys Val Leu Glu Lys Val Ser
        1185                1190                1195 gaa act ttt gga tat aga cgt tta gaa gac ttt atg gca tct cat tta       3831
Glu Thr Phe Gly Tyr Arg Arg Leu Glu Asp Phe Met Ala Ser His Leu
    1200                1205                1210 gat tat ctg gtt ttg gaa tgg cta aat ctt caa gat act gaa tac aac       3879
Asp Tyr Leu Val Leu Glu Trp Leu Asn Leu Gln Asp Thr Glu Tyr Asn
1215            1220                1225                1230 tta tct tct ttt cct ttt att tta tta aac tac aca aat att gag gat       3927
Leu Ser Ser Phe Pro Phe Ile Leu Leu Asn Tyr Thr Asn Ile Glu Asp
                1235                1240                1245 ttc tat aga tct tgt tat aag gtt ttg att cca cat ctg gtg att aga       3975
Phe Tyr Arg Ser Cys Tyr Lys Val Leu Ile Pro His Leu Val Ile Arg
            1250                1255                1260 agt cat ttt gat gag gtg aag tcc att gct aat cag att caa gag gac       4023
Ser His Phe Asp Glu Val Lys Ser Ile Ala Asn Gln Ile Gln Glu Asp
        1265                1270                1275 tgg aaa agt ctt cta aca gac tgc ttt cca aag att ctt gta aat att       4071
Trp Lys Ser Leu Leu Thr Asp Cys Phe Pro Lys Ile Leu Val Asn Ile
    1280                1285                1290 ctt cct tat ttt gcc tat gag ggt acc aga gac agt ggg atg gca cag       4119
Leu Pro Tyr Phe Ala Tyr Glu Gly Thr Arg Asp Ser Gly Met Ala Gln
1295            1300                1305                1310 caa aga gag act gct acc aag gtc tat gat atg ctt aaa agt gaa aac       4167
Gln Arg Glu Thr Ala Thr Lys Val Tyr Asp Met Leu Lys Ser Glu Asn
                1315                1320                1325 tta ttg gga aaa cag att gat cac tta ttc att agt aat tta cca gag       4215
Leu Leu Gly Lys Gln Ile Asp His Leu Phe Ile Ser Asn Leu Pro Glu
            1330                1335                1340 att gtg gtg gag tta ttg atg acg tta cat gag cca gca aat tct agt       4263
Ile Val Val Glu Leu Leu Met Thr Leu His Glu Pro Ala Asn Ser Ser
        1345                1350                1355 gcc agt cag agc act gac ctc tgt gac ttt tca ggg gat ttg gat cct       4311
Ala Ser Gln Ser Thr Asp Leu Cys Asp Phe Ser Gly Asp Leu Asp Pro
    1360                1365                1370 gct cct aat cca cct cat ttt cca tcg cat gtg att aaa gca aca ttt       4359
Ala Pro Asn Pro Pro His Phe Pro Ser His Val Ile Lys Ala Thr Phe
1375            1380                1385                1390 gcc tat atc agc aat tgt cat aaa acc aag tta aaa agc att tta gaa       4407
Ala Tyr Ile Ser Asn Cys His Lys Thr Lys Leu Lys Ser Ile Leu Glu
                1395                1400                1405 att ctt tcc aaa agc cct gat tcc tat cag aaa att ctt ctt gcc ata       4455
Ile Leu Ser Lys Ser Pro Asp Ser Tyr Gln Lys Ile Leu Leu Ala Ile
            1410                1415                1420 tgt gag caa gca gct gaa aca aat aat gtt tat aag aag cac aga att       4503
Cys Glu Gln Ala Ala Glu Thr Asn Asn Val Tyr Lys Lys His Arg Ile
        1425                1430                1435
```

-continued

| | |
|---|---|
| ctt aaa ata tat cac ctg ttt gtt agt tta tta ctg aaa gat ata aaa<br>Leu Lys Ile Tyr His Leu Phe Val Ser Leu Leu Leu Lys Asp Ile Lys<br>1440                         1445                      1450 | 4551 |
| agt ggc tta gga gga gct tgg gcc ttt gtt ctt cga gac gtt att tat<br>Ser Gly Leu Gly Gly Ala Trp Ala Phe Val Leu Arg Asp Val Ile Tyr<br>1455                1460                      1465                  1470 | 4599 |
| act ttg att cac tat atc aac caa agg cct tct tgt atc atg gat gtg<br>Thr Leu Ile His Tyr Ile Asn Gln Arg Pro Ser Cys Ile Met Asp Val<br>                  1475                      1480                  1485 | 4647 |
| tca tta cgt agc ttc tcc ctt tgt tgt gac tta tta agt cag gtt tgc<br>Ser Leu Arg Ser Phe Ser Leu Cys Cys Asp Leu Leu Ser Gln Val Cys<br>          1490                     1495                   1500 | 4695 |
| cag aca gcc gtg act tac tgt aag gat gct cta caa aac cat ctt cat<br>Gln Thr Ala Val Thr Tyr Cys Lys Asp Ala Leu Gln Asn His Leu His<br>          1505                     1510                   1515 | 4743 |
| gtt att gtt ggt aca ctt ata ccc ctt gtg tat gag cag gtg gag gtt<br>Val Ile Val Gly Thr Leu Ile Pro Leu Val Tyr Glu Gln Val Glu Val<br>1520                       1525                     1530 | 4791 |
| cag aaa cag gta ttg gac ttg ttg aaa tac tta gtg ata gat aac aag<br>Gln Lys Gln Val Leu Asp Leu Leu Lys Tyr Leu Val Ile Asp Asn Lys<br>1535                        1540                    1545                1550 | 4839 |
| gat aat gaa aac ctc tat atc acg att aag ctt tta gat cct ttt cct<br>Asp Asn Glu Asn Leu Tyr Ile Thr Ile Lys Leu Leu Asp Pro Phe Pro<br>                  1555                     1560                  1565 | 4887 |
| gac cat gtt gtt ttt aag gat ttg cgt att act cag caa aaa atc aaa<br>Asp His Val Val Phe Lys Asp Leu Arg Ile Thr Gln Gln Lys Ile Lys<br>                    1570                   1575                 1580 | 4935 |
| tac agt aga gga ccc ttt tca ctc ttg gag gaa att aac cat ttt ctc<br>Tyr Ser Arg Gly Pro Phe Ser Leu Leu Glu Glu Ile Asn His Phe Leu<br>          1585                     1590                   1595 | 4983 |
| tca gta agt gtt tat gat gca ctt cca ttg aca aga ctt gaa gga cta<br>Ser Val Ser Val Tyr Asp Ala Leu Pro Leu Thr Arg Leu Glu Gly Leu<br>1600                       1605                     1610 | 5031 |
| aag gat ctt cga aga caa ctg gaa cta cat aaa gat cag atg gtg gac<br>Lys Asp Leu Arg Arg Gln Leu Glu Leu His Lys Asp Gln Met Val Asp<br>1615                        1620                    1625                1630 | 5079 |
| att atg aga gct tct cag gat aat ccg caa gat ggg att atg gtg aaa<br>Ile Met Arg Ala Ser Gln Asp Asn Pro Gln Asp Gly Ile Met Val Lys<br>                  1635                     1640                  1645 | 5127 |
| cta gtt gtc aat ttg ttg cag tta tcc aag atg gca ata aac cac act<br>Leu Val Val Asn Leu Leu Gln Leu Ser Lys Met Ala Ile Asn His Thr<br>                    1650                     1655                  1660 | 5175 |
| ggt gaa aaa gaa gtt cta gag gct gtt gga agc tgc ttg gga gaa gtg<br>Gly Glu Lys Glu Val Leu Glu Ala Val Gly Ser Cys Leu Gly Glu Val<br>          1665                     1670                   1675 | 5223 |
| ggt cct ata gat ttc tct acc ata gct ata caa cat agt aaa gat gca<br>Gly Pro Ile Asp Phe Ser Thr Ile Ala Ile Gln His Ser Lys Asp Ala<br>1680                       1685                     1690 | 5271 |
| tct tat acc aag ccc ctt aag tta ttt gaa gat aaa gaa ctt cag tgg<br>Ser Tyr Thr Lys Pro Leu Lys Leu Phe Glu Asp Lys Glu Leu Gln Trp<br>1695                       1700                    1705                1710 | 5319 |
| acc ttc ata atg ctg acc tac ctg aat aac aca ctg gta gaa gat tgt<br>Thr Phe Ile Met Leu Thr Tyr Leu Asn Asn Thr Leu Val Glu Asp Cys<br>                  1715                     1720                  1725 | 5367 |
| gtc aaa gtt cga tca gca gct gtt acc tgt ttg aaa aac att tta gcc<br>Val Lys Val Arg Ser Ala Ala Val Thr Cys Leu Lys Asn Ile Leu Ala<br>                    1730                   1735                 1740 | 5415 |
| aca aag act gga cat agt ttc tgg gag att tat aag atg aca aca gat<br>Thr Lys Thr Gly His Ser Phe Trp Glu Ile Tyr Lys Met Thr Thr Asp<br>          1745                     1750                   1755 | 5463 |

-continued

| | |
|---|---|
| cca atg ctg gcc tat cta cag cct ttt aga aca tca aga aaa aag ttt<br>Pro Met Leu Ala Tyr Leu Gln Pro Phe Arg Thr Ser Arg Lys Lys Phe<br>        1760                  1765                       1770 | 5511 |
| tta gaa gta ccc aga ttt gac aaa gaa aac cct ttt gaa ggc ctg gat<br>Leu Glu Val Pro Arg Phe Asp Lys Glu Asn Pro Phe Glu Gly Leu Asp<br>1775                  1780                      1785                  1790 | 5559 |
| gat ata aat ctg tgg att cct cta agt gaa aat cat gac att tgg ata<br>Asp Ile Asn Leu Trp Ile Pro Leu Ser Glu Asn His Asp Ile Trp Ile<br>                1795                      1800                  1805 | 5607 |
| aag aca ctg act tgt gct ttt ttg gac agt gga ggc aca aaa tgt gaa<br>Lys Thr Leu Thr Cys Ala Phe Leu Asp Ser Gly Gly Thr Lys Cys Glu<br>1810                          1815                        1820 | 5655 |
| att ctt caa tta tta aag cca atg tgt gaa gtg aaa act gac ttt tgt<br>Ile Leu Gln Leu Leu Lys Pro Met Cys Glu Val Lys Thr Asp Phe Cys<br>        1825                        1830                        1835 | 5703 |
| cag act gta ctt cca tac ttg att cat gat att tta ctc caa gat aca<br>Gln Thr Val Leu Pro Tyr Leu Ile His Asp Ile Leu Leu Gln Asp Thr<br>                1840                      1845                  1850 | 5751 |
| aat gaa tca tgg aga aat ctg ctt tct aca cat gtt cag gga ttt ttc<br>Asn Glu Ser Trp Arg Asn Leu Leu Ser Thr His Val Gln Gly Phe Phe<br>1855                      1860                      1865                  1870 | 5799 |
| acc agc tgt ctt cga cac ttc tcg caa acg agc cga tcc aca acc cct<br>Thr Ser Cys Leu Arg His Phe Ser Gln Thr Ser Arg Ser Thr Thr Pro<br>                1875                      1880                  1885 | 5847 |
| gca aac ttg gat tca gag tca gag cac ttt ttc cga tgc tgt ttg gat<br>Ala Asn Leu Asp Ser Glu Ser Glu His Phe Phe Arg Cys Cys Leu Asp<br>                1890                      1895                  1900 | 5895 |
| aaa aaa tca caa aga aca atg ctt gct gtt gtg gac tac atg aga aga<br>Lys Lys Ser Gln Arg Thr Met Leu Ala Val Val Asp Tyr Met Arg Arg<br>        1905                        1910                        1915 | 5943 |
| caa aag aga cct tct tca gga aca att ttt aat gat gct ttc tgg ctg<br>Gln Lys Arg Pro Ser Ser Gly Thr Ile Phe Asn Asp Ala Phe Trp Leu<br>                1920                      1925                  1930 | 5991 |
| gat tta aat tat cta gaa gtt gcc aag gta gct cag tct tgt gct gct<br>Asp Leu Asn Tyr Leu Glu Val Ala Lys Val Ala Gln Ser Cys Ala Ala<br>1935                      1940                      1945                  1950 | 6039 |
| cac ttt aca gct tta ctc tat gca gaa atc tat gca gat aag aaa agt<br>His Phe Thr Ala Leu Leu Tyr Ala Glu Ile Tyr Ala Asp Lys Lys Ser<br>                1955                      1960                  1965 | 6087 |
| atg gat gat caa gag aaa aga agt ctt gca ttt gaa gaa gga agc cag<br>Met Asp Asp Gln Glu Lys Arg Ser Leu Ala Phe Glu Glu Gly Ser Gln<br>        1970                        1975                        1980 | 6135 |
| agt aca act att tct agc ttg agt gaa aaa agt aaa gaa gaa act gga<br>Ser Thr Thr Ile Ser Ser Leu Ser Glu Lys Ser Lys Glu Glu Thr Gly<br>                1985                      1990                  1995 | 6183 |
| ata agt tta cag gat ctt ctc tta gaa atc tac aga agt ata ggg gag<br>Ile Ser Leu Gln Asp Leu Leu Leu Glu Ile Tyr Arg Ser Ile Gly Glu<br>2000                      2005                      2010 | 6231 |
| cca gat agt ttg tat ggc tgt ggt gga ggg aag atg tta caa ccc att<br>Pro Asp Ser Leu Tyr Gly Cys Gly Gly Gly Lys Met Leu Gln Pro Ile<br>2015                      2020                      2025                  2030 | 6279 |
| act aga cta cga aca tat gaa cac gaa gca atg tgg ggc aaa gcc cta<br>Thr Arg Leu Arg Thr Tyr Glu His Glu Ala Met Trp Gly Lys Ala Leu<br>                2035                      2040                  2045 | 6327 |
| gta aca tat gac ctc gaa aca gca atc ccc tca tca aca cgc cag gca<br>Val Thr Tyr Asp Leu Glu Thr Ala Ile Pro Ser Ser Thr Arg Gln Ala<br>                2050                      2055                  2060 | 6375 |
| gga atc att cag gcc ttg cag aat ttg gga ctc tgc cat att ctt tcc<br>Gly Ile Ile Gln Ala Leu Gln Asn Leu Gly Leu Cys His Ile Leu Ser | 6423 |

| | | |
|---|---|---|
| gtc tat tta aaa gga ttg gat tat gaa aat aaa gac tgg tgt cct gaa<br>Val Tyr Leu Lys Gly Leu Asp Tyr Glu Asn Lys Asp Trp Cys Pro Glu<br>　　　2080　　　　　　　　2085　　　　　　　　2090 | | 6471 |
| cta gaa gaa ctt cat tac caa gca gca tgg agg aat atg cag tgg gac<br>Leu Glu Glu Leu His Tyr Gln Ala Ala Trp Arg Asn Met Gln Trp Asp<br>2095　　　　　　　　2100　　　　　　　　2105　　　　　　　　2110 | | 6519 |
| cat tgc act tcc gtc agc aaa gaa gta gaa gga acc agt tac cat gaa<br>His Cys Thr Ser Val Ser Lys Glu Val Glu Gly Thr Ser Tyr His Glu<br>　　　　　　　　2115　　　　　　　　2120　　　　　　　　2125 | | 6567 |
| tca ttg tac aat gct cta caa tct cta aga gac aga gaa ttc tct aca<br>Ser Leu Tyr Asn Ala Leu Gln Ser Leu Arg Asp Arg Glu Phe Ser Thr<br>　　　2130　　　　　　　　2135　　　　　　　　2140 | | 6615 |
| ttt tat gaa agt ctc aaa tat gcc aga gta aaa gaa gtg gaa gag atg<br>Phe Tyr Glu Ser Leu Lys Tyr Ala Arg Val Lys Glu Val Glu Glu Met<br>2145　　　　　　　　2150　　　　　　　　2155 | | 6663 |
| tgt aag cgc agc ctt gag tct gtg tat tcg ctc tat ccc aca ctt agc<br>Cys Lys Arg Ser Leu Glu Ser Val Tyr Ser Leu Tyr Pro Thr Leu Ser<br>　　　2160　　　　　　　　2165　　　　　　　　2170 | | 6711 |
| agg ttg cag gcc att gga gag ctg gaa agc att ggg gag ctt ttc tca<br>Arg Leu Gln Ala Ile Gly Glu Leu Glu Ser Ile Gly Glu Leu Phe Ser<br>2175　　　　　　　　2180　　　　　　　　2185　　　　　　　　2190 | | 6759 |
| aga tca gtc aca cat aga caa ctc tct gaa gta tat att aag tgg cag<br>Arg Ser Val Thr His Arg Gln Leu Ser Glu Val Tyr Ile Lys Trp Gln<br>　　　　　　　　2195　　　　　　　　2200　　　　　　　　2205 | | 6807 |
| aaa cac tcc cag ctt ctc aag gac agt gat ttt agt ttt cag gag cct<br>Lys His Ser Gln Leu Leu Lys Asp Ser Asp Phe Ser Phe Gln Glu Pro<br>　　　2210　　　　　　　　2215　　　　　　　　2220 | | 6855 |
| atc atg gct cta cgc aca gtc att ttg gag atc ctg atg gaa aag gaa<br>Ile Met Ala Leu Arg Thr Val Ile Leu Glu Ile Leu Met Glu Lys Glu<br>2225　　　　　　　　2230　　　　　　　　2235 | | 6903 |
| atg gac aac tca caa aga gaa tgt att aag gac att ctc acc aaa cac<br>Met Asp Asn Ser Gln Arg Glu Cys Ile Lys Asp Ile Leu Thr Lys His<br>　　　2240　　　　　　　　2245　　　　　　　　2250 | | 6951 |
| ctt gta gaa ctc tct ata ctg gcc aga act ttc aag aac act cag ctc<br>Leu Val Glu Leu Ser Ile Leu Ala Arg Thr Phe Lys Asn Thr Gln Leu<br>2255　　　　　　　　2260　　　　　　　　2265　　　　　　　　2270 | | 6999 |
| cct gaa agg gca ata ttt caa att aaa cag tac aat tca gtt agc tgt<br>Pro Glu Arg Ala Ile Phe Gln Ile Lys Gln Tyr Asn Ser Val Ser Cys<br>　　　　　　　　2275　　　　　　　　2280　　　　　　　　2285 | | 7047 |
| gga gtc tct gag tgg cag ctg gaa gaa gca caa gta ttc tgg gca aaa<br>Gly Val Ser Glu Trp Gln Leu Glu Glu Ala Gln Val Phe Trp Ala Lys<br>　　　2290　　　　　　　　2295　　　　　　　　2300 | | 7095 |
| aag gag cag agt ctt gcc ctg agt att ctc aag caa atg atc aag aag<br>Lys Glu Gln Ser Leu Ala Leu Ser Ile Leu Lys Gln Met Ile Lys Lys<br>2305　　　　　　　　2310　　　　　　　　2315 | | 7143 |
| ttg gat gcc agc tgt gca gcg aac aat ccc agc cta aaa ctt aca tac<br>Leu Asp Ala Ser Cys Ala Ala Asn Asn Pro Ser Leu Lys Leu Thr Tyr<br>　　　2320　　　　　　　　2325　　　　　　　　2330 | | 7191 |
| aca gaa tgt ctg agg gtt tgt ggc aac tgg tta gca gaa acg tgc tta<br>Thr Glu Cys Leu Arg Val Cys Gly Asn Trp Leu Ala Glu Thr Cys Leu<br>2335　　　　　　　　2340　　　　　　　　2345　　　　　　　　2350 | | 7239 |
| gaa aat cct gcg gtc atc atg cag acc tat cta gaa aag gca gta gaa<br>Glu Asn Pro Ala Val Ile Met Gln Thr Tyr Leu Glu Lys Ala Val Glu<br>　　　　　　　　2355　　　　　　　　2360　　　　　　　　2365 | | 7287 |
| gtt gct gga aat tat gat gga gaa agt agt gat gag cta aga aat gga<br>Val Ala Gly Asn Tyr Asp Gly Glu Ser Ser Asp Glu Leu Arg Asn Gly<br>　　　2370　　　　　　　　2375　　　　　　　　2380 | | 7335 |
| aaa atg aag gca ttt ctc tca tta gcc cgg ttt tca gat act caa tac | | 7383 |

```
                Lys Met Lys Ala Phe Leu Ser Leu Ala Arg Phe Ser Asp Thr Gln Tyr
                    2385                2390                2395 caa aga att gaa aac tac atg aaa tca tcg gaa ttt gaa aac aag caa           7431
Gln Arg Ile Glu Asn Tyr Met Lys Ser Ser Glu Phe Glu Asn Lys Gln
    2400                2405                2410 gct ctc ctg aaa aga gcc aaa gag gaa gta ggt ctc ctt agg gaa cat           7479
Ala Leu Leu Lys Arg Ala Lys Glu Glu Val Gly Leu Leu Arg Glu His
2415                2420                2425                2430 aaa att cag aca aac aga tac aca gta aag gtt cag cga gag ctg gag           7527
Lys Ile Gln Thr Asn Arg Tyr Thr Val Lys Val Gln Arg Glu Leu Glu
                2435                2440                2445 ttg gat gaa tta gcc ctg cgt gca ctg aaa gag gat cgt aaa cgc ttc           7575
Leu Asp Glu Leu Ala Leu Arg Ala Leu Lys Glu Asp Arg Lys Arg Phe
            2450                2455                2460 tta tgt aaa gca gtt gaa aat tat atc aac tgc tta tta agt gga gaa           7623
Leu Cys Lys Ala Val Glu Asn Tyr Ile Asn Cys Leu Leu Ser Gly Glu
        2465                2470                2475 gaa cat gat atg tgg gta ttc cgg ctt tgt tcc ctc tgg ctt gaa aat           7671
Glu His Asp Met Trp Val Phe Arg Leu Cys Ser Leu Trp Leu Glu Asn
    2480                2485                2490 tct cga gtt tct gaa gtc aat ggc atg atg aag aga gac gga atg aag           7719
Ser Arg Val Ser Glu Val Asn Gly Met Met Lys Arg Asp Gly Met Lys
2495                2500                2505                2510 att cca aca tat aaa ttt ttg cct ctt atg tac caa ttg gct gct aga           7767
Ile Pro Thr Tyr Lys Phe Leu Pro Leu Met Tyr Gln Leu Ala Ala Arg
                2515                2520                2525 atg ggg acc aag atg atg gga ggc cta gga ttt cat gaa gtc ctc aat           7815
Met Gly Thr Lys Met Met Gly Gly Leu Gly Phe His Glu Val Leu Asn
            2530                2535                2540 aat cta atc tct aga att tca atg gat cac ccc cat cac act ttg ttt           7863
Asn Leu Ile Ser Arg Ile Ser Met Asp His Pro His His Thr Leu Phe
        2545                2550                2555 att ata ctg gcc tta gca aat gca aac aga gat gaa ttt ctg act aaa           7911
Ile Ile Leu Ala Leu Ala Asn Ala Asn Arg Asp Glu Phe Leu Thr Lys
    2560                2565                2570 cca gag gta gcc aga aga agc aga ata act aaa aat gtg cct aaa caa           7959
Pro Glu Val Ala Arg Arg Ser Arg Ile Thr Lys Asn Val Pro Lys Gln
2575                2580                2585                2590 agc tct cag ctt gat gag gat cga aca gag gct gca aat aga ata ata           8007
Ser Ser Gln Leu Asp Glu Asp Arg Thr Glu Ala Ala Asn Arg Ile Ile
                2595                2600                2605 tgt act atc aga agt agg aga cct cag atg gtc aga agt gtt gag gca           8055
Cys Thr Ile Arg Ser Arg Arg Pro Gln Met Val Arg Ser Val Glu Ala
            2610                2615                2620 ctt tgt gat gct tat att ata tta gca aac tta gat gcc act cag tgg           8103
Leu Cys Asp Ala Tyr Ile Ile Leu Ala Asn Leu Asp Ala Thr Gln Trp
        2625                2630                2635 aag act cag aga aaa ggc ata aat att cca gca gac cag cca att act           8151
Lys Thr Gln Arg Lys Gly Ile Asn Ile Pro Ala Asp Gln Pro Ile Thr
    2640                2645                2650 aaa ctt aag aat tta gaa gat gtt gtt gtc cct act atg gaa att aag           8199
Lys Leu Lys Asn Leu Glu Asp Val Val Val Pro Thr Met Glu Ile Lys
2655                2660                2665                2670 gtg gac cac aca gga gaa tat gga aat ctg gtg act ata cag tca ttt           8247
Val Asp His Thr Gly Glu Tyr Gly Asn Leu Val Thr Ile Gln Ser Phe
                2675                2680                2685 aaa gca gaa ttt cgc tta gca gga ggt gta aat tta cca aaa ata ata           8295
Lys Ala Glu Phe Arg Leu Ala Gly Gly Val Asn Leu Pro Lys Ile Ile
            2690                2695                2700 gat tgt gta ggt tcc gat ggc aag gag agg aga cag ctt gtt aag ggc           8343
```

-continued

```
                Asp Cys Val Gly Ser Asp Gly Lys Glu Arg Arg Gln Leu Val Lys Gly
                        2705                2710                2715 cgt gat gac ctg aga caa gat gct gtc atg caa cag gtc ttc cag atg           8391
Arg Asp Asp Leu Arg Gln Asp Ala Val Met Gln Gln Val Phe Gln Met
        2720                2725                2730 tgt aat aca tta ctg cag aga aac acg gaa act agg aag agg aaa tta           8439
Cys Asn Thr Leu Leu Gln Arg Asn Thr Glu Thr Arg Lys Arg Lys Leu
2735                2740                2745                2750 act atc tgt act tat aag gtg gtt ccc ctc tct cag cga agt ggt gtt           8487
Thr Ile Cys Thr Tyr Lys Val Val Pro Leu Ser Gln Arg Ser Gly Val
            2755                2760                2765 ctt gaa tgg tgc aca gga act gtc ccc att ggt gaa ttt ctt gtt aac           8535
Leu Glu Trp Cys Thr Gly Thr Val Pro Ile Gly Glu Phe Leu Val Asn
                2770                2775                2780 aat gaa gat ggt gct cat aaa aga tac agg cca aat gat ttc agt gcc           8583
Asn Glu Asp Gly Ala His Lys Arg Tyr Arg Pro Asn Asp Phe Ser Ala
2785                2790                2795 ttt cag tgc caa aag aaa atg atg gag gtg caa aaa aag tct ttt gaa           8631
Phe Gln Cys Gln Lys Lys Met Met Glu Val Gln Lys Lys Ser Phe Glu
        2800                2805                2810 gag aaa tat gaa gtc ttc atg gat gtt tgc caa aat ttt caa cca gtt           8679
Glu Lys Tyr Glu Val Phe Met Asp Val Cys Gln Asn Phe Gln Pro Val
2815                2820                2825                2830 ttc cgt tac ttc tgc atg gaa aaa ttc ttg gat cca gct att tgg ttt           8727
Phe Arg Tyr Phe Cys Met Glu Lys Phe Leu Asp Pro Ala Ile Trp Phe
            2835                2840                2845 gag aag cga ttg gct tat acg cgc agt gta gct act tct tct att gtt           8775
Glu Lys Arg Leu Ala Tyr Thr Arg Ser Val Ala Thr Ser Ser Ile Val
                2850                2855                2860 ggt tac ata ctt gga ctt ggt gat aga cat gta cag aat atc ttg ata           8823
Gly Tyr Ile Leu Gly Leu Gly Asp Arg His Val Gln Asn Ile Leu Ile
2865                2870                2875 aat gag cag tca gca gaa ctt gta cat ata gat cta ggt gtt gct ttt           8871
Asn Glu Gln Ser Ala Glu Leu Val His Ile Asp Leu Gly Val Ala Phe
        2880                2885                2890 gaa cag ggc aaa atc ctt cct act cct gag aca gtt cct ttt aga ctc           8919
Glu Gln Gly Lys Ile Leu Pro Thr Pro Glu Thr Val Pro Phe Arg Leu
2895                2900                2905                2910 acc aga gat att gtg gat ggc atg ggc att acg ggt gtt gaa ggt gtc           8967
Thr Arg Asp Ile Val Asp Gly Met Gly Ile Thr Gly Val Glu Gly Val
            2915                2920                2925 ttc aga aga tgc tgt gag aaa acc atg gaa gtg atg aga aac tct cag           9015
Phe Arg Arg Cys Cys Glu Lys Thr Met Glu Val Met Arg Asn Ser Gln
                2930                2935                2940 gaa act ctg tta acc att gta gag gtc ctt cta tat gat cca ctc ttt           9063
Glu Thr Leu Leu Thr Ile Val Glu Val Leu Leu Tyr Asp Pro Leu Phe
2945                2950                2955 gac tgg acc atg aat cct ttg aaa gct ttg tat tta cag cag agg ccg           9111
Asp Trp Thr Met Asn Pro Leu Lys Ala Leu Tyr Leu Gln Gln Arg Pro
        2960                2965                2970 gaa gat gaa act gag ctt cac cct act ctg aat gca gat gac caa gaa           9159
Glu Asp Glu Thr Glu Leu His Pro Thr Leu Asn Ala Asp Asp Gln Glu
2975                2980                2985                2990 tgc aaa cga aat ctc agt gat att gac cag agt ttc gac aaa gta gct           9207
Cys Lys Arg Asn Leu Ser Asp Ile Asp Gln Ser Phe Asp Lys Val Ala
            2995                3000                3005 gaa cgt gtc tta atg aga cta caa gag aaa ctg aaa gga gtg gaa gaa           9255
Glu Arg Val Leu Met Arg Leu Gln Glu Lys Leu Lys Gly Val Glu Glu
                3010                3015                3020
```

```
ggc act gtg ctc agt gtt ggt gga cag gtg aat ttg ctc ata cag cag     9303
Gly Thr Val Leu Ser Val Gly Gly Gln Val Asn Leu Leu Ile Gln Gln
        3025                3030                3035 gcc ata gac ccc aaa aat ctc agc cga ctt ttc cca gga tgg aaa gct     9351
Ala Ile Asp Pro Lys Asn Leu Ser Arg Leu Phe Pro Gly Trp Lys Ala
3040                3045                3050 tgg gtg tgatcttcag tatatgaatt acccttc                               9385
Trp Val
3055
```

<210> SEQ ID NO 2
<211> LENGTH: 3056
<212> TYPE: PRT
<213> ORGANISM: Human

<400> SEQUENCE: 2

```
Met Ser Leu Val Leu Asn Asp Leu Leu Ile Cys Cys Arg Gln Leu Glu
1               5                   10                  15

His Asp Arg Ala Thr Glu Arg Lys Lys Glu Val Glu Lys Phe Lys Arg
            20                  25                  30

Leu Ile Arg Asp Pro Glu Thr Ile Lys His Leu Asp Arg His Ser Asp
        35                  40                  45

Ser Lys Gln Gly Lys Tyr Leu Asn Trp Asp Ala Val Phe Arg Phe Leu
    50                  55                  60

Gln Lys Tyr Ile Gln Lys Glu Thr Glu Cys Leu Arg Ile Ala Lys Pro
65                  70                  75                  80

Asn Val Ser Ala Ser Thr Gln Ala Ser Arg Gln Lys Lys Met Gln Glu
                85                  90                  95

Ile Ser Ser Leu Val Lys Tyr Phe Ile Lys Cys Ala Asn Arg Arg Ala
            100                 105                 110

Pro Arg Leu Lys Cys Gln Glu Leu Leu Asn Tyr Ile Met Asp Thr Val
        115                 120                 125

Lys Asp Ser Ser Asn Gly Ala Ile Tyr Gly Ala Asp Cys Ser Asn Ile
    130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Arg Ile Ile His
            180                 185                 190

Ala Val Thr Lys Gly Cys Cys Ser Gln Thr Asp Gly Leu Asn Ser Lys
        195                 200                 205

Phe Leu Asp Phe Phe Ser Lys Ala Ile Gln Cys Ala Arg Gln Glu Lys
    210                 215                 220

Ser Ser Ser Gly Leu Asn His Ile Leu Ala Ala Leu Thr Ile Phe Leu
225                 230                 235                 240

Lys Thr Leu Ala Val Asn Phe Arg Ile Arg Val Cys Glu Leu Gly Asp
                245                 250                 255

Glu Ile Leu Pro Thr Leu Leu Tyr Ile Trp Thr Gln His Arg Leu Asn
            260                 265                 270

Asp Ser Leu Lys Glu Val Ile Ile Glu Leu Phe Gln Leu Gln Ile Tyr
        275                 280                 285

Ile His His Pro Lys Gly Ala Lys Thr Gln Glu Lys Gly Ala Tyr Glu
    290                 295                 300

Ser Thr Lys Trp Arg Ser Ile Leu Tyr Asn Leu Tyr Asp Leu Leu Val
305                 310                 315                 320
```

```
Asn Glu Ile Ser His Ile Gly Ser Arg Gly Lys Tyr Ser Ser Gly Phe
            325                 330                 335
Arg Asn Ile Ala Val Lys Glu Asn Leu Ile Glu Leu Met Ala Asp Ile
            340                 345                 350
Cys His Gln Val Phe Asn Glu Asp Thr Arg Ser Leu Glu Ile Ser Gln
            355                 360                 365
Ser Tyr Thr Thr Thr Gln Arg Glu Ser Ser Asp Tyr Ser Val Pro Cys
    370                 375                 380
Lys Arg Lys Lys Ile Glu Leu Gly Trp Glu Val Ile Lys Asp His Leu
385                 390                 395                 400
Gln Lys Ser Gln Asn Asp Phe Asp Leu Val Pro Trp Leu Gln Ile Ala
                405                 410                 415
Thr Gln Leu Ile Ser Lys Tyr Pro Ala Ser Leu Pro Asn Cys Glu Leu
            420                 425                 430
Ser Pro Leu Leu Met Ile Leu Ser Gln Leu Leu Pro Gln Gln Arg His
            435                 440                 445
Gly Glu Arg Thr Pro Tyr Val Leu Arg Cys Leu Thr Glu Val Ala Leu
    450                 455                 460
Cys Gln Asp Lys Arg Ser Asn Leu Glu Ser Ser Gln Lys Ser Asp Leu
465                 470                 475                 480
Leu Lys Leu Trp Asn Lys Ile Trp Cys Ile Thr Phe Arg Gly Ile Ser
                485                 490                 495
Ser Glu Gln Ile Gln Ala Glu Asn Phe Gly Leu Leu Gly Ala Ile Ile
            500                 505                 510
Gln Gly Ser Leu Val Glu Val Asp Arg Glu Phe Trp Lys Leu Phe Thr
            515                 520                 525
Gly Ser Ala Cys Arg Pro Ser Cys Pro Ala Val Cys Cys Leu Thr Leu
    530                 535                 540
Ala Leu Thr Thr Ser Ile Val Pro Gly Ala Val Lys Met Gly Ile Glu
545                 550                 555                 560
Gln Asn Met Cys Glu Val Asn Arg Ser Phe Ser Leu Lys Glu Ser Ile
                565                 570                 575
Met Lys Trp Leu Leu Phe Tyr Gln Leu Glu Gly Asp Leu Glu Asn Ser
            580                 585                 590
Thr Glu Val Pro Pro Ile Leu His Ser Asn Phe Pro His Leu Val Leu
            595                 600                 605
Glu Lys Ile Leu Val Ser Leu Thr Met Lys Asn Cys Lys Ala Ala Met
    610                 615                 620
Asn Phe Phe Gln Ser Val Pro Glu Cys Glu His His Gln Lys Asp Lys
625                 630                 635                 640
Glu Glu Leu Ser Phe Ser Glu Val Glu Leu Phe Leu Gln Thr Thr
                645                 650                 655
Phe Asp Lys Met Asp Phe Leu Thr Ile Val Arg Glu Cys Gly Ile Glu
            660                 665                 670
Lys His Gln Ser Ser Ile Gly Phe Ser Val His Gln Asn Leu Lys Glu
            675                 680                 685
Ser Leu Asp Arg Cys Leu Leu Gly Leu Ser Glu Gln Leu Leu Asn Asn
    690                 695                 700
Tyr Ser Ser Glu Ile Thr Asn Ser Glu Thr Leu Val Arg Cys Ser Arg
705                 710                 715                 720
Leu Leu Val Gly Val Leu Gly Cys Tyr Cys Tyr Met Gly Val Ile Ala
                725                 730                 735
```

```
Glu Glu Glu Ala Tyr Lys Ser Glu Leu Phe Gln Lys Ala Asn Ser Leu
            740                 745                 750

Met Gln Cys Ala Gly Glu Ser Ile Thr Leu Phe Lys Asn Lys Thr Asn
            755                 760                 765

Glu Glu Phe Arg Ile Gly Ser Leu Arg Asn Met Met Gln Leu Cys Thr
            770                 775                 780

Arg Cys Leu Ser Asn Cys Thr Lys Lys Ser Pro Asn Lys Ile Ala Ser
785                 790                 795                 800

Gly Phe Phe Leu Arg Leu Leu Thr Ser Lys Leu Met Asn Asp Ile Ala
                805                 810                 815

Asp Ile Cys Lys Ser Leu Ala Ser Phe Ile Lys Lys Pro Phe Asp Arg
                820                 825                 830

Gly Glu Val Glu Ser Met Glu Asp Asp Thr Asn Gly Asn Leu Met Glu
                835                 840                 845

Val Glu Asp Gln Ser Ser Met Asn Leu Phe Asn Asp Tyr Pro Asp Ser
            850                 855                 860

Ser Val Ser Asp Ala Asn Glu Pro Gly Glu Ser Gln Ser Thr Ile Gly
865                 870                 875                 880

Ala Ile Asn Pro Leu Ala Glu Glu Tyr Leu Ser Lys Gln Asp Leu Leu
                885                 890                 895

Phe Leu Asp Met Leu Lys Phe Leu Cys Leu Cys Val Thr Thr Ala Gln
                900                 905                 910

Thr Asn Thr Val Ser Phe Arg Ala Ala Asp Ile Arg Arg Lys Leu Leu
                915                 920                 925

Met Leu Ile Asp Ser Ser Thr Leu Glu Pro Thr Lys Ser Leu His Leu
            930                 935                 940

His Met Tyr Leu Met Leu Leu Lys Glu Leu Pro Gly Glu Glu Tyr Pro
945                 950                 955                 960

Leu Pro Met Glu Asp Val Leu Glu Leu Leu Lys Pro Leu Ser Asn Val
                965                 970                 975

Cys Ser Leu Tyr Arg Arg Asp Gln Asp Val Cys Lys Thr Ile Leu Asn
                980                 985                 990

His Val Leu His Val Val Lys Asn Leu Gly Gln Ser Asn Met Asp Ser
            995                 1000                1005

Glu Asn Thr Arg Asp Ala Gln Gly Gln Phe Leu Thr Val Ile Gly Ala
            1010                1015                1020

Phe Trp His Leu Thr Lys Glu Arg Lys Tyr Ile Phe Ser Val Arg Met
1025                1030                1035                1040

Ala Leu Val Asn Cys Leu Lys Thr Leu Leu Glu Ala Asp Pro Tyr Ser
                1045                1050                1055

Lys Trp Ala Ile Leu Asn Val Met Gly Lys Asp Phe Pro Val Asn Glu
                1060                1065                1070

Val Phe Thr Gln Phe Leu Ala Asp Asn His His Gln Val Arg Met Leu
            1075                1080                1085

Ala Ala Glu Ser Ile Asn Arg Leu Phe Gln Asp Thr Lys Gly Asp Ser
            1090                1095                1100

Ser Arg Leu Leu Lys Ala Leu Pro Leu Lys Leu Gln Gln Thr Ala Phe
1105                1110                1115                1120

Glu Asn Ala Tyr Leu Lys Ala Gln Glu Gly Met Arg Glu Met Ser His
                1125                1130                1135

Ser Ala Glu Asn Pro Glu Thr Leu Asp Glu Ile Tyr Asn Arg Lys Ser
                1140                1145                1150

Val Leu Leu Thr Leu Ile Ala Val Val Leu Ser Cys Ser Pro Ile Cys
```

-continued

```
                1155                1160                1165
Glu Lys Gln Ala Leu Phe Ala Leu Cys Lys Ser Val Lys Glu Asn Gly
    1170                1175                1180
Leu Glu Pro His Leu Val Lys Lys Val Leu Glu Lys Val Ser Glu Thr
1185                1190                1195                1200
Phe Gly Tyr Arg Arg Leu Glu Asp Phe Met Ala Ser His Leu Asp Tyr
                1205                1210                1215
Leu Val Leu Glu Trp Leu Asn Leu Gln Asp Thr Glu Tyr Asn Leu Ser
            1220                1225                1230
Ser Phe Pro Phe Ile Leu Leu Asn Tyr Thr Asn Ile Glu Asp Phe Tyr
        1235                1240                1245
Arg Ser Cys Tyr Lys Val Leu Ile Pro His Leu Val Ile Arg Ser His
    1250                1255                1260
Phe Asp Glu Val Lys Ser Ile Ala Asn Gln Ile Gln Glu Asp Trp Lys
1265                1270                1275                1280
Ser Leu Leu Thr Asp Cys Phe Pro Lys Ile Leu Val Asn Ile Leu Pro
                1285                1290                1295
Tyr Phe Ala Tyr Glu Gly Thr Arg Asp Ser Gly Met Ala Gln Gln Arg
                1300                1305                1310
Glu Thr Ala Thr Lys Val Tyr Asp Met Leu Lys Ser Glu Asn Leu Leu
            1315                1320                1325
Gly Lys Gln Ile Asp His Leu Phe Ile Ser Asn Leu Pro Glu Ile Val
        1330                1335                1340
Val Glu Leu Leu Met Thr Leu His Glu Pro Ala Asn Ser Ser Ala Ser
1345                1350                1355                1360
Gln Ser Thr Asp Leu Cys Asp Phe Ser Gly Asp Leu Asp Pro Ala Pro
                1365                1370                1375
Asn Pro Pro His Phe Pro Ser His Val Ile Lys Ala Thr Phe Ala Tyr
            1380                1385                1390
Ile Ser Asn Cys His Lys Thr Lys Leu Lys Ser Ile Leu Glu Ile Leu
        1395                1400                1405
Ser Lys Ser Pro Asp Ser Tyr Gln Lys Ile Leu Leu Ala Ile Cys Glu
    1410                1415                1420
Gln Ala Ala Glu Thr Asn Asn Val Tyr Lys Lys His Arg Ile Leu Lys
1425                1430                1435                1440
Ile Tyr His Leu Phe Val Ser Leu Leu Leu Lys Asp Ile Lys Ser Gly
                1445                1450                1455
Leu Gly Gly Ala Trp Ala Phe Val Leu Arg Asp Val Ile Tyr Thr Leu
            1460                1465                1470
Ile His Tyr Ile Asn Gln Arg Pro Ser Cys Ile Met Asp Val Ser Leu
        1475                1480                1485
Arg Ser Phe Ser Leu Cys Cys Asp Leu Leu Ser Gln Val Cys Gln Thr
    1490                1495                1500
Ala Val Thr Tyr Cys Lys Asp Ala Leu Gln Asn His Leu His Val Ile
1505                1510                1515                1520
Val Gly Thr Leu Ile Pro Leu Val Tyr Glu Gln Val Glu Val Gln Lys
                1525                1530                1535
Gln Val Leu Asp Leu Leu Lys Tyr Leu Val Ile Asp Asn Lys Asp Asn
            1540                1545                1550
Glu Asn Leu Tyr Ile Thr Ile Lys Leu Leu Asp Pro Phe Pro Asp His
        1555                1560                1565
Val Val Phe Lys Asp Leu Arg Ile Thr Gln Gln Lys Ile Lys Tyr Ser
    1570                1575                1580
```

-continued

```
Arg Gly Pro Phe Ser Leu Leu Glu Glu Ile Asn His Phe Leu Ser Val
1585                1590                1595                1600

Ser Val Tyr Asp Ala Leu Pro Leu Thr Arg Leu Glu Gly Leu Lys Asp
                1605                1610                1615

Leu Arg Arg Gln Leu Glu Leu His Lys Asp Gln Met Val Asp Ile Met
            1620                1625                1630

Arg Ala Ser Gln Asp Asn Pro Gln Asp Gly Ile Met Val Lys Leu Val
        1635                1640                1645

Val Asn Leu Leu Gln Leu Ser Lys Met Ala Ile Asn His Thr Gly Glu
    1650                1655                1660

Lys Glu Val Leu Glu Ala Val Gly Ser Cys Leu Gly Glu Val Gly Pro
1665                1670                1675                1680

Ile Asp Phe Ser Thr Ile Ala Ile Gln His Ser Lys Asp Ala Ser Tyr
                1685                1690                1695

Thr Lys Pro Leu Lys Leu Phe Glu Asp Lys Glu Leu Gln Trp Thr Phe
            1700                1705                1710

Ile Met Leu Thr Tyr Leu Asn Asn Thr Leu Val Glu Asp Cys Val Lys
        1715                1720                1725

Val Arg Ser Ala Ala Val Thr Cys Leu Lys Asn Ile Leu Ala Thr Lys
    1730                1735                1740

Thr Gly His Ser Phe Trp Glu Ile Tyr Lys Met Thr Thr Asp Pro Met
1745                1750                1755                1760

Leu Ala Tyr Leu Gln Pro Phe Arg Thr Ser Arg Lys Lys Phe Leu Glu
                1765                1770                1775

Val Pro Arg Phe Asp Lys Glu Asn Pro Phe Glu Gly Leu Asp Asp Ile
            1780                1785                1790

Asn Leu Trp Ile Pro Leu Ser Glu Asn His Asp Ile Trp Ile Lys Thr
        1795                1800                1805

Leu Thr Cys Ala Phe Leu Asp Ser Gly Gly Thr Lys Cys Glu Ile Leu
    1810                1815                1820

Gln Leu Leu Lys Pro Met Cys Glu Val Lys Thr Asp Phe Cys Gln Thr
1825                1830                1835                1840

Val Leu Pro Tyr Leu Ile His Asp Ile Leu Leu Gln Asp Thr Asn Glu
                1845                1850                1855

Ser Trp Arg Asn Leu Leu Ser Thr His Val Gln Gly Phe Phe Thr Ser
            1860                1865                1870

Cys Leu Arg His Phe Ser Gln Thr Ser Arg Ser Thr Thr Pro Ala Asn
        1875                1880                1885

Leu Asp Ser Glu Ser Glu His Phe Phe Arg Cys Cys Leu Asp Lys Lys
    1890                1895                1900

Ser Gln Arg Thr Met Leu Ala Val Val Asp Tyr Met Arg Arg Gln Lys
1905                1910                1915                1920

Arg Pro Ser Ser Gly Thr Ile Phe Asn Asp Ala Phe Trp Leu Asp Leu
                1925                1930                1935

Asn Tyr Leu Glu Val Ala Lys Val Ala Gln Ser Cys Ala Ala His Phe
            1940                1945                1950

Thr Ala Leu Leu Tyr Ala Glu Ile Tyr Ala Asp Lys Lys Ser Met Asp
        1955                1960                1965

Asp Gln Glu Lys Arg Ser Leu Ala Phe Glu Glu Gly Ser Gln Ser Thr
    1970                1975                1980

Thr Ile Ser Ser Leu Ser Glu Lys Ser Lys Glu Glu Thr Gly Ile Ser
1985                1990                1995                2000
```

-continued

```
Leu Gln Asp Leu Leu Glu Ile Tyr Arg Ser Ile Gly Glu Pro Asp
            2005                2010                2015

Ser Leu Tyr Gly Cys Gly Gly Lys Met Leu Gln Pro Ile Thr Arg
            2020                2025                2030

Leu Arg Thr Tyr Glu His Glu Ala Met Trp Gly Lys Ala Leu Val Thr
            2035                2040                2045

Tyr Asp Leu Glu Thr Ala Ile Pro Ser Ser Thr Arg Gln Ala Gly Ile
            2050                2055                2060

Ile Gln Ala Leu Gln Asn Leu Gly Leu Cys His Ile Leu Ser Val Tyr
2065            2070                2075                2080

Leu Lys Gly Leu Asp Tyr Glu Asn Lys Asp Trp Cys Pro Glu Leu Glu
            2085                2090                2095

Glu Leu His Tyr Gln Ala Ala Trp Arg Asn Met Gln Trp Asp His Cys
            2100                2105                2110

Thr Ser Val Ser Lys Glu Val Glu Gly Thr Ser Tyr His Glu Ser Leu
            2115                2120                2125

Tyr Asn Ala Leu Gln Ser Leu Arg Asp Arg Glu Phe Ser Thr Phe Tyr
            2130                2135                2140

Glu Ser Leu Lys Tyr Ala Arg Val Lys Glu Val Glu Glu Met Cys Lys
2145            2150                2155                2160

Arg Ser Leu Glu Ser Val Tyr Ser Leu Tyr Pro Thr Leu Ser Arg Leu
            2165                2170                2175

Gln Ala Ile Gly Glu Leu Glu Ser Ile Gly Glu Leu Phe Ser Arg Ser
            2180                2185                2190

Val Thr His Arg Gln Leu Ser Glu Val Tyr Ile Lys Trp Gln Lys His
            2195                2200                2205

Ser Gln Leu Leu Lys Asp Ser Asp Phe Ser Phe Gln Glu Pro Ile Met
            2210                2215                2220

Ala Leu Arg Thr Val Ile Leu Glu Ile Leu Met Glu Lys Glu Met Asp
2225            2230                2235                2240

Asn Ser Gln Arg Glu Cys Ile Lys Asp Ile Leu Thr Lys His Leu Val
            2245                2250                2255

Glu Leu Ser Ile Leu Ala Arg Thr Phe Lys Asn Thr Gln Leu Pro Glu
            2260                2265                2270

Arg Ala Ile Phe Gln Ile Lys Gln Tyr Asn Ser Val Ser Cys Gly Val
            2275                2280                2285

Ser Glu Trp Gln Leu Glu Glu Ala Gln Val Phe Trp Ala Lys Lys Glu
            2290                2295                2300

Gln Ser Leu Ala Leu Ser Ile Leu Lys Gln Met Ile Lys Lys Leu Asp
2305            2310                2315                2320

Ala Ser Cys Ala Ala Asn Asn Pro Ser Leu Lys Leu Thr Tyr Thr Glu
            2325                2330                2335

Cys Leu Arg Val Cys Gly Asn Trp Leu Ala Glu Thr Cys Leu Glu Asn
            2340                2345                2350

Pro Ala Val Ile Met Gln Thr Tyr Leu Glu Lys Ala Val Glu Val Ala
            2355                2360                2365

Gly Asn Tyr Asp Gly Glu Ser Ser Asp Glu Leu Arg Asn Gly Lys Met
            2370                2375                2380

Lys Ala Phe Leu Ser Leu Ala Arg Phe Ser Asp Thr Gln Tyr Gln Arg
2385            2390                2395                2400

Ile Glu Asn Tyr Met Lys Ser Ser Glu Phe Glu Asn Lys Gln Ala Leu
            2405                2410                2415

Leu Lys Arg Ala Lys Glu Glu Val Gly Leu Leu Arg Glu His Lys Ile
```

-continued

```
                2420                2425                2430
Gln Thr Asn Arg Tyr Thr Val Lys Val Gln Arg Glu Leu Glu Leu Asp
            2435                2440                2445
Glu Leu Ala Leu Arg Ala Leu Lys Glu Asp Arg Lys Arg Phe Leu Cys
        2450                2455                2460
Lys Ala Val Glu Asn Tyr Ile Asn Cys Leu Leu Ser Gly Glu Glu His
2465                2470                2475                2480
Asp Met Trp Val Phe Arg Leu Cys Ser Leu Trp Leu Glu Asn Ser Arg
                2485                2490                2495
Val Ser Glu Val Asn Gly Met Met Lys Arg Asp Gly Met Lys Ile Pro
            2500                2505                2510
Thr Tyr Lys Phe Leu Pro Leu Met Tyr Gln Leu Ala Ala Arg Met Gly
        2515                2520                2525
Thr Lys Met Met Gly Gly Leu Gly Phe His Glu Val Leu Asn Asn Leu
2530                2535                2540
Ile Ser Arg Ile Ser Met Asp His Pro His Thr Leu Phe Ile Ile
2545                2550                2555                2560
Leu Ala Leu Ala Asn Ala Asn Arg Asp Glu Phe Leu Thr Lys Pro Glu
                2565                2570                2575
Val Ala Arg Arg Ser Arg Ile Thr Lys Asn Val Pro Lys Gln Ser Ser
            2580                2585                2590
Gln Leu Asp Glu Asp Arg Thr Glu Ala Ala Asn Arg Ile Ile Cys Thr
        2595                2600                2605
Ile Arg Ser Arg Arg Pro Gln Met Val Arg Ser Val Glu Ala Leu Cys
2610                2615                2620
Asp Ala Tyr Ile Ile Leu Ala Asn Leu Asp Ala Thr Gln Trp Lys Thr
2625                2630                2635                2640
Gln Arg Lys Gly Ile Asn Ile Pro Ala Asp Gln Pro Ile Thr Lys Leu
                2645                2650                2655
Lys Asn Leu Glu Asp Val Val Pro Thr Met Glu Ile Lys Val Asp
            2660                2665                2670
His Thr Gly Glu Tyr Gly Asn Leu Val Thr Ile Gln Ser Phe Lys Ala
        2675                2680                2685
Glu Phe Arg Leu Ala Gly Gly Val Asn Leu Pro Lys Ile Ile Asp Cys
    2690                2695                2700
Val Gly Ser Asp Gly Lys Glu Arg Arg Gln Leu Val Lys Gly Arg Asp
2705                2710                2715                2720
Asp Leu Arg Gln Asp Ala Val Met Gln Gln Val Phe Gln Met Cys Asn
                2725                2730                2735
Thr Leu Leu Gln Arg Asn Thr Glu Thr Arg Lys Arg Lys Leu Thr Ile
            2740                2745                2750
Cys Thr Tyr Lys Val Val Pro Leu Ser Gln Arg Ser Gly Val Leu Glu
        2755                2760                2765
Trp Cys Thr Gly Thr Val Pro Ile Gly Glu Phe Leu Val Asn Asn Glu
    2770                2775                2780
Asp Gly Ala His Lys Arg Tyr Arg Pro Asn Asp Phe Ser Ala Phe Gln
2785                2790                2795                2800
Cys Gln Lys Lys Met Met Glu Val Gln Lys Lys Ser Phe Glu Glu Lys
                2805                2810                2815
Tyr Glu Val Phe Met Asp Val Cys Gln Asn Phe Gln Pro Val Phe Arg
            2820                2825                2830
Tyr Phe Cys Met Glu Lys Phe Leu Asp Pro Ala Ile Trp Phe Glu Lys
        2835                2840                2845
```

-continued

```
Arg Leu Ala Tyr Thr Arg Ser Val Ala Thr Ser Ser Ile Val Gly Tyr
    2850                2855                2860

Ile Leu Gly Leu Gly Asp Arg His Val Gln Asn Ile Leu Ile Asn Glu
2865                2870                2875                2880

Gln Ser Ala Glu Leu Val His Ile Asp Leu Gly Val Ala Phe Glu Gln
                2885                2890                2895

Gly Lys Ile Leu Pro Thr Pro Glu Thr Val Pro Phe Arg Leu Thr Arg
            2900                2905                2910

Asp Ile Val Asp Gly Met Gly Ile Thr Gly Val Glu Gly Val Phe Arg
            2915                2920                2925

Arg Cys Cys Glu Lys Thr Met Glu Val Met Arg Asn Ser Gln Glu Thr
        2930                2935                2940

Leu Leu Thr Ile Val Glu Val Leu Leu Tyr Asp Pro Leu Phe Asp Trp
2945                2950                2955                2960

Thr Met Asn Pro Leu Lys Ala Leu Tyr Leu Gln Gln Arg Pro Glu Asp
                2965                2970                2975

Glu Thr Glu Leu His Pro Thr Leu Asn Ala Asp Asp Gln Glu Cys Lys
            2980                2985                2990

Arg Asn Leu Ser Asp Ile Asp Gln Ser Phe Asp Lys Val Ala Glu Arg
        2995                3000                3005

Val Leu Met Arg Leu Gln Glu Lys Leu Lys Gly Val Glu Glu Gly Thr
3010                3015                3020

Val Leu Ser Val Gly Gly Gln Val Asn Leu Leu Ile Gln Gln Ala Ile
3025                3030                3035                3040

Asp Pro Lys Asn Leu Ser Arg Leu Phe Pro Gly Trp Lys Ala Trp Val
                3045                3050                3055

<210> SEQ ID NO 3
<211> LENGTH: 3057
<212> TYPE: PRT
<213> ORGANISM: Human

<400> SEQUENCE: 3

Met Ser Leu Val Leu Asn Asp Leu Leu Ile Cys Cys Arg Gln Leu Glu
1               5                   10                  15

His Asp Arg Ala Thr Glu Arg Lys Lys Glu Val Glu Lys Phe Lys Arg
            20                  25                  30

Leu Ile Arg Asp Pro Glu Thr Ile Lys His Leu Ala Ser Pro Arg His
        35                  40                  45

Ser Asp Ser Lys Gln Gly Lys Tyr Leu Asn Trp Asp Ala Val Phe Arg
    50                  55                  60

Phe Leu Gln Lys Tyr Ile Gln Lys Glu Thr Glu Cys Leu Arg Ile Ala
65                  70                  75                  80

Lys Pro Asn Val Ser Ala Ser Thr Gln Ala Ser Arg Gln Lys Lys Met
                85                  90                  95

Gln Glu Ile Ser Ser Leu Val Lys Tyr Phe Ile Lys Cys Ala Asn Arg
            100                 105                 110

Arg Ala Pro Arg Leu Lys Cys Gln Glu Leu Leu Asn Tyr Ile Met Asp
        115                 120                 125

Thr Val Lys Asp Ser Ser Asn Gly Ala Ile Tyr Gly Ala Asp Cys Ser
    130                 135                 140

Asn Ile Leu Leu Lys Asp Ile Leu Ser Val Arg Lys Tyr Trp Cys Glu
145                 150                 155                 160

Ile Ser Gln Gln Gln Trp Leu Glu Leu Phe Ser Val Tyr Phe Arg Leu
```

-continued

```
            165                 170                 175
Tyr Leu Lys Pro Ser Gln Asp Val His Arg Val Leu Val Ala Arg Ile
            180                 185                 190
Ile His Ala Val Thr Lys Gly Cys Cys Ser Gln Thr Asp Gly Leu Asn
            195                 200                 205
Ser Lys Phe Leu Asp Phe Phe Ser Lys Ala Ile Gln Cys Ala Arg Gln
            210                 215                 220
Glu Lys Ser Ser Ser Gly Leu Asn His Ile Leu Ala Ala Leu Thr Ile
225                 230                 235                 240
Phe Leu Lys Thr Leu Ala Val Asn Phe Arg Ile Arg Val Cys Glu Leu
            245                 250                 255
Gly Asp Glu Ile Leu Pro Thr Leu Leu Tyr Ile Trp Thr Gln His Arg
            260                 265                 270
Leu Asn Asp Ser Leu Lys Glu Val Ile Ile Glu Leu Phe Gln Leu Gln
            275                 280                 285
Ile Tyr Ile His His Pro Lys Gly Ala Lys Thr Gln Glu Lys Gly Ala
            290                 295                 300
Tyr Glu Ser Thr Lys Trp Arg Ser Ile Leu Tyr Asn Leu Tyr Asp Leu
305                 310                 315                 320
Leu Val Asn Glu Ile Ser His Ile Gly Ser Arg Gly Lys Tyr Ser Ser
            325                 330                 335
Gly Phe Arg Asn Ile Ala Val Lys Glu Asn Leu Ile Glu Leu Met Ala
            340                 345                 350
Asp Ile Cys His Gln Val Phe Asn Glu Asp Thr Arg Ser Leu Glu Ile
            355                 360                 365
Ser Gln Ser Tyr Thr Thr Thr Gln Arg Glu Ser Ser Asp Tyr Ser Val
            370                 375                 380
Pro Cys Lys Arg Lys Ile Glu Leu Gly Trp Glu Val Ile Lys Asp
385                 390                 395                 400
His Leu Gln Lys Ser Gln Asn Asp Phe Asp Leu Val Pro Trp Leu Gln
            405                 410                 415
Ile Ala Thr Gln Leu Ile Ser Lys Tyr Pro Ala Ser Leu Pro Asn Cys
            420                 425                 430
Glu Leu Ser Pro Leu Leu Met Ile Leu Ser Gln Leu Leu Pro Gln Gln
            435                 440                 445
Arg His Gly Glu Arg Thr Pro Tyr Val Leu Arg Cys Leu Thr Glu Val
            450                 455                 460
Ala Leu Cys Gln Asp Lys Arg Ser Asn Leu Glu Ser Ser Gln Lys Ser
465                 470                 475                 480
Asp Leu Leu Lys Leu Trp Asn Lys Ile Trp Cys Ile Thr Phe Arg Gly
            485                 490                 495
Ile Ser Ser Glu Gln Ile Gln Ala Glu Asn Phe Gly Leu Leu Gly Ala
            500                 505                 510
Ile Ile Gln Gly Ser Leu Val Glu Val Asp Arg Glu Phe Trp Lys Leu
            515                 520                 525
Phe Thr Gly Ser Ala Cys Arg Pro Ser Cys Pro Ala Val Cys Cys Leu
            530                 535                 540
Thr Leu Ala Leu Thr Thr Ser Ile Val Pro Gly Ala Val Lys Met Gly
545                 550                 555                 560
Ile Glu Gln Asn Met Cys Glu Val Asn Arg Ser Phe Ser Leu Lys Glu
            565                 570                 575
Ser Ile Met Lys Trp Leu Leu Phe Tyr Gln Leu Glu Gly Asp Leu Glu
            580                 585                 590
```

```
Asn Ser Thr Glu Val Pro Pro Ile Leu His Ser Asn Phe Pro His Leu
        595                 600                 605
Val Leu Glu Lys Ile Leu Val Ser Leu Thr Met Lys Asn Cys Lys Ala
        610                 615                 620
Ala Met Asn Phe Phe Gln Ser Val Pro Glu Cys Glu His His Gln Lys
625                 630                 635                 640
Asp Lys Glu Glu Leu Ser Phe Ser Glu Val Glu Glu Leu Phe Leu Gln
                645                 650                 655
Thr Thr Phe Asp Lys Met Asp Phe Leu Thr Ile Val Arg Glu Cys Gly
                660                 665                 670
Ile Glu Lys His Gln Ser Ser Ile Gly Phe Ser Val His Gln Asn Leu
        675                 680                 685
Lys Glu Ser Leu Asp Arg Cys Leu Leu Gly Leu Ser Glu Gln Leu Leu
        690                 695                 700
Asn Asn Tyr Ser Ser Glu Ile Thr Asn Ser Glu Thr Leu Val Arg Cys
705                 710                 715                 720
Ser Arg Leu Leu Val Gly Val Leu Gly Cys Tyr Cys Tyr Met Gly Val
                725                 730                 735
Ile Ala Glu Glu Glu Ala Tyr Lys Ser Glu Leu Phe Gln Lys Ala Asn
                740                 745                 750
Ser Leu Met Gln Cys Ala Gly Glu Ser Ile Thr Leu Phe Lys Asn Lys
        755                 760                 765
Thr Asn Glu Glu Phe Arg Ile Gly Ser Leu Arg Asn Met Met Gln Leu
        770                 775                 780
Cys Thr Arg Cys Leu Ser Asn Cys Thr Lys Lys Ser Pro Asn Lys Ile
785                 790                 795                 800
Ala Ser Gly Phe Phe Leu Arg Leu Leu Thr Ser Lys Leu Met Asn Asp
                805                 810                 815
Ile Ala Asp Ile Cys Lys Ser Leu Ala Ser Phe Ile Lys Lys Pro Phe
                820                 825                 830
Asp Arg Gly Glu Val Glu Ser Met Glu Asp Thr Asn Gly Asn Leu
        835                 840                 845
Met Glu Val Glu Asp Gln Ser Ser Met Asn Leu Phe Asn Asp Tyr Pro
850                 855                 860
Asp Ser Ser Val Ser Asp Ala Asn Glu Pro Gly Glu Ser Gln Ser Thr
865                 870                 875                 880
Ile Gly Ala Ile Asn Pro Leu Ala Glu Glu Tyr Leu Ser Lys Gln Asp
                885                 890                 895
Leu Leu Phe Leu Asp Met Leu Lys Phe Leu Cys Leu Cys Val Thr Thr
                900                 905                 910
Ala Gln Thr Asn Thr Val Ser Phe Arg Ala Ala Asp Ile Arg Arg Lys
        915                 920                 925
Leu Leu Met Leu Ile Asp Ser Ser Thr Leu Glu Pro Thr Lys Ser Leu
        930                 935                 940
His Leu His Met Tyr Leu Leu Lys Glu Leu Pro Gly Glu Glu Tyr
945                 950                 955                 960
Pro Leu Pro Met Glu Asp Val Leu Glu Leu Lys Pro Leu Ser Asn
                965                 970                 975
Val Cys Ser Leu Tyr Arg Arg Asp Gln Asp Val Cys Lys Thr Ile Leu
                980                 985                 990
Asn His Val Leu His Val Val Lys Asn Leu Gly Gln Ser Asn Met Asp
        995                 1000                1005
```

-continued

```
Ser Glu Asn Thr Arg Asp Ala Gln Gly Gln Phe Leu Thr Val Ile Gly
        1010                1015                1020

Ala Phe Trp His Leu Thr Lys Glu Arg Lys Tyr Ile Phe Ser Val Arg
1025                1030                1035                1040

Met Ala Leu Val Asn Cys Leu Lys Thr Leu Leu Glu Ala Asp Pro Tyr
                1045                1050                1055

Ser Lys Trp Ala Ile Leu Asn Val Met Gly Lys Asp Phe Pro Val Asn
                1060                1065                1070

Glu Val Phe Thr Gln Phe Leu Ala Asp Asn His His Gln Val Arg Met
            1075                1080                1085

Leu Ala Ala Glu Ser Ile Asn Arg Leu Phe Gln Asp Thr Lys Gly Asp
        1090                1095                1100

Ser Ser Arg Leu Leu Lys Ala Leu Pro Leu Lys Leu Gln Gln Thr Ala
1105                1110                1115                1120

Phe Glu Asn Ala Tyr Leu Lys Ala Gln Glu Gly Met Arg Glu Met Ser
                1125                1130                1135

His Ser Ala Glu Asn Pro Glu Thr Leu Asp Glu Ile Tyr Asn Arg Lys
                1140                1145                1150

Ser Val Leu Leu Thr Leu Ile Ala Val Val Leu Ser Cys Ser Pro Ile
            1155                1160                1165

Cys Glu Lys Gln Ala Leu Phe Ala Leu Cys Lys Ser Val Lys Glu Asn
        1170                1175                1180

Gly Leu Glu Pro His Leu Val Lys Lys Val Leu Glu Lys Val Ser Glu
1185                1190                1195                1200

Thr Phe Gly Tyr Arg Arg Leu Glu Asp Phe Met Ala Ser His Leu Asp
                1205                1210                1215

Tyr Leu Val Leu Glu Trp Leu Asn Leu Gln Asp Thr Glu Tyr Asn Leu
            1220                1225                1230

Ser Ser Phe Pro Phe Ile Leu Leu Asn Tyr Thr Asn Ile Glu Asp Phe
        1235                1240                1245

Tyr Arg Ser Cys Tyr Lys Val Leu Ile Pro His Leu Val Ile Arg Ser
1250                1255                1260

His Phe Asp Cys Val Lys Ser Ile Ala Asn Gln Ile Gln Glu Asp Trp
1265                1270                1275                1280

Lys Ser Leu Leu Thr Asp Cys Phe Pro Lys Ile Leu Val Asn Ile Leu
                1285                1290                1295

Pro Tyr Phe Ala Tyr Glu Gly Thr Arg Asp Ser Gly Met Ala Gln Gln
            1300                1305                1310

Arg Glu Thr Ala Thr Lys Val Tyr Asp Met Leu Lys Ser Glu Asn Leu
        1315                1320                1325

Leu Gly Lys Gln Ile Asp His Leu Phe Ile Ser Asn Leu Pro Glu Ile
    1330                1335                1340

Val Val Glu Leu Leu Met Thr Leu His Glu Pro Ala Asn Ser Ser Ala
1345                1350                1355                1360

Ser Gln Ser Thr Asp Leu Cys Asp Phe Ser Gly Asp Leu Asp Pro Ala
                1365                1370                1375

Pro Asn Pro Pro His Phe Pro Ser His Val Ile Lys Ala Thr Phe Ala
            1380                1385                1390

Tyr Ile Ser Asn Cys His Lys Thr Lys Leu Lys Ser Ile Leu Glu Ile
        1395                1400                1405

Leu Ser Lys Ser Pro Asp Ser Tyr Gln Lys Ile Leu Leu Ala Ile Cys
    1410                1415                1420

Glu Gln Ala Ala Glu Thr Asn Asn Val Tyr Lys Lys His Arg Ile Leu
```

-continued

```
            1425                1430                1435                1440
Lys Ile Tyr His Leu Phe Val Ser Leu Leu Lys Asp Ile Lys Ser
                1445                1450                1455
Gly Leu Gly Gly Ala Trp Ala Phe Val Leu Arg Asp Val Ile Tyr Thr
                1460                1465                1470
Leu Ile His Tyr Ile Asn Gln Arg Pro Ser Cys Ile Met Asp Val Ser
                1475                1480                1485
Leu Arg Ser Phe Ser Leu Cys Cys Asp Leu Leu Ser Gln Val Cys Gln
                1490                1495                1500
Thr Ala Val Thr Tyr Cys Lys Asp Ala Leu Glu Asn His Leu His Val
1505                1510                1515                1520
Ile Val Gly Thr Leu Ile Pro Leu Val Tyr Glu Gln Val Glu Val Gln
                1525                1530                1535
Lys Gln Val Leu Asp Leu Leu Lys Tyr Leu Val Ile Asp Asn Lys Asp
                1540                1545                1550
Asn Glu Asn Leu Tyr Ile Thr Ile Lys Leu Leu Asp Pro Phe Pro Asp
                1555                1560                1565
His Val Val Phe Lys Asp Leu Arg Ile Thr Gln Gln Lys Ile Lys Tyr
                1570                1575                1580
Ser Arg Gly Pro Phe Ser Leu Leu Glu Glu Ile Asn His Phe Leu Ser
1585                1590                1595                1600
Val Ser Val Tyr Asp Ala Leu Pro Leu Thr Arg Leu Glu Gly Leu Lys
                1605                1610                1615
Asp Leu Arg Arg Gln Leu Glu Leu His Lys Asp Gln Met Val Asp Ile
                1620                1625                1630
Met Arg Ala Ser Gln Asp Asn Pro Gln Asp Gly Ile Met Val Lys Leu
                1635                1640                1645
Val Val Asn Leu Leu Gln Leu Ser Lys Met Ala Ile Asn His Thr Gly
                1650                1655                1660
Glu Lys Glu Val Leu Glu Ala Val Gly Ser Cys Leu Gly Glu Val Gly
1665                1670                1675                1680
Pro Ile Asp Phe Ser Thr Ile Ala Ile Gln His Ser Lys Asp Ala Ser
                1685                1690                1695
Tyr Thr Lys Ala Leu Lys Leu Phe Glu Asp Lys Glu Leu Gln Trp Thr
                1700                1705                1710
Phe Ile Met Leu Thr Tyr Leu Asn Asn Thr Leu Val Glu Asp Cys Val
                1715                1720                1725
Lys Val Arg Ser Ala Ala Val Thr Cys Leu Lys Asn Ile Leu Ala Thr
                1730                1735                1740
Lys Thr Gly His Ser Phe Trp Glu Ile Tyr Lys Met Thr Thr Asp Pro
1745                1750                1755                1760
Met Leu Ala Tyr Leu Gln Pro Phe Arg Thr Ser Arg Lys Lys Phe Leu
                1765                1770                1775
Glu Val Pro Arg Phe Asp Lys Glu Asn Pro Phe Glu Gly Leu Asp Asp
                1780                1785                1790
Ile Asn Leu Trp Ile Pro Leu Ser Glu Asn His Asp Ile Trp Ile Lys
                1795                1800                1805
Thr Leu Thr Cys Ala Phe Leu Asp Ser Gly Gly Thr Lys Cys Glu Ile
                1810                1815                1820
Leu Gln Leu Leu Lys Pro Met Cys Glu Val Lys Thr Asp Phe Cys Gln
1825                1830                1835                1840
Thr Val Leu Pro Tyr Leu Ile His Asp Ile Leu Leu Gln Asp Thr Asn
                1845                1850                1855
```

```
Glu Ser Trp Arg Asn Leu Leu Ser Thr His Val Gln Gly Phe Phe Thr
            1860                1865                1870

Ser Cys Leu Arg His Phe Ser Gln Thr Ser Arg Ser Thr Thr Pro Ala
        1875                1880                1885

Asn Leu Asp Ser Glu Ser Glu His Phe Phe Arg Cys Cys Leu Asp Lys
    1890                1895                1900

Lys Ser Gln Arg Thr Met Leu Ala Val Val Asp Tyr Met Arg Arg Gln
1905                1910                1915                1920

Lys Arg Pro Ser Ser Gly Thr Ile Phe Asn Asp Ala Phe Trp Leu Asp
            1925                1930                1935

Leu Asn Tyr Leu Glu Val Ala Lys Val Ala Gln Ser Cys Ala Ala His
        1940                1945                1950

Phe Thr Ala Leu Leu Tyr Ala Glu Ile Tyr Ala Asp Lys Lys Ser Met
    1955                1960                1965

Asp Asp Gln Glu Lys Arg Ser Leu Ala Phe Glu Glu Gly Ser Gln Ser
1970                1975                1980

Thr Thr Ile Ser Ser Leu Ser Glu Lys Ser Lys Glu Glu Thr Gly Ile
1985                1990                1995                2000

Ser Leu Gln Asp Leu Leu Leu Glu Ile Tyr Arg Ser Ile Gly Glu Pro
            2005                2010                2015

Asp Ser Leu Tyr Gly Cys Gly Gly Gly Lys Met Leu Gln Pro Ile Thr
        2020                2025                2030

Arg Leu Arg Thr Tyr Glu His Glu Ala Met Trp Gly Lys Ala Leu Val
    2035                2040                2045

Thr Tyr Asp Leu Glu Thr Ala Ile Pro Ser Ser Thr Arg Gln Ala Gly
2050                2055                2060

Ile Ile Gln Ala Leu Gln Asn Leu Gly Leu Cys His Ile Leu Ser Val
2065                2070                2075                2080

Tyr Leu Lys Gly Leu Asp Tyr Glu Asn Lys Asp Trp Cys Pro Glu Leu
            2085                2090                2095

Glu Glu Leu His Tyr Gln Ala Ala Trp Arg Asn Met Gln Trp Asp His
        2100                2105                2110

Cys Thr Ser Val Ser Lys Glu Val Glu Gly Thr Ser Tyr His Glu Ser
    2115                2120                2125

Leu Tyr Asn Ala Leu Gln Ser Leu Arg Asp Arg Glu Phe Ser Thr Phe
2130                2135                2140

Tyr Glu Ser Leu Lys Tyr Ala Arg Val Lys Glu Val Glu Glu Met Cys
2145                2150                2155                2160

Lys Arg Ser Leu Glu Ser Val Tyr Ser Leu Tyr Pro Thr Leu Ser Arg
            2165                2170                2175

Leu Gln Ala Ile Gly Glu Leu Glu Ser Ile Gly Glu Leu Phe Ser Arg
        2180                2185                2190

Ser Val Thr His Arg Gln Leu Ser Glu Val Tyr Ile Lys Trp Gln Lys
    2195                2200                2205

His Ser Gln Leu Leu Lys Asp Ser Asp Phe Ser Phe Gln Glu Pro Ile
2210                2215                2220

Met Ala Leu Arg Thr Val Ile Leu Glu Ile Leu Met Glu Lys Glu Met
2225                2230                2235                2240

Asp Asn Ser Gln Arg Glu Cys Ile Lys Asp Ile Leu Thr Lys His Leu
            2245                2250                2255

Val Glu Leu Ser Ile Leu Ala Arg Thr Phe Lys Asn Thr Gln Leu Pro
        2260                2265                2270
```

-continued

Glu Arg Ala Ile Phe Gln Ile Lys Gln Tyr Asn Ser Val Ser Cys Gly
    2275                2280                2285

Val Ser Glu Trp Gln Leu Glu Glu Ala Gln Val Phe Trp Ala Lys Lys
    2290                2295                2300

Glu Gln Ser Leu Ala Leu Ser Ile Leu Lys Gln Met Ile Lys Lys Leu
2305                2310                2315                2320

Asp Ala Ser Cys Ala Ala Asn Asn Pro Ser Leu Lys Leu Thr Tyr Thr
                2325                2330                2335

Glu Cys Leu Arg Val Cys Gly Asn Trp Leu Ala Glu Thr Cys Leu Glu
                2340                2345                2350

Asn Pro Ala Val Ile Met Gln Thr Tyr Leu Glu Lys Ala Val Glu Val
                2355                2360                2365

Ala Gly Asn Tyr Asp Gly Glu Ser Ser Asp Glu Leu Arg Asn Gly Lys
    2370                2375                2380

Met Lys Ala Phe Leu Ser Leu Ala Arg Phe Ser Asp Thr Gln Tyr Gln
2385                2390                2395                2400

Arg Ile Glu Asn Tyr Met Lys Ser Ser Glu Phe Glu Asn Lys Gln Ala
                2405                2410                2415

Leu Leu Lys Arg Ala Lys Glu Glu Val Gly Leu Leu Arg Glu His Lys
    2420                2425                2430

Ile Gln Thr Asn Arg Tyr Thr Val Lys Val Gln Arg Glu Leu Glu Leu
    2435                2440                2445

Asp Glu Leu Ala Leu Arg Ala Leu Lys Glu Asp Arg Lys Arg Phe Leu
    2450                2455                2460

Cys Lys Ala Val Glu Asn Tyr Ile Asn Cys Leu Leu Ser Gly Glu Glu
2465                2470                2475                2480

His Asp Met Trp Val Phe Arg Leu Cys Ser Leu Trp Leu Glu Asn Ser
                2485                2490                2495

Gly Val Ser Glu Val Asn Gly Met Met Lys Arg Asp Gly Met Lys Ile
                2500                2505                2510

Pro Thr Tyr Lys Phe Leu Pro Leu Met Tyr Gln Leu Ala Ala Arg Met
    2515                2520                2525

Gly Thr Lys Met Met Gly Gly Leu Gly Phe His Glu Val Leu Asn Asn
    2530                2535                2540

Leu Ile Ser Arg Ile Ser Met Asp His Pro His His Thr Leu Phe Ile
2545                2550                2555                2560

Ile Leu Ala Leu Ala Asn Ala Asn Arg Asp Glu Phe Leu Thr Lys Pro
                2565                2570                2575

Glu Val Ala Arg Arg Ser Arg Ile Thr Lys Asn Val Pro Lys Gln Ser
                2580                2585                2590

Ser Gln Leu Asp Glu Asp Arg Thr Glu Ala Ala Asn Arg Ile Ile Cys
    2595                2600                2605

Thr Ile Arg Ser Arg Arg Pro Gln Met Val Arg Ser Val Glu Ala Leu
    2610                2615                2620

Cys Asp Ala Tyr Ile Ile Leu Ala Asn Leu Asp Ala Thr Gln Trp Lys
2625                2630                2635                2640

Thr Gln Arg Lys Gly Ile Asn Ile Pro Ala Asp Gln Pro Ile Thr Lys
                2645                2650                2655

Leu Lys Asn Leu Glu Asp Val Val Val Pro Thr Met Glu Ile Lys Val
                2660                2665                2670

Asp His Thr Gly Glu Tyr Gly Asn Leu Val Thr Ile Gln Ser Phe Lys
    2675                2680                2685

Ala Glu Phe Arg Leu Ala Gly Gly Val Asn Leu Pro Lys Ile Ile Asp

-continued

```
                    2690                2695                2700
Cys Val Gly Ser Asp Gly Lys Glu Arg Arg Gln Leu Val Lys Gly Arg
2705                2710                2715                2720
Asp Asp Leu Arg Gln Asp Ala Val Met Gln Gln Val Phe Gln Met Cys
                    2725                2730                2735
Asn Thr Leu Leu Gln Arg Asn Thr Glu Thr Arg Lys Arg Lys Leu Thr
                    2740                2745                2750
Ile Cys Thr Tyr Lys Val Val Pro Leu Ser Gln Arg Ser Gly Val Leu
                    2755                2760                2765
Glu Trp Cys Thr Gly Thr Val Pro Ile Gly Glu Phe Leu Val Asn Asn
            2770                2775                2780
Glu Asp Gly Ala His Lys Arg Tyr Arg Pro Asn Asp Phe Ser Ala Phe
2785                2790                2795                2800
Gln Cys Gln Lys Lys Met Met Glu Val Gln Lys Ser Phe Glu Glu
                    2805                2810                2815
Lys Tyr Glu Val Phe Met Asp Val Cys Gln Asn Phe Gln Pro Val Phe
                    2820                2825                2830
Arg Tyr Phe Cys Met Glu Lys Phe Leu Asp Pro Ala Ile Trp Phe Glu
            2835                2840                2845
Lys Arg Leu Ala Tyr Thr Arg Ser Val Ala Thr Ser Ser Ile Val Gly
            2850                2855                2860
Tyr Ile Leu Gly Leu Gly Asp Arg His Val Gln Asn Ile Leu Ile Asn
2865                2870                2875                2880
Glu Gln Ser Ala Glu Leu Val His Ile Asp Leu Gly Val Ala Phe Glu
                    2885                2890                2895
Gln Gly Lys Ile Leu Pro Thr Pro Glu Thr Val Pro Phe Arg Leu Thr
                    2900                2905                2910
Arg Asp Ile Val Asp Gly Met Gly Ile Thr Gly Val Glu Gly Val Phe
                    2915                2920                2925
Arg Arg Cys Cys Glu Lys Thr Met Glu Val Met Arg Asn Ser Gln Glu
            2930                2935                2940
Thr Leu Leu Thr Ile Val Glu Val Leu Leu Tyr Asp Pro Leu Phe Asp
2945                2950                2955                2960
Trp Thr Met Asn Pro Leu Lys Ala Leu Tyr Leu Gln Gln Arg Pro Glu
                    2965                2970                2975
Asp Glu Thr Glu Leu His Pro Thr Leu Asn Ala Asp Asp Gln Glu Cys
                    2980                2985                2990
Lys Arg Asn Leu Ser Asp Ile Asp Gln Ser Phe Asp Lys Val Ala Glu
            2995                3000                3005
Arg Val Leu Met Arg Leu Gln Glu Lys Leu Lys Gly Val Glu Glu Gly
            3010                3015                3020
Thr Val Leu Ser Val Gly Gly Gln Val Asn Leu Leu Ile Gln Gln Ala
3025                3030                3035                3040
Ile Asp Pro Lys Asn Leu Ser Arg Leu Phe Pro Gly Trp Lys Ala Trp
                    3045                3050                3055
Val
```

<210> SEQ ID NO 4
<211> LENGTH: 17
<212> TYPE: DNA
<213> ORGANISM: Human

<400> SEQUENCE: 4
tccgcgctta cccaata                                              17

-continued

<210> SEQ ID NO 5
<211> LENGTH: 17
<212> TYPE: DNA
<213> ORGANISM: Human

<400> SEQUENCE: 5
atggccagcg acttagc                                                17

<210> SEQ ID NO 6
<211> LENGTH: 17
<212> TYPE: DNA
<213> ORGANISM: Human

<400> SEQUENCE: 6
aagagggtgg gtgagag                                                17

<210> SEQ ID NO 7
<211> LENGTH: 17
<212> TYPE: DNA
<213> ORGANISM: Human

<400> SEQUENCE: 7
cactcggaag gtcaaag                                                17

<210> SEQ ID NO 8
<211> LENGTH: 19
<212> TYPE: DNA
<213> ORGANISM: Human

<400> SEQUENCE: 8
cgacgggccg aatgtttgg                                              19

<210> SEQ ID NO 9
<211> LENGTH: 20
<212> TYPE: DNA
<213> ORGANISM: Human

<400> SEQUENCE: 9
aggagaggga ggagtcaagg                                             20

<210> SEQ ID NO 10
<211> LENGTH: 18
<212> TYPE: DNA
<213> ORGANISM: Human

<400> SEQUENCE: 10
cctctcctca ctccatct                                               18

<210> SEQ ID NO 11
<211> LENGTH: 20
<212> TYPE: DNA
<213> ORGANISM: Human

<400> SEQUENCE: 11
cttccgttat gactgtttcg                                             20

<210> SEQ ID NO 12
<211> LENGTH: 20
<212> TYPE: DNA
<213> ORGANISM: Human

<400> SEQUENCE: 12

-continued cgaaacagtc ataacggaag                    20

<210> SEQ ID NO 13
<211> LENGTH: 22
<212> TYPE: DNA
<213> ORGANISM: Human

<400> SEQUENCE: 13
gataaaagga aaacaatac ta                  22

<210> SEQ ID NO 14
<211> LENGTH: 22
<212> TYPE: DNA
<213> ORGANISM: Human

<400> SEQUENCE: 14
gtttatctaa aatgattctc tc                 22

<210> SEQ ID NO 15
<211> LENGTH: 22
<212> TYPE: DNA
<213> ORGANISM: Human

<400> SEQUENCE: 15
gatgcaaaca atatttacta ct                 22

<210> SEQ ID NO 16
<211> LENGTH: 19
<212> TYPE: DNA
<213> ORGANISM: Human

<400> SEQUENCE: 16
ctctgataac ctcctactt                     19

<210> SEQ ID NO 17
<211> LENGTH: 20
<212> TYPE: DNA
<213> ORGANISM: Human

<400> SEQUENCE: 17
gaatagaaaa cagccaggta                    20

<210> SEQ ID NO 18
<211> LENGTH: 21
<212> TYPE: DNA
<213> ORGANISM: Human

<400> SEQUENCE: 18
aatgttaaat ccttgagtgc t                  21

<210> SEQ ID NO 19
<211> LENGTH: 21
<212> TYPE: DNA
<213> ORGANISM: Human

<400> SEQUENCE: 19
cacaaaaatg tttgccttgc t                  21

<210> SEQ ID NO 20
<211> LENGTH: 19
<212> TYPE: DNA
<213> ORGANISM: Human

<400> SEQUENCE: 20
ttaatcctgc tactactgc                                         19

<210> SEQ ID NO 21
<211> LENGTH: 23
<212> TYPE: DNA
<213> ORGANISM: Human

<400> SEQUENCE: 21
tgaaaataaa aaggaaataa tgg                                    23

<210> SEQ ID NO 22
<211> LENGTH: 21
<212> TYPE: DNA
<213> ORGANISM: Human

<400> SEQUENCE: 22
cagaacgaaa ggtagtaaat t                                      21

<210> SEQ ID NO 23
<211> LENGTH: 24
<212> TYPE: DNA
<213> ORGANISM: Human

<400> SEQUENCE: 23
atatatagga agcaaagata aatg                                   24

<210> SEQ ID NO 24
<211> LENGTH: 19
<212> TYPE: DNA
<213> ORGANISM: Human

<400> SEQUENCE: 24
gtaatctaag caaggtggt                                         19

<210> SEQ ID NO 25
<211> LENGTH: 24
<212> TYPE: DNA
<213> ORGANISM: Human

<400> SEQUENCE: 25
gtacttacac tcaacttta tctt                                    24

<210> SEQ ID NO 26
<211> LENGTH: 18
<212> TYPE: DNA
<213> ORGANISM: Human

<400> SEQUENCE: 26
gccattccaa gtgtctta                                          18

<210> SEQ ID NO 27
<211> LENGTH: 19
<212> TYPE: DNA
<213> ORGANISM: Human

<400> SEQUENCE: 27
tcacaaacaa caaccttca                                         19

<210> SEQ ID NO 28
<211> LENGTH: 20
<212> TYPE: DNA
<213> ORGANISM: Human

```
<400> SEQUENCE: 28
aaatcctttt tctgtatggg                                               20

<210> SEQ ID NO 29
<211> LENGTH: 22
<212> TYPE: DNA
<213> ORGANISM: Human

<400> SEQUENCE: 29
tactgagtct aaaacatggt ct                                            22

<210> SEQ ID NO 30
<211> LENGTH: 21
<212> TYPE: DNA
<213> ORGANISM: Human

<400> SEQUENCE: 30
agtgtgaagt aatgctgtga t                                             21

<210> SEQ ID NO 31
<211> LENGTH: 20
<212> TYPE: DNA
<213> ORGANISM: Human

<400> SEQUENCE: 31
tcaaccagag aaatccagag                                               20

<210> SEQ ID NO 32
<211> LENGTH: 17
<212> TYPE: DNA
<213> ORGANISM: Human

<400> SEQUENCE: 32
ccaggtgtct tctaacg                                                  17

<210> SEQ ID NO 33
<211> LENGTH: 21
<212> TYPE: DNA
<213> ORGANISM: Human

<400> SEQUENCE: 33
ttataggctt tttgtgagaa c                                             21

<210> SEQ ID NO 34
<211> LENGTH: 17
<212> TYPE: DNA
<213> ORGANISM: Human

<400> SEQUENCE: 34
ggttgtggtg atacgag                                                  17

<210> SEQ ID NO 35
<211> LENGTH: 19
<212> TYPE: DNA
<213> ORGANISM: Human

<400> SEQUENCE: 35
ctggttgaga tgaaaggat                                                19

<210> SEQ ID NO 36
<211> LENGTH: 20
<212> TYPE: DNA
<213> ORGANISM: Human
```

```
<400> SEQUENCE: 36
gtactatgga aatgatggtg                                           20

<210> SEQ ID NO 37
<211> LENGTH: 18
<212> TYPE: DNA
<213> ORGANISM: Human

<400> SEQUENCE: 37
cagggatatg tgagtgtg                                             18

<210> SEQ ID NO 38
<211> LENGTH: 18
<212> TYPE: DNA
<213> ORGANISM: Human

<400> SEQUENCE: 38
ggcactgtcc tgatagat                                             18

<210> SEQ ID NO 39
<211> LENGTH: 18
<212> TYPE: DNA
<213> ORGANISM: Human

<400> SEQUENCE: 39
gcatcaaata agtggaga                                             18

<210> SEQ ID NO 40
<211> LENGTH: 19
<212> TYPE: DNA
<213> ORGANISM: Human

<400> SEQUENCE: 40
caatggttgt cctccttaa                                            19

<210> SEQ ID NO 41
<211> LENGTH: 17
<212> TYPE: DNA
<213> ORGANISM: Human

<400> SEQUENCE: 41
agatgcagct actaccc                                              17

<210> SEQ ID NO 42
<211> LENGTH: 17
<212> TYPE: DNA
<213> ORGANISM: Human

<400> SEQUENCE: 42
gtccgaagaa gagaagc                                              17

<210> SEQ ID NO 43
<211> LENGTH: 20
<212> TYPE: DNA
<213> ORGANISM: Human

<400> SEQUENCE: 43
ctatttctcc ttcctaacag                                           20

<210> SEQ ID NO 44
<211> LENGTH: 20
<212> TYPE: DNA
```

```
<213> ORGANISM: Human

<400> SEQUENCE: 44
gttcttacaa aagatagagt                                              20

<210> SEQ ID NO 45
<211> LENGTH: 20
<212> TYPE: DNA
<213> ORGANISM: Human

<400> SEQUENCE: 45
gtcttccaaa caaatgtaat                                              20

<210> SEQ ID NO 46
<211> LENGTH: 21
<212> TYPE: DNA
<213> ORGANISM: Human

<400> SEQUENCE: 46
gtacactgta aaagcaata c                                             21

<210> SEQ ID NO 47
<211> LENGTH: 18
<212> TYPE: DNA
<213> ORGANISM: Human

<400> SEQUENCE: 47
gaggtcaagg ctacaatg                                                18

<210> SEQ ID NO 48
<211> LENGTH: 21
<212> TYPE: DNA
<213> ORGANISM: Human

<400> SEQUENCE: 48
acattccatt caagatagag a                                            21

<210> SEQ ID NO 49
<211> LENGTH: 19
<212> TYPE: DNA
<213> ORGANISM: Human

<400> SEQUENCE: 49
gctatatgtt gtgagatgc                                               19

<210> SEQ ID NO 50
<211> LENGTH: 21
<212> TYPE: DNA
<213> ORGANISM: Human

<400> SEQUENCE: 50
aaattttgac tacagcatgc t                                            21

<210> SEQ ID NO 51
<211> LENGTH: 19
<212> TYPE: DNA
<213> ORGANISM: Human

<400> SEQUENCE: 51
cctcttatac tgccaaatc                                               19

<210> SEQ ID NO 52
<211> LENGTH: 25
```

-continued

```
<212> TYPE: DNA
<213> ORGANISM: Human

<400> SEQUENCE: 52
actataattt tgcttttcat atact                                          25

<210> SEQ ID NO 53
<211> LENGTH: 20
<212> TYPE: DNA
<213> ORGANISM: Human

<400> SEQUENCE: 53
catttagtca gcaacatcag                                                20

<210> SEQ ID NO 54
<211> LENGTH: 22
<212> TYPE: DNA
<213> ORGANISM: Human

<400> SEQUENCE: 54
ttaaagtaaa tgatttgtgg at                                             22

<210> SEQ ID NO 55
<211> LENGTH: 19
<212> TYPE: DNA
<213> ORGANISM: Human

<400> SEQUENCE: 55
cttaacagaa cacatcagt                                                 19

<210> SEQ ID NO 56
<211> LENGTH: 20
<212> TYPE: DNA
<213> ORGANISM: Human

<400> SEQUENCE: 56
ctgaaaccac tatcgtaaga                                                20

<210> SEQ ID NO 57
<211> LENGTH: 19
<212> TYPE: DNA
<213> ORGANISM: Human

<400> SEQUENCE: 57
ttgcattcgt atccacaga                                                 19

<210> SEQ ID NO 58
<211> LENGTH: 23
<212> TYPE: DNA
<213> ORGANISM: Human

<400> SEQUENCE: 58
aaagacatat tggaagtaac tta                                            23

<210> SEQ ID NO 59
<211> LENGTH: 19
<212> TYPE: DNA
<213> ORGANISM: Human

<400> SEQUENCE: 59
agcctacggg aaaagaact                                                 19

<210> SEQ ID NO 60
```

```
<211> LENGTH: 23
<212> TYPE: DNA
<213> ORGANISM: Human

<400> SEQUENCE: 60
agtaagatct ccattgaaaa ttt                                               23

<210> SEQ ID NO 61
<211> LENGTH: 18
<212> TYPE: DNA
<213> ORGANISM: Human

<400> SEQUENCE: 61
cattctactg ccatctgc                                                     18

<210> SEQ ID NO 62
<211> LENGTH: 23
<212> TYPE: DNA
<213> ORGANISM: Human

<400> SEQUENCE: 62
gtgatttatt ttgttctgga ata                                               23

<210> SEQ ID NO 63
<211> LENGTH: 21
<212> TYPE: DNA
<213> ORGANISM: Human

<400> SEQUENCE: 63
catacagttg ttttagagca g                                                 21

<210> SEQ ID NO 64
<211> LENGTH: 19
<212> TYPE: DNA
<213> ORGANISM: Human

<400> SEQUENCE: 64
tggagttcag ttgggattt                                                    19

<210> SEQ ID NO 65
<211> LENGTH: 19
<212> TYPE: DNA
<213> ORGANISM: Human

<400> SEQUENCE: 65
gtgccactca gaaaatcta                                                    19

<210> SEQ ID NO 66
<211> LENGTH: 24
<212> TYPE: DNA
<213> ORGANISM: Human

<400> SEQUENCE: 66
aagaaaagtt gaatgaatgt tgtt                                              24

<210> SEQ ID NO 67
<211> LENGTH: 19
<212> TYPE: DNA
<213> ORGANISM: Human

<400> SEQUENCE: 67
tgtgtatggg tatggtatg                                                    19
```

```
<210> SEQ ID NO 68
<211> LENGTH: 21
<212> TYPE: DNA
<213> ORGANISM: Human

<400> SEQUENCE: 68
gatactttaa tgctgatggt a                                      21

<210> SEQ ID NO 69
<211> LENGTH: 22
<212> TYPE: DNA
<213> ORGANISM: Human

<400> SEQUENCE: 69
cgaataaatc gaataaatag cc                                     22

<210> SEQ ID NO 70
<211> LENGTH: 21
<212> TYPE: DNA
<213> ORGANISM: Human

<400> SEQUENCE: 70
gtcatcgaat acttttggaa a                                      21

<210> SEQ ID NO 71
<211> LENGTH: 20
<212> TYPE: DNA
<213> ORGANISM: Human

<400> SEQUENCE: 71
ctcaattcaa aggtggctat                                        20

<210> SEQ ID NO 72
<211> LENGTH: 19
<212> TYPE: DNA
<213> ORGANISM: Human

<400> SEQUENCE: 72
cattttggaa gttcactgg                                         19

<210> SEQ ID NO 73
<211> LENGTH: 22
<212> TYPE: DNA
<213> ORGANISM: Human

<400> SEQUENCE: 73
cctctttaag atgtatttac aa                                     22

<210> SEQ ID NO 74
<211> LENGTH: 24
<212> TYPE: DNA
<213> ORGANISM: Human

<400> SEQUENCE: 74
atatcaaacc caaatctaaa ttct                                   24

<210> SEQ ID NO 75
<211> LENGTH: 21
<212> TYPE: DNA
<213> ORGANISM: Human

<400> SEQUENCE: 75
aaaaaacagg aagaacagga t                                      21
```

```
<210> SEQ ID NO 76
<211> LENGTH: 20
<212> TYPE: DNA
<213> ORGANISM: Human

<400> SEQUENCE: 76
agatgctgaa caaaaggact                                                    20

<210> SEQ ID NO 77
<211> LENGTH: 21
<212> TYPE: DNA
<213> ORGANISM: Human

<400> SEQUENCE: 77
aacactcaaa tccttctaac a                                                  21

<210> SEQ ID NO 78
<211> LENGTH: 18
<212> TYPE: DNA
<213> ORGANISM: Human

<400> SEQUENCE: 78
gttttgttgg cttacttt                                                      18

<210> SEQ ID NO 79
<211> LENGTH: 18
<212> TYPE: DNA
<213> ORGANISM: Human

<400> SEQUENCE: 79
gttttgttgg cttacttt                                                      18

<210> SEQ ID NO 80
<211> LENGTH: 21
<212> TYPE: DNA
<213> ORGANISM: Human

<400> SEQUENCE: 80
gtctataaat ggcacttaac t                                                  21

<210> SEQ ID NO 81
<211> LENGTH: 19
<212> TYPE: DNA
<213> ORGANISM: Human

<400> SEQUENCE: 81
tgacaatgaa accaagagc                                                     19

<210> SEQ ID NO 82
<211> LENGTH: 24
<212> TYPE: DNA
<213> ORGANISM: Human

<400> SEQUENCE: 82
caattataaa caaaagtgtt gtct                                               24

<210> SEQ ID NO 83
<211> LENGTH: 20
<212> TYPE: DNA
<213> ORGANISM: Human

<400> SEQUENCE: 83
actacaggca acagaaaaca                                                    20
```

<210> SEQ ID NO 84
<211> LENGTH: 21
<212> TYPE: DNA
<213> ORGANISM: Human

<400> SEQUENCE: 84
tgaagtacag aaaaacagca t          21

<210> SEQ ID NO 85
<211> LENGTH: 21
<212> TYPE: DNA
<213> ORGANISM: Human

<400> SEQUENCE: 85
gtgtgaagta tcattctcca t          21

<210> SEQ ID NO 86
<211> LENGTH: 20
<212> TYPE: DNA
<213> ORGANISM: Human

<400> SEQUENCE: 86
ggtgtacttg ataggcattt            20

<210> SEQ ID NO 87
<211> LENGTH: 18
<212> TYPE: DNA
<213> ORGANISM: Human

<400> SEQUENCE: 87
tgttttagat atgctggg              18

<210> SEQ ID NO 88
<211> LENGTH: 21
<212> TYPE: DNA
<213> ORGANISM: Human

<400> SEQUENCE: 88
tacaatgatt tccacttctc t          21

<210> SEQ ID NO 89
<211> LENGTH: 21
<212> TYPE: DNA
<213> ORGANISM: Human

<400> SEQUENCE: 89
tattatgtga agatgatgtg c          21

<210> SEQ ID NO 90
<211> LENGTH: 21
<212> TYPE: DNA
<213> ORGANISM: Human

<400> SEQUENCE: 90
tcatttttac tcaaactatt g          21

<210> SEQ ID NO 91
<211> LENGTH: 21
<212> TYPE: DNA
<213> ORGANISM: Human

<400> SEQUENCE: 91

```
ccatcttaaa tccatctttc t                                              21

<210> SEQ ID NO 92
<211> LENGTH: 20
<212> TYPE: DNA
<213> ORGANISM: Human

<400> SEQUENCE: 92
ttatagcata gtgggagaca                                                20

<210> SEQ ID NO 93
<211> LENGTH: 20
<212> TYPE: DNA
<213> ORGANISM: Human

<400> SEQUENCE: 93
tttgcaacac cttcacctaa                                                20

<210> SEQ ID NO 94
<211> LENGTH: 21
<212> TYPE: DNA
<213> ORGANISM: Human

<400> SEQUENCE: 94
taagcagtca ctaccattgt a                                              21

<210> SEQ ID NO 95
<211> LENGTH: 22
<212> TYPE: DNA
<213> ORGANISM: Human

<400> SEQUENCE: 95
tataccctta ttgagacaat gc                                             22

<210> SEQ ID NO 96
<211> LENGTH: 15
<212> TYPE: DNA
<213> ORGANISM: Human

<400> SEQUENCE: 96
gtattcagga gcttc                                                     15

<210> SEQ ID NO 97
<211> LENGTH: 20
<212> TYPE: DNA
<213> ORGANISM: Human

<400> SEQUENCE: 97
atggcatctg tacagtgtct                                                20

<210> SEQ ID NO 98
<211> LENGTH: 22
<212> TYPE: DNA
<213> ORGANISM: Human

<400> SEQUENCE: 98
ttgttgtttc catgttttca gg                                             22

<210> SEQ ID NO 99
<211> LENGTH: 21
<212> TYPE: DNA
<213> ORGANISM: Human

<400> SEQUENCE: 99
```
tgcttcgtgt tcatatgttc g                       21

<210> SEQ ID NO 100
<211> LENGTH: 20
<212> TYPE: DNA
<213> ORGANISM: Human

<400> SEQUENCE: 100
gtggtggagg gaagatgtta                         20

<210> SEQ ID NO 101
<211> LENGTH: 22
<212> TYPE: DNA
<213> ORGANISM: Human

<400> SEQUENCE: 101
ctgaaataac ctcagcacta ca                      22

<210> SEQ ID NO 102
<211> LENGTH: 21
<212> TYPE: DNA
<213> ORGANISM: Human

<400> SEQUENCE: 102
tgtatctttg ctgttttttt c                       21

<210> SEQ ID NO 103
<211> LENGTH: 20
<212> TYPE: DNA
<213> ORGANISM: Human

<400> SEQUENCE: 103
cagttgttgt ttagaatgag                         20

<210> SEQ ID NO 104
<211> LENGTH: 21
<212> TYPE: DNA
<213> ORGANISM: Human

<400> SEQUENCE: 104
catgtatatc ttagggttct g                       21

<210> SEQ ID NO 105
<211> LENGTH: 23
<212> TYPE: DNA
<213> ORGANISM: Human

<400> SEQUENCE: 105
cttcatcaat gcaaatcctt aca                     23

<210> SEQ ID NO 106
<211> LENGTH: 19
<212> TYPE: DNA
<213> ORGANISM: Human

<400> SEQUENCE: 106
caaagcctat gatgagaac                          19

<210> SEQ ID NO 107
<211> LENGTH: 19
<212> TYPE: DNA
<213> ORGANISM: Human

```
<400> SEQUENCE: 107
cccacttcag ccttctaaa                                              19

<210> SEQ ID NO 108
<211> LENGTH: 23
<212> TYPE: DNA
<213> ORGANISM: Human

<400> SEQUENCE: 108
tttttcattt ctcttgctta cat                                         23

<210> SEQ ID NO 109
<211> LENGTH: 20
<212> TYPE: DNA
<213> ORGANISM: Human

<400> SEQUENCE: 109
gacatttctt tttccctcag                                             20

<210> SEQ ID NO 110
<211> LENGTH: 19
<212> TYPE: DNA
<213> ORGANISM: Human

<400> SEQUENCE: 110
ggtagttgct gctttcatt                                              19

<210> SEQ ID NO 111
<211> LENGTH: 23
<212> TYPE: DNA
<213> ORGANISM: Human

<400> SEQUENCE: 111
aaattactaa tttcaaggct cta                                         23

<210> SEQ ID NO 112
<211> LENGTH: 23
<212> TYPE: DNA
<213> ORGANISM: Human

<400> SEQUENCE: 112
acatttttaa cctgcttttt tcc                                         23

<210> SEQ ID NO 113
<211> LENGTH: 23
<212> TYPE: DNA
<213> ORGANISM: Human

<400> SEQUENCE: 113
ccatactttt ctttgctttg gaa                                         23

<210> SEQ ID NO 114
<211> LENGTH: 23
<212> TYPE: DNA
<213> ORGANISM: Human

<400> SEQUENCE: 114
ccttaatttg agtgattctt tag                                         23

<210> SEQ ID NO 115
<211> LENGTH: 20
<212> TYPE: DNA
<213> ORGANISM: Human
```

```
<400> SEQUENCE: 115
atgcaaaaac actcactcag                                              20

<210> SEQ ID NO 116
<211> LENGTH: 21
<212> TYPE: DNA
<213> ORGANISM: Human

<400> SEQUENCE: 116
agttcatggc ttttgtgttt t                                            21

<210> SEQ ID NO 117
<211> LENGTH: 20
<212> TYPE: DNA
<213> ORGANISM: Human

<400> SEQUENCE: 117
gtatacacga ttcctgacat                                              20

<210> SEQ ID NO 118
<211> LENGTH: 22
<212> TYPE: DNA
<213> ORGANISM: Human

<400> SEQUENCE: 118
tagttagtga agttttgtta ac                                           22

<210> SEQ ID NO 119
<211> LENGTH: 20
<212> TYPE: DNA
<213> ORGANISM: Human

<400> SEQUENCE: 119
tttgtatttc catttcttag                                              20

<210> SEQ ID NO 120
<211> LENGTH: 20
<212> TYPE: DNA
<213> ORGANISM: Human

<400> SEQUENCE: 120
aagcaaaatg aaaaatatgg                                              20

<210> SEQ ID NO 121
<211> LENGTH: 20
<212> TYPE: DNA
<213> ORGANISM: Human

<400> SEQUENCE: 121
ggaaagactg aatatcacac                                              20

<210> SEQ ID NO 122
<211> LENGTH: 20
<212> TYPE: DNA
<213> ORGANISM: Human

<400> SEQUENCE: 122
gaagtttaaa tgttgggtag                                              20

<210> SEQ ID NO 123
<211> LENGTH: 20
<212> TYPE: DNA
```

```
<213> ORGANISM: Human

<400> SEQUENCE: 123
agcagattta cttattaggc                                              20

<210> SEQ ID NO 124
<211> LENGTH: 20
<212> TYPE: DNA
<213> ORGANISM: Human

<400> SEQUENCE: 124
gtggtatctg ctgactattc                                              20

<210> SEQ ID NO 125
<211> LENGTH: 20
<212> TYPE: DNA
<213> ORGANISM: Human

<400> SEQUENCE: 125
accaattttg acctacataa                                              20

<210> SEQ ID NO 126
<211> LENGTH: 24
<212> TYPE: DNA
<213> ORGANISM: Human

<400> SEQUENCE: 126
gttcttaacc actatcacat cgtc                                         24

<210> SEQ ID NO 127
<211> LENGTH: 27
<212> TYPE: DNA
<213> ORGANISM: Human

<400> SEQUENCE: 127
catttctact ctacaaatct tcctcat                                      27

<210> SEQ ID NO 128
<211> LENGTH: 20
<212> TYPE: DNA
<213> ORGANISM: Human

<400> SEQUENCE: 128
ttggtttgag tgccctttgc                                              20

<210> SEQ ID NO 129
<211> LENGTH: 20
<212> TYPE: DNA
<213> ORGANISM: Human

<400> SEQUENCE: 129
ttcacccaac caaatggcat                                              20

<210> SEQ ID NO 130
<211> LENGTH: 18
<212> TYPE: DNA
<213> ORGANISM: Human

<400> SEQUENCE: 130
tcaaatgctc tttaatgg                                                18

<210> SEQ ID NO 131
<211> LENGTH: 22
```

<212> TYPE: DNA
<213> ORGANISM: Human

<400> SEQUENCE: 131
cagctgtcag ctttaataag cc        22

<210> SEQ ID NO 132
<211> LENGTH: 22
<212> TYPE: DNA
<213> ORGANISM: Human

<400> SEQUENCE: 132
tcctgttcat ctttattgcc cc        22

<210> SEQ ID NO 133
<211> LENGTH: 21
<212> TYPE: DNA
<213> ORGANISM: Human

<400> SEQUENCE: 133
gccaaacaac aaagtgctca a        21

<210> SEQ ID NO 134
<211> LENGTH: 19
<212> TYPE: DNA
<213> ORGANISM: Human

<400> SEQUENCE: 134
gtgatttcag attgtttgt        19

<210> SEQ ID NO 135
<211> LENGTH: 20
<212> TYPE: DNA
<213> ORGANISM: Human

<400> SEQUENCE: 135
atgatgacca aatatttact        20

<210> SEQ ID NO 136
<211> LENGTH: 19
<212> TYPE: DNA
<213> ORGANISM: Human

<400> SEQUENCE: 136
tgtggtttct tgcctttgt        19

<210> SEQ ID NO 137
<211> LENGTH: 19
<212> TYPE: DNA
<213> ORGANISM: Human

<400> SEQUENCE: 137
ccagcccatg taattttga        19

<210> SEQ ID NO 138
<211> LENGTH: 23
<212> TYPE: DNA
<213> ORGANISM: Human

<400> SEQUENCE: 138
ctctgccaag tattatgcta ttt        23

<210> SEQ ID NO 139

```
<211> LENGTH: 21
<212> TYPE: DNA
<213> ORGANISM: Human

<400> SEQUENCE: 139
gacttcctga cgagatacac a                                              21

<210> SEQ ID NO 140
<211> LENGTH: 19
<212> TYPE: DNA
<213> ORGANISM: Human

<400> SEQUENCE: 140
tgtttctaag tatgtgatt                                                 19

<210> SEQ ID NO 141
<211> LENGTH: 24
<212> TYPE: DNA
<213> ORGANISM: Human

<400> SEQUENCE: 141
cactaaggac aaaaacacaa aggt                                           24

<210> SEQ ID NO 142
<211> LENGTH: 19
<212> TYPE: DNA
<213> ORGANISM: Human

<400> SEQUENCE: 142
ttaaactgtt cacctcact                                                 19

<210> SEQ ID NO 143
<211> LENGTH: 19
<212> TYPE: DNA
<213> ORGANISM: Human

<400> SEQUENCE: 143
ggcaggttaa aaataaagg                                                 19
```